US012708775B2

(12) United States Patent
Murphy

(10) Patent No.: US 12,708,775 B2
(45) Date of Patent: Aug. 18, 2026

(54) STOCHASTIC STIMULATION SCHEDULING

(71) Applicant: ONWARD MEDICAL N.V., Eindhoven (NL)

(72) Inventor: John Murphy, Eindhoven (NL)

(73) Assignee: Onward Medical N.V., Eindhoven (NL)

( * ) Notice: Subject to any disclaimer, the term of this patent is extended or adjusted under 35 U.S.C. 154(b) by 302 days.

(21) Appl. No.: 18/297,222

(22) Filed: Apr. 7, 2023

(65) Prior Publication Data

US 2024/0335666 A1 Oct. 10, 2024

(51) Int. Cl.
*A61N 1/36* (2006.01)
*A61N 1/02* (2006.01)
*A61N 1/372* (2006.01)

(52) U.S. Cl.
CPC ......... *A61N 1/36167* (2013.01); *A61N 1/025* (2013.01); *A61N 1/37235* (2013.01)

(58) Field of Classification Search
CPC ........................ A61N 1/36142; A61N 1/36167
See application file for complete search history.

(56) References Cited

U.S. PATENT DOCUMENTS 2,868,343 A 1/1959 Sproul
3,543,761 A 12/1970 Bradley
3,650,277 A 3/1972 Sjostrand et al.
3,653,518 A 4/1972 Polen
3,662,758 A 5/1972 Glover
3,724,467 A 4/1973 Avery et al.
(Continued)

FOREIGN PATENT DOCUMENTS

AU 2012204526 B2 5/2016
CA 2649663 A1 11/2007
(Continued)

OTHER PUBLICATIONS

Pudo, D. et al., "Estimating Intensity Fluctuations in High Repetition Rate Pulse Trains Generated Using the Temporal Talbot Effect", IEEE Photonics Technology Letters, vol. 18, No. 5, (Mar. 1, 2006), 3 pages.

(Continued)

*Primary Examiner* — William J Levicky
(74) *Attorney, Agent, or Firm* — Finnegan, Henderson, Farabow, Garrett & Dunner, LLP

(57) ABSTRACT

A stimulation scheduling system includes a control signal generator and a controller, which can form a control loop configured to generate sets of consistent pulse schedules with a controlled degree of difficulty. The control signal generator can generate a set of consistent pulse schedules using a set of corresponding stimulation parameter distributions and provide a detection parameter based on the generation of the set of consistent pulse schedules to a controller. The controller can estimate a difficulty state based on the detection parameter and update the stimulation parameter distributions based on the estimated difficulty state. The controller can model the difficulty of generating sets of consistent pulse schedules using a difficulty distribution. The difficulty state can be a parameter of the difficulty distribution. The controller can balance the difficulty of generating sets of consistent pulse schedules against the fidelity of the generated sets of pulse schedules.

22 Claims, 8 Drawing Sheets

(56) References Cited

U.S. PATENT DOCUMENTS 4,044,774 A 8/1977 Corbin et al.
4,102,344 A 7/1978 Conway et al.
4,141,365 A 2/1979 Fischell et al.
4,285,347 A 8/1981 Hess
4,303,904 A 12/1981 Chasek
4,340,063 A 7/1982 Maurer
4,340,216 A 7/1982 Murphy
4,356,902 A 11/1982 Murphy
4,379,462 A 4/1983 Borkan et al.
4,398,537 A * 8/1983 Holmbo ................ A61N 1/372 607/66
4,402,501 A 9/1983 Lohman
4,410,175 A 10/1983 Shamp
4,414,986 A 11/1983 Dickhudt et al.
4,538,624 A 9/1985 Tarjan
4,549,556 A 10/1985 Tarjan et al.
4,559,948 A 12/1985 Liss et al.
4,569,352 A 2/1986 Petrofsky et al.
4,573,481 A 3/1986 Bullara
4,574,789 A 3/1986 Forster
4,724,842 A 2/1988 Charters
4,742,054 A 5/1988 Naftchi
4,784,420 A 11/1988 Makino et al.
4,798,982 A 1/1989 Voorman
4,800,898 A 1/1989 Hess et al.
4,934,368 A 6/1990 Lynch
4,969,452 A 11/1990 Petrofsky et al.
5,002,053 A 3/1991 Garcia-Rill et al.
5,018,631 A 5/1991 Reimer
5,031,618 A 7/1991 Mullett
5,066,272 A 11/1991 Eaton et al.
5,081,989 A 1/1992 Graupe et al.
5,121,754 A 6/1992 Mullett
5,284,151 A 2/1994 Onoda
5,337,908 A 8/1994 Beck, Jr.
5,344,439 A 9/1994 Otten
5,348,544 A 9/1994 Sweeney et al.
5,354,320 A 10/1994 Schaldach et al.
5,366,813 A 11/1994 Berlin
5,374,285 A 12/1994 Vaiani et al.
5,417,719 A 5/1995 Hull et al.
5,421,783 A 6/1995 Kockelman et al.
5,441,465 A 8/1995 Hefner et al.
5,443,486 A 8/1995 Hrdlicka et al.
5,476,441 A 12/1995 Durfee et al.
5,553,270 A 9/1996 Rosenbluth
5,562,718 A 10/1996 Palermo
5,571,141 A 11/1996 McNeil et al.
5,584,818 A 12/1996 Morrison
5,601,527 A 2/1997 Selkowitz
5,626,540 A 5/1997 Hall
5,630,836 A 5/1997 Prem et al.
5,643,330 A 7/1997 Holsheimer et al.
5,643,332 A 7/1997 Stein
5,667,461 A 9/1997 Hall
5,733,322 A 3/1998 Starkebaum
5,788,606 A 8/1998 Rich
5,814,018 A 9/1998 Elson et al.
5,819,962 A 10/1998 Okubo et al.
5,876,425 A 3/1999 Gord et al.
5,877,183 A 3/1999 Cincotta
5,948,004 A 9/1999 Weijand et al.
5,958,933 A 9/1999 Naftchi
5,983,141 A 11/1999 Sluijter et al.
5,984,368 A 11/1999 Cain
6,052,624 A 4/2000 Mann
6,058,331 A 5/2000 King
6,066,163 A 5/2000 John
6,080,087 A 6/2000 Bingham
6,104,957 A 8/2000 Alo et al.
6,115,634 A 9/2000 Donders et al.
6,122,548 A 9/2000 Starkebaum et al.
6,139,475 A 10/2000 Bessler et al.
6,168,948 B1 1/2001 Anderson et al.
6,182,843 B1 2/2001 Tax et al.
6,188,927 B1 2/2001 Lu et al.
6,236,892 B1 5/2001 Feler
6,280,640 B1 8/2001 Hurwitz et al.
6,281,207 B1 8/2001 Richter et al.
6,308,103 B1 10/2001 Gielen
6,309,401 B1 10/2001 Redko et al.
6,319,241 B1 11/2001 King et al.
D454,139 S 3/2002 Feldcamp
6,463,327 B1 10/2002 Lurie et al.
6,464,208 B1 10/2002 Smith
6,470,213 B1 10/2002 Alley
6,490,486 B1 12/2002 Bradley
6,500,110 B1 12/2002 Davey et al.
6,503,231 B1 1/2003 Prausnitz et al.
6,505,074 B2 1/2003 Boveja et al.
6,516,227 B1 2/2003 Meadows et al.
6,551,849 B1 4/2003 Kenney
6,587,724 B2 7/2003 Mann
6,662,053 B2 12/2003 Borkan
6,666,831 B1 12/2003 Edgerton et al.
6,685,729 B2 2/2004 Gonzalez
6,748,276 B1 6/2004 Daignault, Jr. et al.
6,819,956 B2 11/2004 DiLorenzo
6,839,594 B2 1/2005 Cohen et al.
6,862,479 B1 3/2005 Whitehurst et al.
6,871,099 B1 3/2005 Whitehurst et al.
6,878,112 B2 4/2005 Linberg et al.
6,892,098 B2 5/2005 Ayal et al.
6,895,280 B2 5/2005 Meadows et al.
6,895,283 B2 5/2005 Erickson et al.
6,901,292 B2 5/2005 Hrdlicka et al.
6,937,891 B2 8/2005 Leinders et al.
6,950,706 B2 9/2005 Rodriguez et al.
6,975,907 B2 12/2005 Zanakis et al.
6,978,181 B1 12/2005 Snell
6,988,006 B2 1/2006 King et al.
6,999,820 B2 2/2006 Jordan
7,010,749 B2 3/2006 Hasha et al.
7,020,521 B1 3/2006 Brewer et al.
7,024,247 B2 4/2006 Gliner et al.
7,035,690 B2 4/2006 Goetz
7,047,084 B2 5/2006 Erickson et al.
7,065,408 B2 6/2006 Herman et al.
7,096,070 B1 8/2006 Jenkins et al.
7,099,718 B1 8/2006 Thacker et al.
7,110,820 B2 9/2006 Tcheng et al.
7,125,388 B1 10/2006 Reinkensmeyer et al.
7,127,287 B2 10/2006 Duncan et al.
7,127,296 B2 10/2006 Bradley
7,127,297 B2 10/2006 Law et al.
7,135,497 B1 11/2006 Zeman et al.
7,146,221 B2 12/2006 Krulevitch et al.
7,149,773 B2 12/2006 Haller et al.
7,153,242 B2 12/2006 Goffer
7,184,837 B2 2/2007 Goetz
7,200,443 B2 4/2007 Faul
7,209,787 B2 4/2007 DiLorenzo
7,228,179 B2 6/2007 Campen et al.
7,239,920 B1 7/2007 Thacker et al.
7,251,529 B2 7/2007 Greenwood-Van Meerveld
7,252,090 B2 8/2007 Goetz
7,313,440 B2 12/2007 Miesel
7,324,853 B2 1/2008 Ayal et al.
7,330,760 B2 2/2008 Heruth et al.
7,330,762 B2 2/2008 Boveja et al.
7,337,005 B2 2/2008 Kim et al.
7,337,006 B2 2/2008 Kim et al.
7,340,298 B1 3/2008 Barbut
7,377,006 B2 5/2008 Genoa et al.
7,381,192 B2 6/2008 Brodard et al.
7,415,309 B2 8/2008 McIntyre
7,450,992 B1 11/2008 Cameron
7,463,927 B1 12/2008 Chaouat
7,463,928 B2 12/2008 Lee et al.
7,467,016 B2 12/2008 Colborn
7,493,170 B1 2/2009 Segel et al.
7,496,404 B2 2/2009 Meadows et al.
7,502,652 B2 3/2009 Gaunt et al.
7,536,226 B2 5/2009 Williams et al.

(56) References Cited

U.S. PATENT DOCUMENTS

D594,024 S 6/2009 King
D595,308 S 6/2009 King
7,544,185 B2 6/2009 Bengtsson
7,565,195 B1 7/2009 Kroll et al.
7,584,000 B2 9/2009 Erickson
7,590,454 B2 9/2009 Garabedian et al.
7,603,178 B2 10/2009 North et al.
7,620,502 B2 11/2009 Selifonov et al.
7,628,750 B2 12/2009 Cohen et al.
7,647,115 B2 1/2010 Levin et al.
7,660,636 B2 2/2010 Castel et al.
7,697,995 B2 4/2010 Cross, Jr. et al.
7,725,193 B1 5/2010 Chu
7,729,781 B2 6/2010 Swoyer et al.
7,734,340 B2 6/2010 De Ridder
7,734,351 B2 6/2010 Testerman et al.
7,742,037 B2 6/2010 Sako et al.
7,769,463 B2 8/2010 Katsnelson
7,769,464 B2 8/2010 Gerber et al.
7,780,617 B2 8/2010 Tornatore et al.
7,797,057 B2 9/2010 Harris
7,801,600 B1 9/2010 Carbunaru et al.
7,801,601 B2 9/2010 Maschino et al.
7,813,803 B2 10/2010 Heruth et al.
7,813,809 B2 10/2010 Strother et al.
7,840,270 B2 11/2010 Ignagni et al.
7,856,264 B2 12/2010 Firlik et al.
7,861,872 B2 1/2011 Ng et al.
7,877,146 B2 1/2011 Rezai et al.
7,890,182 B2 2/2011 Parramon et al.
D638,439 S 5/2011 Cavanaugh et al.
7,949,395 B2 5/2011 Kuzma
7,949,403 B2 5/2011 Palermo et al.
7,987,000 B2 7/2011 Moffitt et al.
7,991,465 B2 8/2011 Bartic et al.
8,019,427 B2 9/2011 Moffitt
8,050,773 B2 11/2011 Zhu
8,063,087 B2 11/2011 Chow et al.
8,100,815 B2 1/2012 Balaker et al.
8,108,051 B2 1/2012 Cross, Jr. et al.
8,108,052 B2 1/2012 Boling
D656,153 S 3/2012 Imamura et al.
8,131,358 B2 3/2012 Moffitt et al.
8,135,473 B2 3/2012 Miesel et al.
8,155,750 B2 4/2012 Jaax et al.
8,168,481 B2 5/2012 Hanaoka et al.
8,170,660 B2 5/2012 Dacey, Jr. et al.
8,190,262 B2 5/2012 Gerber et al.
8,195,304 B2 6/2012 Strother et al.
8,214,048 B1 7/2012 Whitehurst et al.
8,224,453 B2 7/2012 De Ridder
8,229,565 B2 7/2012 Kim et al.
8,238,666 B2 8/2012 Besley et al.
8,239,038 B2 8/2012 Wolf, II
8,260,436 B2 9/2012 Gerber et al.
8,265,770 B2 9/2012 Toy et al.
8,271,099 B1 9/2012 Swanson
8,295,936 B2 10/2012 Wahlstrand et al.
8,311,644 B2 11/2012 Moffitt et al.
8,326,569 B2 12/2012 Lee et al.
8,332,029 B2 12/2012 Glukhovsky et al.
8,332,047 B2 12/2012 Libbus et al.
8,332,053 B1 12/2012 Patterson et al.
8,346,366 B2 1/2013 Arle et al.
8,352,036 B2 1/2013 Dimarco et al.
8,355,791 B2 1/2013 Moffitt
8,355,797 B2 1/2013 Caparso et al.
8,364,273 B2 1/2013 De Ridder
8,369,961 B2 2/2013 Christman et al.
8,374,696 B2 2/2013 Sanchez et al.
D677,674 S 3/2013 Rampson et al.
8,407,576 B1 3/2013 Yin et al.
8,412,345 B2 4/2013 Moffitt
8,428,728 B2 4/2013 Sachs
8,442,655 B2 5/2013 Moffitt et al.
8,452,406 B2 5/2013 Arcot-Krishnamurthy et al.
D684,991 S 6/2013 Wenz et al.
D684,996 S 6/2013 Wenz et al.
D688,259 S 8/2013 Pearcy et al.
D689,086 S 9/2013 Philopoulos
8,543,200 B2 9/2013 Lane et al.
D691,154 S 10/2013 Talbot et al.
D691,172 S 10/2013 Wujcik et al.
8,588,884 B2 11/2013 Hegde et al.
D694,763 S 12/2013 Edwards et al.
8,626,300 B2 1/2014 Demarais et al.
8,630,717 B2 1/2014 Olson et al.
8,700,145 B2 4/2014 Kilgard et al.
8,712,546 B2 4/2014 Kim et al.
D705,241 S 5/2014 Chen et al.
D707,235 S 6/2014 Arnold et al.
8,740,825 B2 6/2014 Ehrenreich et al.
8,750,957 B2 6/2014 Tang et al.
RE45,030 E 7/2014 Stevenson et al.
8,766,928 B2 7/2014 Weeldreyer et al.
8,768,472 B2 7/2014 Fang et al.
8,768,481 B2 7/2014 Lane
8,788,046 B2 7/2014 Bennett et al.
8,805,542 B2 8/2014 Tai et al.
8,836,368 B2 9/2014 Afshar et al.
8,847,548 B2 9/2014 Kesler et al.
8,849,410 B2 9/2014 Walker et al.
8,849,418 B2 9/2014 Daglow
8,897,870 B2 11/2014 De Ridder
8,903,502 B2 12/2014 Perryman et al.
D721,722 S 1/2015 Lee
8,957,549 B2 2/2015 Kesler et al.
D735,231 S 7/2015 Omiya
9,072,891 B1 7/2015 Rao
9,079,039 B2 7/2015 Carlson et al.
9,101,769 B2 8/2015 Edgerton et al.
D737,840 S 9/2015 Omiya
9,192,768 B2 11/2015 Yokoi et al.
9,205,259 B2 12/2015 Kim et al.
9,205,260 B2 12/2015 Kim et al.
9,205,261 B2 12/2015 Kim et al.
9,248,291 B2 2/2016 Mashiach
D750,664 S 3/2016 Chen et al.
9,272,139 B2 3/2016 Hamilton et al.
9,272,143 B2 3/2016 Libbus et al.
9,283,391 B2 3/2016 Ahmed
9,314,630 B2 4/2016 Levin et al.
D758,398 S 6/2016 Yu et al.
9,358,384 B2 6/2016 Dubuclet
D760,753 S 7/2016 Cheng et al.
D762,234 S 7/2016 Li et al.
9,393,409 B2 7/2016 Edgerton et al.
D763,273 S 8/2016 Hwang et al.
9,409,023 B2 8/2016 Burdick et al.
9,409,030 B2 8/2016 Perryman et al.
9,415,218 B2 8/2016 Edgerton et al.
9,421,365 B2 8/2016 Sumners et al.
D769,302 S 10/2016 Rodriguez
D770,468 S 11/2016 Carlson et al.
D770,470 S 11/2016 Jin
9,520,887 B1 12/2016 Zhuang et al.
D780,768 S 3/2017 Carlson et al.
9,592,358 B2 3/2017 Miller et al.
9,592,385 B2 3/2017 Kaula et al.
9,597,517 B2 3/2017 Moffitt
D783,032 S 4/2017 Cashner et al.
9,610,442 B2 4/2017 Yoo et al.
D788,134 S 5/2017 Wong et al.
9,639,982 B2 5/2017 Craik et al.
9,656,076 B2 5/2017 Trier et al.
D789,963 S 6/2017 Agashiwala et al.
D794,667 S 8/2017 Havaldar et al.
9,717,908 B2 8/2017 Karunasiri
9,724,513 B2 8/2017 Lane et al.
9,802,052 B2 10/2017 Marnfeldt
9,812,875 B2 11/2017 Nejatali et al.
D806,717 S 1/2018 Bae et al.
9,895,545 B2 2/2018 Rao et al.
D816,708 S 5/2018 Riedel et al.

(56) References Cited

U.S. PATENT DOCUMENTS

D819,681 S 6/2018 Fung et al.
9,993,642 B2 6/2018 Gerasimenko et al.
10,092,750 B2 10/2018 Edgerton et al.
D834,601 S 11/2018 Felt
10,124,166 B2 11/2018 Edgerton et al.
10,137,299 B2 11/2018 Lu et al.
D839,278 S 1/2019 Carlson et al.
D839,914 S 2/2019 Lee et al.
D841,017 S 2/2019 Bathla
D843,388 S 3/2019 Protzman et al.
10,406,366 B2 9/2019 Westlund et al.
10,449,371 B2 10/2019 Serrano Carmona
D874,491 S 2/2020 Kuo et al.
D874,507 S 2/2020 Martell et al.
D875,108 S 2/2020 Chitalia et al.
D875,752 S 2/2020 Nelson et al.
D877,753 S 3/2020 Chitalia et al.
10,751,533 B2 8/2020 Edgerton et al.
10,758,732 B1 9/2020 Heldman
10,773,074 B2 9/2020 Liu et al.
10,799,701 B2 10/2020 Lee
10,806,927 B2 10/2020 Edgerton et al.
10,806,935 B2 10/2020 Rao et al.
D904,437 S 12/2020 Chitalia et al.
D905,701 S 12/2020 Feng et al.
10,881,853 B2 1/2021 Edgerton et al.
10,898,719 B2 1/2021 Pivonka et al.
D912,074 S 3/2021 Giannino et al.
D926,784 S 8/2021 Carlson et al.
D928,188 S 8/2021 Giannino et al.
11,097,122 B2 8/2021 Lu
11,123,312 B2 9/2021 Lu et al.
11,129,983 B2 9/2021 Lo et al.
D939,549 S 12/2021 Miyai et al.
D947,216 S 3/2022 Leininger
11,266,850 B2 3/2022 Prouza et al.
11,298,533 B2 4/2022 Edgerton et al.
D962,245 S 8/2022 Thompson et al.
11,400,284 B2 8/2022 Gerasimenko et al.
11,491,336 B2 11/2022 Scheltienne et al.
11,511,116 B2 11/2022 Wagner et al.
11,515,733 B2 11/2022 Babakhani et al.
11,638,820 B2 5/2023 Edgerton et al.
11,684,774 B2 6/2023 Crosby et al.
11,691,015 B2 7/2023 Minassian et al.
D1,008,290 S 12/2023 Stapfer
D1,008,291 S 12/2023 Stapfer
D1,010,666 S 1/2024 Cai et al.
11,911,621 B2 2/2024 Ganty et al.
11,944,814 B2 4/2024 Lo et al.
11,957,910 B2 4/2024 Edgerton et al.
11,986,653 B2 5/2024 Lo et al.
11,992,684 B2 5/2024 Minassian et al.
12,018,135 B2 6/2024 Scher et al.
12,023,492 B2 7/2024 Edgerton et al.
12,076,301 B2 9/2024 Lu et al.
D1,044,827 S 10/2024 Tabrizi et al.
12,201,833 B2 1/2025 Edgerton et al.
12,214,198 B2 2/2025 Bennett et al.
12,268,878 B2 4/2025 Phillips et al.
12,415,079 B2 9/2025 Scheltienne et al.
2001/0016266 A1 8/2001 Okazaki et al.
2001/0032992 A1 10/2001 Wendt
2002/0042814 A1 4/2002 Fukasawa et al.
2002/0050456 A1 5/2002 Sheppard, Jr. et al.
2002/0052539 A1 5/2002 Haller et al.
2002/0055779 A1 5/2002 Andrews
2002/0083240 A1 6/2002 Hoese et al.
2002/0111661 A1 8/2002 Cross et al.
2002/0115945 A1 8/2002 Herman et al.
2002/0123672 A1 9/2002 Christophersom et al.
2002/0138512 A1 9/2002 Buresh et al.
2002/0173505 A1 11/2002 Skogvall
2002/0175931 A1 11/2002 Holtz et al.
2002/0187260 A1 12/2002 Sheppard, Jr. et al.
2002/0188332 A1 12/2002 Lurie et al.
2002/0193843 A1 12/2002 Hill et al.
2003/0032992 A1 2/2003 Thacker et al.
2003/0078633 A1 4/2003 Firlik et al.
2003/0093021 A1 5/2003 Goffer
2003/0093131 A1 5/2003 Loeb et al.
2003/0097166 A1 5/2003 Krulevitch et al.
2003/0100933 A1 5/2003 Ayal et al.
2003/0113725 A1 6/2003 Small et al.
2003/0114894 A1 6/2003 Dar et al.
2003/0114899 A1 6/2003 Woods et al.
2003/0135253 A1 7/2003 Kokones et al.
2003/0139422 A1 7/2003 Teng
2003/0145759 A1 8/2003 Rodnunsky
2003/0158583 A1 8/2003 Burnett et al.
2003/0199116 A1 10/2003 Tai et al.
2003/0200323 A1 10/2003 Dold et al.
2003/0208248 A1 11/2003 Carter et al.
2003/0220679 A1 11/2003 Han
2003/0233137 A1 12/2003 Paul, Jr.
2004/0039425 A1 2/2004 Greenwood-Van Meerveld
2004/0044380 A1 3/2004 Bruninga et al.
2004/0082979 A1 4/2004 Tong et al.
2004/0087286 A1 5/2004 Inoue et al.
2004/0088015 A1 5/2004 Casavant et al.
2004/0111118 A1 6/2004 Hill et al.
2004/0111126 A1 6/2004 Tanagho et al.
2004/0121528 A1 6/2004 Krulevitch et al.
2004/0122483 A1 6/2004 Nathan et al.
2004/0127954 A1 7/2004 McDonald
2004/0133248 A1 7/2004 Frei et al.
2004/0138518 A1 7/2004 Rise et al.
2004/0147975 A1 7/2004 Popovic et al.
2004/0172027 A1 9/2004 Speitling et al.
2004/0172097 A1 9/2004 Brodard et al.
2004/0181263 A1 9/2004 Balzer et al.
2004/0192082 A1 9/2004 Wagner et al.
2004/0192834 A1 9/2004 Nakayoshi et al.
2004/0243204 A1 12/2004 Maghribi et al.
2004/0267320 A1 12/2004 Taylor et al.
2005/0004622 A1 1/2005 Cullen et al.
2005/0043775 A1 2/2005 John et al.
2005/0061315 A1 3/2005 Lee et al.
2005/0070982 A1 3/2005 Heruth et al.
2005/0075662 A1 4/2005 Pedersen et al.
2005/0075669 A1 4/2005 King
2005/0075678 A1 4/2005 Faul
2005/0075693 A1 4/2005 Toy et al.
2005/0080460 A1 4/2005 Wang et al.
2005/0090756 A1 4/2005 Wolf et al.
2005/0101827 A1 5/2005 Delisle
2005/0102007 A1 5/2005 Ayal et al.
2005/0113878 A1 5/2005 Gerber
2005/0113882 A1 5/2005 Cameron et al.
2005/0119713 A1 6/2005 Whitehurst et al.
2005/0125045 A1 6/2005 Brighton et al.
2005/0203588 A1 9/2005 King
2005/0205961 A1 9/2005 Doong
2005/0209655 A1 9/2005 Bradley et al.
2005/0231186 A1 10/2005 Saavedra Barrera et al.
2005/0239612 A1 10/2005 Keiser
2005/0246004 A1 11/2005 Cameron et al.
2005/0253273 A1 11/2005 Tai et al.
2005/0277999 A1 12/2005 Strother et al.
2005/0278000 A1 12/2005 Strother et al.
2006/0003090 A1 1/2006 Rodger et al.
2006/0007983 A1 1/2006 Tai et al.
2006/0015153 A1 1/2006 Gliner et al.
2006/0015470 A1 1/2006 Lauer et al.
2006/0016266 A1 1/2006 Weise et al.
2006/0018360 A1 1/2006 Tai et al.
2006/0041225 A1 2/2006 Wallace et al.
2006/0041295 A1 2/2006 Osypka
2006/0047325 A1 3/2006 Thimineur et al.
2006/0075339 A1 4/2006 Tomita et al.
2006/0082626 A1 4/2006 Oikawa et al.
2006/0089696 A1 4/2006 Olsen et al.
2006/0095088 A1 5/2006 De Ridder
2006/0100671 A1 5/2006 Ridder

(56) References Cited

U.S. PATENT DOCUMENTS

2006/0111754 A1 5/2006 Rezai et al.
2006/0122678 A1 6/2006 Olsen et al.
2006/0142337 A1 6/2006 Ikeura et al.
2006/0142816 A1 6/2006 Fruitman et al.
2006/0142822 A1 6/2006 Tulgar
2006/0149333 A1 7/2006 Tanagho et al.
2006/0149337 A1 7/2006 John
2006/0189453 A1 8/2006 Leblond
2006/0189839 A1 8/2006 Laniado et al.
2006/0195153 A1 8/2006 Diubaldi et al.
2006/0239482 A1 10/2006 Hatoum
2006/0241356 A1 10/2006 Flaherty
2006/0282127 A1 12/2006 Zealear
2007/0004567 A1 1/2007 Shetty et al.
2007/0009968 A1 1/2007 Cunningham et al.
2007/0016097 A1 1/2007 Farquhar et al.
2007/0016266 A1 1/2007 Paul, Jr.
2007/0016268 A1 1/2007 Carter et al.
2007/0016329 A1 1/2007 Herr et al.
2007/0021513 A1 1/2007 Agee et al.
2007/0027495 A1 2/2007 Gerber
2007/0047852 A1 3/2007 Sharp et al.
2007/0049814 A1 3/2007 Muccio
2007/0055318 A1 3/2007 Forsberg et al.
2007/0055337 A1 3/2007 Tanrisever
2007/0060954 A1 3/2007 Cameron et al.
2007/0060980 A1 3/2007 Strother et al.
2007/0067003 A1 3/2007 Sanchez et al.
2007/0073357 A1 3/2007 Rooney et al.
2007/0083240 A1 4/2007 Peterson et al.
2007/0100389 A1 5/2007 Jaax et al.
2007/0121702 A1 5/2007 Laguardia et al.
2007/0121709 A1 5/2007 Ittogi
2007/0129769 A1 6/2007 Bourget et al.
2007/0142874 A1 6/2007 John
2007/0142878 A1 6/2007 Krulevitch et al.
2007/0150023 A1 6/2007 Ignagni et al.
2007/0150034 A1 6/2007 Rooney et al.
2007/0156172 A1 7/2007 Alvarado
2007/0156179 A1 7/2007 S.E.
2007/0156200 A1 7/2007 Kornet et al.
2007/0168008 A1 7/2007 Olsen
2007/0179534 A1 8/2007 Firlik et al.
2007/0179579 A1 8/2007 Feler et al.
2007/0191709 A1 8/2007 Swanson
2007/0208381 A1 9/2007 Hill et al.
2007/0233204 A1 10/2007 Lima et al.
2007/0250119 A1 10/2007 Tyler et al.
2007/0255372 A1 11/2007 Metzler et al.
2007/0265621 A1 11/2007 Matthis et al.
2007/0265679 A1 11/2007 Bradley et al.
2007/0265691 A1 11/2007 Swanson
2007/0276449 A1 11/2007 Gunter et al.
2007/0276450 A1 11/2007 Meadows et al.
2007/0282378 A1 12/2007 Huang et al.
2007/0293910 A1 12/2007 Strother et al.
2008/0002227 A1 1/2008 Tsujimoto
2008/0004674 A1 1/2008 King et al.
2008/0009927 A1 1/2008 Vilims
2008/0021513 A1 1/2008 Thacker et al.
2008/0027346 A1 1/2008 Litt et al.
2008/0046049 A1 2/2008 Skubitz et al.
2008/0051851 A1 2/2008 Lin
2008/0071325 A1 3/2008 Bradley
2008/0077192 A1 3/2008 Harry et al.
2008/0092911 A1 4/2008 Schulman et al.
2008/0103579 A1 5/2008 Gerber
2008/0105185 A1 5/2008 Kuhlman
2008/0127031 A1 5/2008 Olsson et al.
2008/0140152 A1 6/2008 Imran et al.
2008/0140162 A1 6/2008 Goetz et al.
2008/0140169 A1 6/2008 Imran
2008/0147143 A1 6/2008 Popovic et al.
2008/0154329 A1 6/2008 Pyles et al.
2008/0183097 A1 7/2008 Leyde et al.
2008/0183224 A1 7/2008 Barolat
2008/0200749 A1 8/2008 Zheng et al.
2008/0202940 A1 8/2008 Jiang et al.
2008/0207985 A1 8/2008 Farone
2008/0208287 A1 8/2008 Palermo et al.
2008/0215113 A1 9/2008 Pawlowicz
2008/0221653 A1 9/2008 Agrawal et al.
2008/0224226 A1 9/2008 Suzuki et al.
2008/0228241 A1 9/2008 Sachs
2008/0228250 A1 9/2008 Mironer
2008/0234121 A1 9/2008 Kim et al.
2008/0234791 A1 9/2008 Arle et al.
2008/0255582 A1 10/2008 Harris
2008/0269854 A1 10/2008 Hegland et al.
2008/0275129 A1 11/2008 Lundstedt et al.
2008/0279896 A1 11/2008 Heinen et al.
2008/0287268 A1 11/2008 Hidler
2008/0294211 A1 11/2008 Moffitt
2008/0294226 A1 11/2008 Moffitt et al.
2008/0318733 A1 12/2008 Osler-Weppenaar
2009/0005844 A1 1/2009 Swoyer et al.
2009/0012436 A1 1/2009 Lanfermann et al.
2009/0024186 A1 1/2009 Brockway
2009/0024997 A1 1/2009 Kobayashi
2009/0093854 A1 4/2009 Leung et al.
2009/0112281 A1 4/2009 Miyazawa et al.
2009/0118365 A1 5/2009 Benson, III et al.
2009/0131995 A1 5/2009 Sloan et al.
2009/0157141 A1 6/2009 Chiao et al.
2009/0198305 A1 8/2009 Naroditsky et al.
2009/0204173 A1 8/2009 Fang et al.
2009/0227925 A1 9/2009 Mcbean et al.
2009/0229166 A1 9/2009 Sawrie
2009/0254151 A1 10/2009 Anderson et al.
2009/0270960 A1 10/2009 Zhao et al.
2009/0281529 A1 11/2009 Carriazo
2009/0281599 A1 11/2009 Thacker et al.
2009/0293270 A1 12/2009 Brindley et al.
2009/0299166 A1 12/2009 Nishida et al.
2009/0299167 A1 12/2009 Seymour
2009/0306491 A1 12/2009 Haggers
2009/0312165 A1 12/2009 Rempe
2010/0004715 A1 1/2010 Fahey
2010/0006737 A1 1/2010 Colombo et al.
2010/0008782 A1 1/2010 Danescu et al.
2010/0010646 A1 1/2010 Drew et al.
2010/0016732 A1 1/2010 Wells et al.
2010/0023069 A1 1/2010 Moffitt et al.
2010/0023070 A1 1/2010 Moffitt et al.
2010/0023103 A1 1/2010 Elborno
2010/0029040 A1 2/2010 Nomoto
2010/0042193 A1 2/2010 Slavin
2010/0048358 A1 2/2010 Tchao et al.
2010/0057177 A1 3/2010 Moffitt et al.
2010/0063568 A1 3/2010 Staunton et al.
2010/0070007 A1 3/2010 Parker et al.
2010/0070010 A1 3/2010 Simpson
2010/0087782 A1 4/2010 Ghaffari et al.
2010/0094800 A1 4/2010 Sharp
2010/0114205 A1 5/2010 Donofrio et al.
2010/0114239 A1 5/2010 Mcdonald, III
2010/0116526 A1 5/2010 Arora et al.
2010/0125313 A1 5/2010 Lee et al.
2010/0137238 A1 6/2010 Gan et al.
2010/0137938 A1 6/2010 Kishawi et al.
2010/0137943 A1 6/2010 Zhu
2010/0145428 A1 6/2010 Cameron et al.
2010/0152811 A1 6/2010 Flaherty
2010/0166546 A1 7/2010 Mahan et al.
2010/0168820 A1 7/2010 Maniak et al.
2010/0179562 A1 7/2010 Linker et al.
2010/0185253 A1 7/2010 Dimarco et al.
2010/0191307 A1 7/2010 Fang et al.
2010/0198298 A1 8/2010 Glukhovsky et al.
2010/0217355 A1 8/2010 Tass et al.
2010/0217418 A1 8/2010 Fontanot
2010/0228310 A1 9/2010 Shuros et al.
2010/0241121 A1 9/2010 Logan et al.
2010/0241191 A1 9/2010 Testerman et al.

(56) References Cited

U.S. PATENT DOCUMENTS

2010/0268299 A1 10/2010 Farone
2010/0274312 A1 10/2010 Alataris et al.
2010/0279606 A1 11/2010 Hillan et al.
2010/0280570 A1 11/2010 Sturm et al.
2010/0298905 A1 11/2010 Simon
2010/0298910 A1 11/2010 Carbunaru et al.
2010/0305660 A1 12/2010 Hegi et al.
2010/0312304 A1 12/2010 York et al.
2010/0318168 A1 12/2010 Bighetti
2010/0324699 A1 12/2010 Herr et al.
2010/0331925 A1 12/2010 Peterson
2011/0006793 A1 1/2011 Peschke et al.
2011/0009919 A1 1/2011 Carbunaru et al.
2011/0016081 A1 1/2011 Basak et al.
2011/0029040 A1 2/2011 Walker et al.
2011/0029044 A1 2/2011 Hyde et al.
2011/0034277 A1 2/2011 Brandes
2011/0034912 A1 2/2011 De Graff et al.
2011/0034977 A1 2/2011 Janik et al.
2011/0040349 A1 2/2011 Graupe
2011/0054567 A1 3/2011 Lane et al.
2011/0054568 A1* 3/2011 Lane .................. A61N 1/36082 607/59
2011/0054570 A1 3/2011 Lane
2011/0054579 A1 3/2011 Kumar et al.
2011/0060461 A1 3/2011 Velliste et al.
2011/0077660 A1 3/2011 Janik et al.
2011/0082515 A1 4/2011 Libbus et al.
2011/0084489 A1 4/2011 Kaplan
2011/0093043 A1 4/2011 Torgerson et al.
2011/0112601 A1 5/2011 Meadows et al.
2011/0112611 A1 5/2011 Aghassian
2011/0118815 A1 5/2011 Kuzma et al.
2011/0125203 A1 5/2011 Simon et al.
2011/0130804 A1 6/2011 Lin et al.
2011/0152967 A1 6/2011 Simon et al.
2011/0160810 A1* 6/2011 Griffith .............. A61N 1/37241 607/72
2011/0166546 A1 7/2011 Jaax et al.
2011/0184482 A1 7/2011 Eberman et al.
2011/0184488 A1 7/2011 De Ridder
2011/0184489 A1 7/2011 Nicolelis et al.
2011/0201944 A1 8/2011 Higgins et al.
2011/0202107 A1 8/2011 Sunagawa et al.
2011/0208265 A1 8/2011 Erickson et al.
2011/0213266 A1 9/2011 Williams et al.
2011/0218590 A1 9/2011 Degiorgio et al.
2011/0218594 A1 9/2011 Doron et al.
2011/0224153 A1 9/2011 Levitt et al.
2011/0224665 A1 9/2011 Crosby et al.
2011/0224752 A1 9/2011 Rolston et al.
2011/0224753 A1 9/2011 Palermo et al.
2011/0224755 A1 9/2011 Arie et al.
2011/0224757 A1 9/2011 Zdeblick et al.
2011/0230101 A1 9/2011 Tang et al.
2011/0230701 A1 9/2011 Simon et al.
2011/0230702 A1 9/2011 Honour
2011/0230747 A1 9/2011 Rogers et al.
2011/0230808 A1 9/2011 Lisowski
2011/0231326 A1 9/2011 Marino
2011/0237221 A1 9/2011 Prakash et al.
2011/0237921 A1 9/2011 Askin et al.
2011/0245734 A1 10/2011 Wagner et al.
2011/0260126 A1 10/2011 Willis
2011/0270360 A1 11/2011 Harris et al.
2011/0276107 A1 11/2011 Simon et al.
2011/0288609 A1 11/2011 Tehrani et al.
2011/0295100 A1 12/2011 Hegde et al.
2012/0006793 A1 1/2012 Swanson
2012/0011222 A1 1/2012 Yasukawa et al.
2012/0011950 A1 1/2012 Kracke
2012/0013041 A1 1/2012 Cao et al.
2012/0013126 A1 1/2012 Molloy
2012/0016448 A1 1/2012 Lee
2012/0016453 A1 1/2012 Feler et al.
2012/0018249 A1 1/2012 Mehr
2012/0022371 A1 1/2012 Summerton
2012/0022551 A1 1/2012 Staunton et al.
2012/0029528 A1 2/2012 Macdonald et al.
2012/0035684 A1 2/2012 Thompson et al.
2012/0036552 A1 2/2012 Dare et al.
2012/0041518 A1 2/2012 Kim et al.
2012/0052432 A1 3/2012 Matsuura
2012/0053645 A1 3/2012 Ayanoor-Vitikkate et al.
2012/0059432 A1 3/2012 Emborg et al.
2012/0071250 A1 3/2012 O'Neil et al.
2012/0071950 A1 3/2012 Archer
2012/0083709 A1 4/2012 Parker et al.
2012/0101326 A1 4/2012 Simon et al.
2012/0109251 A1 5/2012 Lebedev et al.
2012/0109295 A1 5/2012 Fan
2012/0116476 A1 5/2012 Kothandaraman
2012/0116478 A1 5/2012 Buhlmann et al.
2012/0123223 A1 5/2012 Freeman et al.
2012/0123293 A1 5/2012 Shah et al.
2012/0126392 A1 5/2012 Kalvesten et al.
2012/0136408 A1 5/2012 Grill et al.
2012/0143281 A1 6/2012 Birkill et al.
2012/0161531 A1 6/2012 Kim
2012/0161721 A1 6/2012 Neethimanickam
2012/0165899 A1 6/2012 Gliner
2012/0168397 A1 7/2012 Lim et al.
2012/0172222 A1 7/2012 Artigas Puerto
2012/0172246 A1 7/2012 Nguyen et al.
2012/0172510 A1 7/2012 Esseghir et al.
2012/0172946 A1 7/2012 Alataris et al.
2012/0179222 A1 7/2012 Jaax et al.
2012/0185020 A1 7/2012 Simon et al.
2012/0197338 A1 8/2012 Su et al.
2012/0203055 A1 8/2012 Pletnev
2012/0203131 A1 8/2012 Dilorenzo
2012/0203246 A1 8/2012 Staunton et al.
2012/0221073 A1 8/2012 Southwell et al.
2012/0232615 A1 9/2012 Barolat et al.
2012/0252380 A1 10/2012 Kawakita
2012/0252874 A1 10/2012 Feinstein et al.
2012/0259380 A1 10/2012 Pyles
2012/0265269 A1 10/2012 Lui
2012/0271315 A1 10/2012 Pianca et al.
2012/0271372 A1 10/2012 Osorio
2012/0277824 A1 11/2012 Li
2012/0277834 A1 11/2012 Mercanzini et al.
2012/0283697 A1 11/2012 Kim et al.
2012/0283797 A1 11/2012 De Ridder
2012/0302821 A1 11/2012 Burnett
2012/0310302 A1 12/2012 Bennett et al.
2012/0310305 A1 12/2012 Kaula et al.
2012/0310315 A1 12/2012 Savage et al.
2012/0330321 A1 12/2012 Johnson et al.
2012/0330391 A1 12/2012 Bradley et al.
2013/0006322 A1 1/2013 Tai
2013/0006793 A1 1/2013 O'Sullivan et al.
2013/0012853 A1 1/2013 Brown
2013/0013041 A1 1/2013 Glukhovsky et al.
2013/0023972 A1 1/2013 Kuzma et al.
2013/0026640 A1 1/2013 Ito et al.
2013/0030312 A1 1/2013 Keel et al.
2013/0030319 A1 1/2013 Hettrick et al.
2013/0030501 A1 1/2013 Feler et al.
2013/0032508 A1 2/2013 Azuma
2013/0035745 A1 2/2013 Ahmed et al.
2013/0041235 A1 2/2013 Rogers et al.
2013/0053734 A1 2/2013 Barriskill et al.
2013/0053922 A1 2/2013 Ahmed et al.
2013/0066392 A1 3/2013 Simon et al.
2013/0066411 A1 3/2013 Thacker et al.
2013/0085317 A1 4/2013 Feinstein
2013/0085361 A1 4/2013 Mercanzini et al.
2013/0096640 A1 4/2013 Passover
2013/0096661 A1 4/2013 Greenberg et al.
2013/0096662 A1 4/2013 Swanson
2013/0110196 A1 5/2013 Alataris et al.
2013/0116604 A1 5/2013 Marilla et al.
2013/0116751 A1 5/2013 Moffitt et al.

(56) References Cited

U.S. PATENT DOCUMENTS

2013/0123568 A1 5/2013 Hamilton et al.
2013/0123659 A1 5/2013 Bartol et al.
2013/0138167 A1 5/2013 Bradley et al.
2013/0150915 A1 6/2013 Kane et al.
2013/0154373 A1 6/2013 Lisuwandi et al.
2013/0158444 A1 6/2013 Herr et al.
2013/0165991 A1 6/2013 Kim et al.
2013/0190143 A1 7/2013 Greenhill et al.
2013/0197408 A1 8/2013 Goldfarb et al.
2013/0204324 A1 8/2013 Thacker et al.
2013/0211477 A1 8/2013 Cullen et al.
2013/0226263 A1 8/2013 Kelly et al.
2013/0237948 A1 9/2013 Donders et al.
2013/0245712 A1 9/2013 Simon et al.
2013/0253222 A1 9/2013 Nakao
2013/0253229 A1 9/2013 Sawant et al.
2013/0253299 A1 9/2013 Weber et al.
2013/0253611 A1 9/2013 Lee et al.
2013/0268016 A1 10/2013 Xi et al.
2013/0268020 A1 10/2013 Rosenberg et al.
2013/0268021 A1 10/2013 Moffitt
2013/0268041 A1 10/2013 Schulte et al.
2013/0281890 A1 10/2013 Mishelevich
2013/0289446 A1 10/2013 Stone et al.
2013/0289650 A1 10/2013 Karlsson et al.
2013/0289664 A1 10/2013 Johanek
2013/0289667 A1 10/2013 Wacnik et al.
2013/0296965 A1 11/2013 Mokelke et al.
2013/0303873 A1 11/2013 Voros et al.
2013/0304159 A1 11/2013 Simon et al.
2013/0310211 A1 11/2013 Wilton et al.
2013/0310911 A1 11/2013 Tai et al.
2013/0325081 A1 12/2013 Karst et al.
2013/0325083 A1 12/2013 Bharmi et al.
2013/0345780 A1 12/2013 Tabada et al.
2014/0005753 A1 1/2014 Carbunaru
2014/0031893 A1 1/2014 Walker et al.
2014/0031895 A1 1/2014 Rahimi et al.
2014/0046407 A1 2/2014 Ben-Ezra et al.
2014/0053401 A1 2/2014 Kuzma et al.
2014/0058292 A1 2/2014 Alford et al.
2014/0058490 A1 2/2014 Dimarco
2014/0059499 A1 2/2014 Kim et al.
2014/0066950 A1 3/2014 Macdonald et al.
2014/0067007 A1 3/2014 Drees et al.
2014/0067013 A1 3/2014 Kaula et al.
2014/0067354 A1 3/2014 Kaula et al.
2014/0074190 A1 3/2014 Griffith
2014/0081011 A1 3/2014 Vaught et al.
2014/0081071 A1 3/2014 Simon et al.
2014/0081345 A1 3/2014 Hershey
2014/0087922 A1 3/2014 Bayerlein et al.
2014/0088674 A1 3/2014 Bradley
2014/0100491 A1 4/2014 Hu et al.
2014/0100633 A1 4/2014 Mann et al.
2014/0107397 A1 4/2014 Simon et al.
2014/0107398 A1 4/2014 Simon et al.
2014/0114374 A1 4/2014 Rooney et al.
2014/0114385 A1 4/2014 Nijhuis et al.
2014/0124713 A1 5/2014 Majumdar et al.
2014/0142652 A1 5/2014 Francois et al.
2014/0163640 A1 6/2014 Edgerton et al.
2014/0171961 A1 6/2014 Lacey et al.
2014/0172045 A1 6/2014 Yip et al.
2014/0172055 A1 6/2014 Venancio
2014/0180361 A1 6/2014 Burdick et al.
2014/0200387 A1 7/2014 Ahmed
2014/0201905 A1 7/2014 Glukhovsky
2014/0213842 A1 7/2014 Simon et al.
2014/0213844 A1 7/2014 Pilla et al.
2014/0228905 A1 8/2014 Bolea
2014/0236257 A1 8/2014 Parker et al.
2014/0243923 A1 8/2014 Doan et al.
2014/0257016 A1 9/2014 Ahmed
2014/0277271 A1 9/2014 Chan et al.
2014/0296752 A1 10/2014 Edgerton et al.
2014/0303685 A1 10/2014 Rosenberg et al.
2014/0303901 A1 10/2014 Sadeh
2014/0316484 A1 10/2014 Edgerton et al.
2014/0316503 A1 10/2014 Tai et al.
2014/0324118 A1 10/2014 Simon et al.
2014/0330067 A1 11/2014 Jordan
2014/0330335 A1 11/2014 Errico et al.
2014/0336722 A1 11/2014 Rocon De Lima et al.
2014/0339909 A1 11/2014 Sugawara
2014/0343623 A1 11/2014 Alves et al.
2014/0344740 A1 11/2014 Kaula et al.
2014/0357936 A1 12/2014 Simon et al.
2014/0359521 A1 12/2014 Lin et al.
2014/0371830 A1 12/2014 Howard et al.
2015/0005167 A1 1/2015 Jung et al.
2015/0005840 A1 1/2015 Pal et al.
2015/0012061 A1 1/2015 Chen
2015/0022143 A1 1/2015 Kim
2015/0032187 A1 1/2015 Ranu et al.
2015/0051674 A1 2/2015 Barner et al.
2015/0057717 A1 2/2015 Wu et al.
2015/0065559 A1 3/2015 Feinstein et al.
2015/0066111 A1 3/2015 Blum et al.
2015/0074997 A1 3/2015 Kuzma et al.
2015/0088212 A1 3/2015 De Ridder
2015/0094734 A1 4/2015 Staunton et al.
2015/0094791 A1 4/2015 Edgell et al.
2015/0120634 A1 4/2015 Tateno
2015/0126120 A1 5/2015 Chen
2015/0148878 A1 5/2015 Yoo et al.
2015/0151114 A1 6/2015 Black et al.
2015/0151126 A1 6/2015 Kishawi et al.
2015/0165226 A1 6/2015 Simon et al.
2015/0174411 A1* 6/2015 Ranu .................... A61N 1/3615 607/72
2015/0182784 A1 7/2015 Barriskill et al.
2015/0188592 A1 7/2015 Solondz
2015/0190200 A1 7/2015 Courtine et al.
2015/0190634 A1 7/2015 Rezai et al.
2015/0196231 A1 7/2015 Ziaie et al.
2015/0196241 A1 7/2015 Yekutieli
2015/0200561 A1 7/2015 Lee et al.
2015/0217120 A1 8/2015 Nandra et al.
2015/0224326 A1 8/2015 Toth et al.
2015/0231326 A1 8/2015 Milner et al.
2015/0231396 A1 8/2015 Burdick et al.
2015/0246216 A1 9/2015 Barker
2015/0265830 A1 9/2015 Simon et al.
2015/0268845 A1 9/2015 Endo
2015/0320632 A1 11/2015 Vallery et al.
2015/0328462 A1 11/2015 Griffith
2015/0343199 A1 12/2015 Wechter et al.
2015/0343205 A1 12/2015 Howard et al.
2016/0001096 A1 1/2016 Mishelevich
2016/0005538 A1 1/2016 Koyanagi et al.
2016/0030737 A1 2/2016 Gerasimenko et al.
2016/0030748 A1 2/2016 Edgerton et al.
2016/0030750 A1 2/2016 Bokil et al.
2016/0045727 A1 2/2016 Rezai et al.
2016/0045731 A1 2/2016 Simon et al.
2016/0067477 A1 3/2016 Dubuclet
2016/0074663 A1 3/2016 De Ridder
2016/0082261 A1 3/2016 Moffitt et al.
2016/0121109 A1 5/2016 Edgerton et al.
2016/0121114 A1 5/2016 Simon et al.
2016/0121116 A1 5/2016 Simon et al.
2016/0121121 A1 5/2016 Mashiach
2016/0136477 A1 5/2016 Bucher et al.
2016/0143588 A1 5/2016 Hoitink et al.
2016/0144167 A1 5/2016 Bakker et al.
2016/0144184 A1 5/2016 Marnfeldt
2016/0157389 A1 6/2016 Hwang
2016/0166828 A1 6/2016 Yu
2016/0175586 A1 6/2016 Edgerton et al.
2016/0197488 A1 7/2016 Hada et al.
2016/0213918 A1 7/2016 Howard et al.
2016/0220813 A1 8/2016 Edgerton et al.
2016/0228706 A1 8/2016 Hershey et al.

(56) References Cited

U.S. PATENT DOCUMENTS

2016/0235977 A1 8/2016 Lu et al.
2016/0250461 A1 9/2016 Dubuclet
2016/0263376 A1 9/2016 Yoo et al.
2016/0271413 A1 9/2016 Vallejo et al.
2016/0279418 A1 9/2016 Courtine et al.
2016/0279429 A1 9/2016 Hershey et al.
2016/0291848 A1 10/2016 Hall et al.
2016/0310739 A1 10/2016 Burdick et al.
2016/0339239 A1 11/2016 Yoo et al.
2016/0367827 A1 12/2016 Tahmasian
2017/0007320 A1 1/2017 Levin et al.
2017/0007831 A1 1/2017 Edgerton et al.
2017/0014620 A9 1/2017 Staunton et al.
2017/0014622 A1 1/2017 Bozung et al.
2017/0065814 A1 3/2017 Howard et al.
2017/0079598 A1 3/2017 Stolen et al.
2017/0098951 A1 4/2017 Olgun et al.
2017/0098962 A1 4/2017 Desrosiers
2017/0118722 A1 4/2017 Hong et al.
2017/0128729 A1 5/2017 Netoff et al.
2017/0156662 A1 6/2017 Goodall et al.
2017/0157389 A1 6/2017 Tai et al.
2017/0157396 A1 6/2017 Dixon et al.
2017/0161454 A1 6/2017 Grill et al.
2017/0165497 A1 6/2017 Lu
2017/0173326 A1 6/2017 Bloch et al.
2017/0189686 A1 7/2017 Steinke et al.
2017/0239486 A1 8/2017 Suryavanshi
2017/0246450 A1 8/2017 Liu et al.
2017/0246452 A1 8/2017 Liu et al.
2017/0266455 A1 9/2017 Steinke
2017/0274209 A1 9/2017 Edgerton et al.
2017/0291023 A1 10/2017 Kuzma et al.
2017/0296837 A1 10/2017 Jin
2017/0338570 A1 11/2017 Myers
2017/0348523 A1 12/2017 Rubehn et al.
2017/0348532 A1 12/2017 Moffitt et al.
2017/0354819 A1 12/2017 Bloch et al.
2017/0361093 A1 12/2017 Yoo et al.
2017/0361115 A1 12/2017 Aghassian et al.
2018/0008826 A1 1/2018 Dimarco
2018/0028812 A1 2/2018 Vallejo et al.
2018/0056078 A1 3/2018 Kashyap et al.
2018/0083473 A1 3/2018 Menegoli et al.
2018/0085582 A1 3/2018 Calle et al.
2018/0085583 A1 3/2018 Zhang et al.
2018/0093093 A1 4/2018 Courtine et al.
2018/0104479 A1 4/2018 Grill et al.
2018/0110992 A1 4/2018 Parramon et al.
2018/0117334 A1 5/2018 Jung
2018/0125416 A1 5/2018 Schwarz et al.
2018/0125419 A1 5/2018 Yun et al.
2018/0126154 A1 5/2018 Dubuclet
2018/0126155 A1 5/2018 Mclaughlin et al.
2018/0133480 A1 5/2018 Annoni et al.
2018/0133481 A1 5/2018 Von Zitzewitz et al.
2018/0153474 A1 6/2018 Aeschlimann et al.
2018/0178008 A1 6/2018 Bouton et al.
2018/0185632 A1 7/2018 Staunton et al.
2018/0185642 A1 7/2018 Lu
2018/0185648 A1 7/2018 Nandra et al.
2018/0193655 A1 7/2018 Zhang et al.
2018/0214694 A1 8/2018 Parramon
2018/0221620 A1 8/2018 Metzger
2018/0221651 A1 8/2018 Chang et al.
2018/0228421 A1 8/2018 Saab
2018/0229037 A1 8/2018 Edgerton et al.
2018/0229038 A1 8/2018 Burdick et al.
2018/0236240 A1 8/2018 Harkema et al.
2018/0256906 A1 9/2018 Pivonka et al.
2018/0272125 A1 9/2018 Sandhu
2018/0272132 A1 9/2018 Subbaroyan et al.
2018/0280693 A1 10/2018 Edgerton et al.
2018/0280706 A1 10/2018 Maile et al.
2018/0289971 A1 10/2018 Yeh et al.
2018/0294547 A1 10/2018 Park et al.
2018/0318576 A1 11/2018 Bozung et al.
2018/0326220 A1 11/2018 Kaula et al.
2018/0337547 A1 11/2018 Menegoli et al.
2018/0353755 A1 12/2018 Edgerton et al.
2018/0361146 A1 12/2018 Gerasimenko et al.
2018/0367187 A1 12/2018 Mcfarthing
2018/0369574 A1 12/2018 Dubuclet et al.
2018/0369575 A1 12/2018 Dubuclet et al.
2018/0369576 A1 12/2018 Dubuclet et al.
2019/0001122 A1 1/2019 Ganty et al.
2019/0001139 A1 1/2019 Mishra et al.
2019/0009094 A1 1/2019 Zhang et al.
2019/0017983 A1 1/2019 Smith
2019/0022371 A1 1/2019 Chang et al.
2019/0027257 A1 1/2019 Ghogawala
2019/0033622 A1 1/2019 Olgun et al.
2019/0160294 A1 5/2019 Peterson et al.
2019/0167980 A1 6/2019 Peterson
2019/0167987 A1 6/2019 Lu et al.
2019/0192852 A1 6/2019 De Ridder
2019/0192864 A1 6/2019 Koop et al.
2019/0240468 A1 8/2019 Yun et al.
2019/0247650 A1 8/2019 Tran
2019/0262609 A1 8/2019 Brill et al.
2019/0269917 A1 9/2019 Courtine et al.
2019/0299006 A1 10/2019 Marnfeldt
2019/0321639 A1 10/2019 Rao et al.
2019/0336760 A1 11/2019 Shah
2019/0344070 A1 11/2019 Molnar et al.
2019/0344075 A1 11/2019 Bloch et al.
2019/0358454 A1 11/2019 Lin et al.
2019/0374776 A1 12/2019 Mishra et al.
2019/0374777 A1 12/2019 Burdick et al.
2019/0381313 A1 12/2019 Lu
2019/0381328 A1 12/2019 Wechter et al.
2019/0381382 A1 12/2019 Wu
2020/0009385 A1 1/2020 Shah
2020/0060602 A1 2/2020 Wagner et al.
2020/0061378 A1 2/2020 Ganguly et al.
2020/0086116 A1 3/2020 Formento et al.
2020/0121544 A1 4/2020 George et al.
2020/0139126 A1 5/2020 Napadow et al.
2020/0144846 A1 5/2020 Shin
2020/0147382 A1 5/2020 Caban et al.
2020/0155019 A1 5/2020 Esteller et al.
2020/0155865 A1 5/2020 Lu
2020/0228901 A1 7/2020 Baek
2020/0360697 A1* 11/2020 Paoles ................ A61N 1/36128
2020/0398068 A1 12/2020 Agnihotri et al.
2021/0069052 A1 3/2021 Burke
2021/0093865 A1 4/2021 Vallejo et al.
2021/0121692 A1 4/2021 Edgerton et al.
2021/0153942 A1 5/2021 Scheltienne et al.
2021/0154481 A1 5/2021 Scheltienne et al.
2021/0170177 A1 6/2021 Minassian et al.
2021/0170178 A1 6/2021 Wagner et al.
2021/0187278 A1 6/2021 Lu
2021/0213292 A1 7/2021 Minassian et al.
2021/0236837 A1 8/2021 Lu
2021/0275810 A1 9/2021 Caban
2021/0290955 A1 9/2021 Brouns et al.
2021/0299441 A1 9/2021 Edgerton et al.
2021/0378991 A1 12/2021 Lu
2021/0402186 A1 12/2021 Edgerton et al.
2022/0016420 A1 1/2022 Lo et al.
2022/0111208 A1 4/2022 Phillips et al.
2022/0125374 A1 4/2022 Courtine et al.
2022/0134108 A1 5/2022 Dinsmoor et al.
2022/0143407 A1 5/2022 Zhuang et al.
2022/0161042 A1 5/2022 Lu et al.
2022/0176130 A1 6/2022 Wu et al.
2022/0184386 A1 6/2022 Courtine et al.
2022/0233848 A1 7/2022 Gad et al.
2022/0313993 A1 10/2022 Gerasimenko et al.
2022/0409899 A1 12/2022 Ganty et al.
2023/0045403 A1 2/2023 Robison et al.
2023/0053053 A1 2/2023 Delattre et al.
2023/0186201 A1 6/2023 Cella et al.

(56) References Cited

U.S. PATENT DOCUMENTS

| | | | |
|---|---|---|---|
| 2023/0281527 | A1 | 9/2023 | Cella et al. |
| 2024/0001116 | A1 | 1/2024 | Edgerton et al. |
| 2024/0050746 | A1 | 2/2024 | Angeli et al. |
| 2024/0335666 | A1 | 10/2024 | Murphy |
| 2024/0374541 | A1 | 11/2024 | Lu et al. |
| 2024/0424291 | A1 | 12/2024 | Ganty et al. |
| 2024/0424302 | A1 | 12/2024 | Dumeny |
| 2025/0025689 | A1 | 1/2025 | Lo et al. |
| 2025/0032799 | A1 | 1/2025 | Weijand et al. |

FOREIGN PATENT DOCUMENTS

| | | | |
|---|---|---|---|
| CA | 2823592 | A1 | 7/2012 |
| CA | 2856202 | A1 | 5/2013 |
| CA | 2864473 | A1 | 5/2013 |
| CA | 3034123 | A1 | 2/2018 |
| CN | 101227940 | A | 7/2008 |
| CN | 101822223 | A | 9/2010 |
| CN | 103263727 | A | 8/2013 |
| CN | 104307098 | A | 1/2015 |
| DE | 3830429 | A1 | 3/1990 |
| DE | 202007015508 | U1 | 3/2008 |
| EP | 0034145 | A1 | 8/1981 |
| EP | 0236976 | A1 | 9/1987 |
| EP | 0630987 | A1 | 12/1994 |
| EP | 1127907 | A2 | 8/2001 |
| EP | 1303332 | A1 | 4/2003 |
| EP | 1575665 | A1 | 9/2005 |
| EP | 1675648 | A1 | 7/2006 |
| EP | 1680182 | A1 | 7/2006 |
| EP | 2130326 | A1 | 12/2009 |
| EP | 2141851 | A2 | 1/2010 |
| EP | 2160127 | A1 | 3/2010 |
| EP | 2178319 | A1 | 4/2010 |
| EP | 2192897 | A1 | 6/2010 |
| EP | 2226114 | A1 | 9/2010 |
| EP | 2243510 | A2 | 10/2010 |
| EP | 2258496 | A1 | 12/2010 |
| EP | 2361631 | A1 | 8/2011 |
| EP | 2368401 | A1 | 9/2011 |
| EP | 2387467 | A1 | 11/2011 |
| EP | 2396995 | A1 | 12/2011 |
| EP | 2397788 | A1 | 12/2011 |
| EP | 2445990 | A2 | 5/2012 |
| EP | 2471518 | A2 | 7/2012 |
| EP | 2475283 | A1 | 7/2012 |
| EP | 2486897 | A2 | 8/2012 |
| EP | 2626051 | A1 | 8/2013 |
| EP | 2628502 | A1 | 8/2013 |
| EP | 2661307 | A2 | 11/2013 |
| EP | 2665514 | A2 | 11/2013 |
| EP | 2688642 | A2 | 1/2014 |
| EP | 2810689 | A1 | 12/2014 |
| EP | 2810690 | A1 | 12/2014 |
| EP | 2868323 | A1 | 5/2015 |
| EP | 2868343 | A1 | 5/2015 |
| EP | 2966422 | A1 | 1/2016 |
| EP | 2968940 | A1 | 1/2016 |
| EP | 3184145 | A1 | 6/2017 |
| EP | 3269424 | A1 | 1/2018 |
| EP | 3323468 | A1 | 5/2018 |
| EP | 3328481 | A1 | 6/2018 |
| EP | 3381506 | A1 | 10/2018 |
| EP | 3421081 | A1 | 1/2019 |
| EP | 3285855 | B1 | 6/2019 |
| EP | 3495019 | A1 | 6/2019 |
| EP | 3527258 | A1 | 8/2019 |
| EP | 3969100 | B1 | 7/2023 |
| JP | H0326620 | A | 2/1991 |
| JP | 3184145 | B2 | 7/2001 |
| JP | 2002517283 | A | 6/2002 |
| JP | 2002200178 | A | 7/2002 |
| JP | 2004065529 | A | 3/2004 |
| JP | 2007526798 | A | 9/2007 |
| JP | 2008067917 | A | 3/2008 |
| JP | 2008543429 | A | 12/2008 |
| JP | 2009512516 | A | 3/2009 |
| JP | 2011502586 | A | 1/2011 |
| JP | 2011504112 | A | 2/2011 |
| JP | 2012515060 | A | 7/2012 |
| JP | 2013508119 | A | 3/2013 |
| JP | 2014513562 | A | 6/2014 |
| JP | 2014514043 | A | 6/2014 |
| JP | 2016506255 | A | 3/2016 |
| JP | 6132856 | B2 | 5/2017 |
| JP | 2017104685 | A | 6/2017 |
| JP | 2017523868 | A | 8/2017 |
| JP | 2017525509 | A | 9/2017 |
| JP | 2018524113 | A | 8/2018 |
| KR | 101573840 | B1 | 12/2015 |
| RU | 2130326 | C1 | 5/1999 |
| RU | 2141851 | C1 | 11/1999 |
| RU | 2160127 | C1 | 12/2000 |
| RU | 2178319 | C2 | 1/2002 |
| RU | 2192897 | C2 | 11/2002 |
| RU | 2193441 | C2 | 11/2002 |
| RU | 2001102533 | A | 11/2002 |
| RU | 2226114 | C1 | 3/2004 |
| RU | 2258496 | C2 | 8/2005 |
| RU | 2361631 | C2 | 7/2009 |
| RU | 2368401 | C1 | 9/2009 |
| RU | 2387467 | C1 | 4/2010 |
| RU | 2396995 | C2 | 8/2010 |
| RU | 2397788 | C2 | 8/2010 |
| RU | 2445990 | C1 | 3/2012 |
| RU | 2471518 | C2 | 1/2013 |
| RU | 2475283 | C2 | 2/2013 |
| RU | 2661307 | C1 | 7/2018 |
| WO | 8100458 | A1 | 2/1981 |
| WO | 9409808 | A1 | 5/1994 |
| WO | 9747357 | A1 | 12/1997 |
| WO | 9908749 | A1 | 2/1999 |
| WO | 0019912 | A1 | 4/2000 |
| WO | 0209808 | A1 | 2/2002 |
| WO | 0234331 | A2 | 5/2002 |
| WO | 02092165 | A1 | 11/2002 |
| WO | 03005887 | A2 | 1/2003 |
| WO | 03026735 | A2 | 4/2003 |
| WO | 03092795 | A1 | 11/2003 |
| WO | 2003094749 | A1 | 11/2003 |
| WO | 2004087116 | A2 | 10/2004 |
| WO | 2005002663 | A2 | 1/2005 |
| WO | 2005051306 | A2 | 6/2005 |
| WO | 2005065768 | A1 | 7/2005 |
| WO | 2005087307 | A2 | 9/2005 |
| WO | 2006026850 | A1 | 3/2006 |
| WO | 2006135751 | A2 | 12/2006 |
| WO | 2006138069 | A1 | 12/2006 |
| WO | 2007007057 | A1 | 1/2007 |
| WO | 2007007058 | A1 | 1/2007 |
| WO | 2007012114 | A1 | 2/2007 |
| WO | 2007047852 | A2 | 4/2007 |
| WO | 2007057508 | A2 | 5/2007 |
| WO | WO 2007081764 | A2 | 7/2007 |
| WO | 2007107831 | A2 | 9/2007 |
| WO | 2008075294 | A1 | 6/2008 |
| WO | 2008092785 | A1 | 8/2008 |
| WO | 2008070807 | A3 | 9/2008 |
| WO | 2008109862 | A2 | 9/2008 |
| WO | 2008121891 | A1 | 10/2008 |
| WO | 2009042217 | A1 | 4/2009 |
| WO | 2009111142 | A2 | 9/2009 |
| WO | 2010021977 | A1 | 2/2010 |
| WO | 2010055421 | A1 | 5/2010 |
| WO | 2010083308 | A1 | 7/2010 |
| WO | 2010114998 | A1 | 10/2010 |
| WO | 2010124128 | A1 | 10/2010 |
| WO | 2011005607 | A1 | 1/2011 |
| WO | 2011008459 | A2 | 1/2011 |
| WO | 2011136875 | A1 | 11/2011 |
| WO | 2012050200 | A1 | 4/2012 |
| WO | 2012075195 | A1 | 6/2012 |
| WO | 2012080964 | A1 | 6/2012 |
| WO | 2012094346 | A2 | 7/2012 |

(56) References Cited

FOREIGN PATENT DOCUMENTS

| | | | |
|---|---|---|---|
| WO | 2012100260 | A2 | 7/2012 |
| WO | 2012103519 | A2 | 8/2012 |
| WO | 2012129574 | A2 | 9/2012 |
| WO | 2013049658 | A1 | 4/2013 |
| WO | 2013069004 | A1 | 5/2013 |
| WO | 2013071307 | A1 | 5/2013 |
| WO | 2013071309 | A1 | 5/2013 |
| WO | 2013117750 | A1 | 8/2013 |
| WO | 2013152124 | A1 | 10/2013 |
| WO | 2013179230 | A1 | 12/2013 |
| WO | 2013188965 | A1 | 12/2013 |
| WO | WO 2014005075 | A1 | 1/2014 |
| WO | 2014031142 | A1 | 2/2014 |
| WO | 2014089299 | A2 | 6/2014 |
| WO | 2014144785 | A1 | 9/2014 |
| WO | WO 2014149895 | A1 | 9/2014 |
| WO | 2014205356 | A2 | 12/2014 |
| WO | 2014209877 | A1 | 12/2014 |
| WO | 2015000800 | A1 | 1/2015 |
| WO | 2015048563 | A2 | 4/2015 |
| WO | 2015063127 | A1 | 5/2015 |
| WO | 2015106286 | A1 | 7/2015 |
| WO | 2015172894 | A1 | 11/2015 |
| WO | 2016005367 | A1 | 1/2016 |
| WO | 2016025913 | A1 | 2/2016 |
| WO | 2016029159 | A2 | 2/2016 |
| WO | 2016033369 | A1 | 3/2016 |
| WO | 2016033372 | A1 | 3/2016 |
| WO | 2016064761 | A1 | 4/2016 |
| WO | 2016110804 | A1 | 7/2016 |
| WO | 2016112398 | A1 | 7/2016 |
| WO | WO 2016172239 | A1 | 10/2016 |
| WO | 2017005661 | A1 | 1/2017 |
| WO | 2017011410 | A1 | 1/2017 |
| WO | 2017024276 | A1 | 2/2017 |
| WO | 2017035512 | A1 | 3/2017 |
| WO | 2017044904 | A1 | 3/2017 |
| WO | 2017058913 | A1 | 4/2017 |
| WO | 2017062508 | A1 | 4/2017 |
| WO | 2017117450 | A1 | 7/2017 |
| WO | 2017146659 | A1 | 8/2017 |
| WO | 2017188965 | A1 | 11/2017 |
| WO | 2018033591 | A2 | 2/2018 |
| WO | 2018039458 | A1 | 3/2018 |
| WO | WO 2018039296 | A2 | 3/2018 |
| WO | 2018063879 | A1 | 4/2018 |
| WO | 2018093765 | A1 | 5/2018 |
| WO | 2018106843 | A1 | 6/2018 |
| WO | 2018140531 | A1 | 8/2018 |
| WO | 2018148844 | A1 | 8/2018 |
| WO | 2018217791 | A1 | 11/2018 |
| WO | 2019211314 | A1 | 11/2019 |
| WO | 2020028088 | A1 | 2/2020 |
| WO | 2020041502 | A1 | 2/2020 |
| WO | 2020041633 | A1 | 2/2020 |
| WO | WO 2020236946 | A1 | 11/2020 |
| WO | D215131-0001 | | 7/2022 |
| WO | 2022221442 | A1 | 10/2022 |

OTHER PUBLICATIONS

Lavrov, I. et al., "Epidural Stimulation Induced Modulation of Spinal Locomotor Networks in Adult Spinal Rats", Journal of Neuroscience, (2008), vol. 28, No. 23, pp. 6022-6029.

Levine, A. et al., "Identification of cellular node for motor control pathways", Nature Neuroscience, (2014), vol. 17, No. 4, pp. 586-593.

Liu, J. et al., "Stimulation of the parapyramidal region of the neonatal rat brain stem produces locomotor-like activity involving spinal 5-HT7 and 5-HT2A receptors", Journal of Neurophysiology, (2005), vol. 94, No. 2, pp. 1392-1404.

Lizotte, D. et al., "Automatic gait optimization with Gaussian process regression", In IJCAI, (2007), vol. 7, pp. 944-949.

Lovely, R. et al., "Effects of Training on the Recovery of Full-Weight-Bearing Stepping in the Adult Spinal Cat", Experimental Neurology, (1986), vol. 92, No. 2, pp. 421-435.

Lozano, A. et al., "Probing and Regulating Dysfunctional Circuits Using Deep Brain Stimulation", Neuron, (2013), vol. 77, No. 3, pp. 406-424.

Lu, D. et al., "Engaging cervical spinal cord networks to re-enable volitional control of hand function in tetraplegic patients", Neurorehabilitation and Neural Repair, (2016), vol. 30, No. 10, pp. 951-962.

McIntyre, C. et al., "Modeling the Excitability of Mammalian Nerve Fibers: Influence of Afterpotentials on the Recovery Cycle", Journal of Neurophysiology, (2002), vol. 87, No. 2, pp. 995-1006.

Meacham, K. W. et al., "A lithographically-patterned, elastic multi-electrode array for surface stimulation of the spinal cord", Biomed Microdevices, (2008), vol. 10, pp. 259-269.

Metzger, C. et al., "Flexible-foam-based capacitive sensor arrays for object detection at law cost", Applied Physics Letters, American Institute of Physics, (2008), vol. 92, No. 1, pp. 13506-1-13506-3.

Minassian, K. et al., "Human lumbar cord circuitries can be activated by extrinsic tonic input to generate locomotor-like activity", Human Movement Science, (2007), vol. 26, No. 2, pp. 275-295.

Minassian, K. et al., "Human Lumbar Cord Model of the Locomotor Central Pattern Generator", Second Congress International Society of Intraoperative Neurophysiology (ISIN), (2009), pp. 11-13.

Minassian, K. et al., "Mechanisms of rhythm generation of the human lumbar spinal cord in repose to tonic stimulation without and with step-related sensory feedback", Biomedical Technology, (2013), vol. 58, (Suppl. 1), pp. 1-3.

Minassian, K. et al., "Neuromodulation of lower limb motor control in restorative neurology", Clinical Neurology and Neurosurgery, (2012), vol. 114, No. 5, pp. 489-497.

Minassian, K. et al., "Neurophysiology of the human lumbar locomotor pattern generator", Proceedings 10th Vienna International Workshop on Functional Electrical Stimulation, Center for Medical Physics and Biomedical Engineering, (2010), pp. 259-261.

Minassian, K. et al., "Peripheral and Central Afferent Input to the Lumbar Cord", Biocybernetics and Biomedical Engineering, (2005), vol. 25, No. 3, pp. 11-29.

Minassian, K. et al., "Posterior root-muscle reflex", Second Congress International Society of Intraoperative Neurophysiology (ISIN), Dubrovnik, Croatia, (2009), pp. 77-80.

Minassian, K. et al., "Posterior root-muscle reflexes elicited by transcutaneous stimulation of the human lumbosacral cord", Muscle and Nerve, (2007), vol. 35, No. 3, pp. 327-336.

Minassian, K. et al., "Stepping-like movements in humans with complete spinal cord injury induced by epidural stimulation of the lumbar cord: electromyographic study of compound muscle action potentials", Spinal Cord, (2004), vol. 42, No. 7, pp. 401-416.

Minassian, K. et al., "Transcutaneous spinal cord stimulation", International Society for Restoration Neurology, (2011), pp. 1-6.

Minassian, K. et al., "Transcutaneous stimulation of the human lumbar spinal cord: Facilitating locomotor output in spinal cord injury", Society for Neuroscience, Conference Proceedings, Neuroscience 2010, San Diego, CA, Abstract Viewer/ Itinerary Planner No. 286.19, Abstract & Poster attached, (2010), 2 pages.

Minev, I. R. et al., "Electronic dura mater for long-term multimodal neural interfaces—with supplementary materials", Science, (2015), vol. 347, No. 6218, pp. 1-64.

Minev, I. R. et al., "Evaluation of an Elastomer Based Gold Microelectrode Array for Neural Recording Applications", Proceedings of the 5th International IEEE/EMBS Conference on Neural Engineering, Cancun, Mexico, (2011), pp. 482-485.

Minev, I. R. et al., "High sensitivity recording of afferent nerve activity using ultra-compliant microchannel electrodes: an acute in vivo validation", Journal of Neural Engineering, (2012), vol. 9, No. 2, pp. 1-7.

Minoux, M., "Accelerated greedy algorithms for maximizing submodular set functions", Optimization Techniques, LNCS, (1978), pp. 234-243.

Moraud, E. et al., "Mechanisms Underlying the Neuromodulation of Spinal Circuits for Correcting Gait and Balance Deficits after Spinal Cord Injury", Neuron, (2016), vol. 89, No. 4, pp. 814-828.

(56) References Cited

OTHER PUBLICATIONS

Murg, M. et al., "Epidural electric stimulation of posterior structures of the human lumbar spinal cord: 1. Muscle twitches—a functional method to define the site of stimulation", Spinal Cord, (2000), vol. 38, No. 7, pp. 394-402.
Musienko, P. et al., "Combinatory Electrical and Pharmacological Neuroprosthetic Interfaces to Regain Motor Function After Spinal Cord Injury", IEEE Transactions on Biomedical Engineering, (2009), vol. 56, No. 11, pp. 2707-2711.
Musienko, P. et al., "Controlling specific locomotor behaviors through multidimensional monoaminergic modulation of spinal circuitries", The Journal of Neuroscience, (2011), vol. 31, No. 25, pp. 9264-9278.
Musienko, P. et al., "Multi-system neurorehabilitative strategies to restore motor functions following severe spinal cord injury", Experimental Neurology, (2012), vol. 235, No. 1, pp. 100-109.
Musselman, K. et al., "Spinal Cord Injury Functional Ambulation Profile: A New Measure of Walking Ability", Neurorehabilitation and Neural Repair, (2011), vol. 25, No. 3, pp. 285-293.
Nandra, M. et al., "Microelectrode Implants for Spinal Cord Stimulation in Rats", Doctor of Philosophy Thesis, California Institute of Technology, (2014), pp. 1-104.
Nandra, M. S. et al., "A parylene-based microelectrode array implant for spinal cord stimulation in rats", Conference Proceedings IEEE Engineering in Medicine and Biology Society, (2011), pp. 1007-1010.
Nandra, M. S. et al., "A wireless microelectrode implant for spinal cord stimulation and recording in rats", Presentation Abstract, (2013), pp. 1-104.
Needle, A. R. et al., "Brain Regulation of muscle tone in healthy and functionally unstable ankles", Journal of Sport Rehabilitation, (2013), vol. 22, No. 3, pp. 202-211.
Nessler, J. et al., "A Robotic Device for Studying Rodent Locomotion After Spinal Cord Injury", IEEE Transactions on Neural Systems and Rehabilitation Engineering, (2005), vol. 13, No. 4, pp. 497-506.
Niu, T. et al., "A Proof-of-Concept Study of Transcutaneous Magnetic Spinal Cord Stimulation for Neurogenic Bladder", Scientific Reports, (2018), vol. 8, No. 1, pp. 1-12.
Park, K. J. et al., "Continuous "Over and Over" Suture for Tricuspid Ring Annuloplasty", Korean Journal of Thoracic and Cardiovascular Surgery, (2012), vol. 45, No. 1, pp. 19-23.
Peachpit, "Working with Basic Shapes in Adobe Illustrator CC (2014 release)," PeachPit, Nov. 3, 2014 [retrieved on Feb. 6, 2024]. Retrieved from the Internet: <URL: https://www.peachpit.com/articles/article.aspx?p=2253413&seqNum=3>.
Pearson, K. G., "Generating the walking gait: role of sensory feedback", Progress in Brain Research, (2004), vol. 143, Chapter 12, pp. 123-129.
Pellinen, D.S. et al., "Multifunctional Flexible Parylene-Based Intracortical Microelectrodes", Proceedings of the 2005 IEEE: Engineering in Medicine and Biology 27th Annual Conference, (2005), pp. 5272-5275.
Pflug, H. et al., "Parallel Resonant Inductive Wireless Power Transfer", IEEE, Proceedings of Wireless Power Week 2019, London, United Kingdom (2019), pp. 182-187.
Phillips, A. A. et al., "Contemporary Cardiovascular Concerns after Spinal Cord Injury: Mechanisms, Maladaptations, and Management", Journal of Neurotrama, (2015), vol. 32, No. 24, pp. 1927-1942.
Phillips, A. et al., "Perturbed and spontaneous regional cerebral blood flow responses to changes in blood pressure secondary high-level spinal cord injury: the effect of midodrine", Journal of Applied Physiology, (2014), vol. 116, No. 6, pp. 645-653.
Phillips, A. et al., "Regional neurovascular coupling and cognitive performance in those with low blood pressure secondary to high-level spinal cord injury: improved by alpha-1 agonist midodrine hydrochloride", Journal of Cerebral Blood Flow & Metabolism, (2014), vol. 34, No. 5, pp. 794-801.
Pratt, G. et al., "Stiffness Isn't Everything", Proceedings of the Fourth International Symposium on Experimental Robotics, (1995), pp. 1-6.
Pratt, J. et al., "Series elastic actuators for high fidelity force control", Industrial Robot: An International Journal, (2002), vol. 29, No. 3, pp. 234-241.
Prochazka, A. et al., "Ensemble firing of muscle afferents recorded during normal locomotion in cats", The Journal of Physiology, (1998), vol. 507, No. 1, pp. 293-304.
Prochazka, A. et al., "Models of ensemble firing of muscle spindle afferents recorded during normal locomotion in cats", The Journal of Physiology, (1998), vol. 507, No. 1, pp. 277-291.
Purves, D. et al., "Autonomic Regulation of the Bladder", Neuroscience, 2nd edition, Chapter Twenty-One, Sunderland, (MA), (2022), pp. 1-5.
Rasmussen, C. E. et al., "Gaussian Processes for Machine Learning (GPML) Toolbox", The Journal of Machine Learning Research, (2010), vol. 11, pp. 3011-3015.
Rasmussen, C. E. et al., "Gaussian Processes for Machine Learning", The MIT Press, Cambridge, Massachusetts, (2006), pp. 1-266.
Rasmussen, C. E., "Gaussian Processes in Machine Learning", LNAI, (2003), vol. 3176, pp. 63-71.
Rattay, F. et al., "Epidural electrical stimulation of posterior structures of the human lumbosacral cord: 2. Quantitative analysis by computer modeling", Spinal Cord, (2000), vol. 38, No. 8, pp. 473-489.
Reinkensmeyer, D. et al., "Tools for understanding and optimizing robotic gait training", Journal of Rehabilitation Research & Development, (2006), vol. 43, No. 5, pp. 657-670.
Rejc, E. et al., "Effects of Lumbosacral Spinal Cord Epidural Stimulation for Standing after Chronic Complete Paralysis in Humans", PLoS One, (2015), vol. 10, No. 7, pp. 1-20.
Robbins, H., "Some Aspects of the Sequential Design of Experiments", Bulletin of the American Mathematical Society, (1952), vol. 58, pp. 527-535.
Robinson, A. et al., "Hybrid stretchable circuits on silicone substrate", Journal of Applied Physics, (2014), vol. 115, No. 14, pp. 143511-1-143511-5.
Rodger, D. C. et al., "High Density Flexible Parylene-Based Multielectrode Arrays for Retinal and Spinal Cord Stimulation", Proc. of the 14th International Conference on Solid-State Sensors, Actuators and Microsystems, (2007), pp. 1385-1888.
Rosenzweig, E. et al., "Extensive Spontaneous Plasticity of Corticospinal Projections After Primate Spinal Cord Injury—with supplementary materials", Nature Neuroscience, (2010), vol. 13, No. 12, pp. 1505-1510.
Roy, F. D. et al., "Effect of percutaneous stimulation at different spinal levels on the activation of sensory and motor roots", Experimental Brain Research, (2012), vol. 223, pp. 281-289.
Rubinstein et al., "Current Density Profiles of Surface Mounted and Recessed Electrodes for Neural Prostheses", Biomedical Engineering, IEEE Transactions on BME, (1987), vol. 34, No. 11, pp. 864-875.
Ryzhov, I. O. et al., "The knowledge gradient algorithm for a general class of online learning problems", Operations Research, (2012), vol. 60, No. 1, pp. 1-47.
Sayenko, D. et al., "Neuromodulation of evoked muscle potentials induced by epidural spinal-cord stimulation in paralyzed individuals", Journal of Neurophysiology, (2014), vol. 111, No. 5, pp. 1088-1099.
Sayenko, D. G. et al., "Spinal segment-specific transcutaneous stimulation differentially shapes activation pattern among motor pools in humans", Journal of Applied Physiology, (2015), vol. 118, No. 11, pp. 1364-1374.
Schmidlin, E. et al., "Behavioral Assessment of Manual Dexterity in Non-Human Primates", Journal of Visualized Experiments, (2011), vol. 57, No. e3258, pp. 1-11.
Seifert, H. M. et al., "Restoration of Movement Using Functional Electrical Stimulation and Bayes' Theorem", The Journal of Neuroscience, (2002), vol. 22, No. 21, pp. 9465-9474.
Shafik, A. et al., "Extrapelvic cavernous nerve stimulation in erectile dysfunction. Human Study", Andrologia, (1996), vol. 28, No. 3, pp. 151-156.

(56) References Cited

OTHER PUBLICATIONS

Shafik, A. et al., "Magnetic stimulation of the cavernous nerve for the treatment of erectile dysfunction in humans", International Journal of Impotence Research, (2000), vol. 12, No. 3, pp. 137-141.
Shamir, R. et al., "Machine learning approach to optimizing combined stimulation and medication therapies for Parkinson's disease—with supplementary materials", Brain Stimulation, (2015), vol. 8, No. 6, pp. 1025-1032.
Sharpe, A. et al., "Upper-limb muscles responses to epidural, subdural and intraspinal stimulation of the cervical spinal cord", Journal of Neural Engineering, (2014), vol. 11, No. 1, pp. 1-16.
Sherman, J. et al., "Measurements of the normal cervical spinal cord on MR Imaging", American Journal of Neuroradiology, (1990), vol. 11, No. 2, pp. 369-372.
Srinivas, N. et al., "Gaussian process optimization in the bandit setting: No regret and experimental design", In Proceedings of the 27th International Conference on Machine Learning, (2010), pp. 1-17.
Steward, O. et al., "False Resurrections: Distinguishing Regenerated from Spared Axons in the Injured Central Nervous System", The Journal of Comparative Neurology, (2003), vol. 459, No. 1, pp. 1-8.
Stienen, A. et al., "Analysis of reflex modulation with a biologically realistic neural network", Journal of Computer Neuroscience, (2007), vol. 23, pp. 333-348.
Sun, F. et al., "Sustained axon regeneration induced by co-deletion of PTEN and SOCS3—with supplementary material", Nature, (2011), vol. 480, No. 7377, pp. 372-375.
Suzuki, T. et al., "A 3D flexible parylene probe array for multichannel neural recording", IEEE Neural Engineering, (2003), pp. 154-156.
Szava, Z. et al., "Transcutaneous electrical spinal cord stimulation: Biophysics of a new rehabilitation method after spinal cord injury", VDM Publishing, Saarbrucken, Germany, (2011), pp. 1-95.
Takeoka, A. et al., "Muscle Spindle Feedback Directs Locomotor Recovery and Circuit Reorganization after Spinal Cord Injury", Cell, (2014), vol. 159, No. 7, pp. 1626-1639.
Takeuchi, S. et al., "3D flexible multichannel neural probe array", Journal of Micromechanics and Microengineering, (2004), vol. 14, No. 1, pp. 104-107.
Tanabe, S. et al., "Effects of transcutaneous electrical stimulation combined with locomotion-like movement in the treatment of post-stroke gait disorder: a single-case study", (2008), vol. 30, No. 5, pp. 411-416.
Temel, Y. et al., "Case Report—Deep brain stimulation of the thalamus can influence penile erection", International Journal of Impotence Research, (2004), vol. 16, No. 1, pp. 91-94.
Tenne, Y. et al., "Computational Intelligence in Expensive Optimization Problems", Adaptation, Learning, and Optimization, Springer, Berlin Heidelberg, (2010), vol. 2, pp. 131-162.
Timoszyk, W. et al., "Hindlimb loading determines stepping quantity and quality following spinal cord transection", Brain Research, (2005), vol. 1050, No. 1-2, pp. 180-189.
Troni, W. et al., "A methodological reappraisal of non invasive high voltage electrical stimulation of lumbosacral nerve roots", Clinical Neurophysiology, (2011), vol. 122, No. 10, pp. 2071-2080.
Tungjitkusolmun, S. et al., "Finite element analyses of uniform current density electrodes for radio-frequency cardiac ablation", IEEE Transactions on Biomedical Engineering, (2000), vol. 47, No. 1, pp. 32-40.
Valchinov, E. S. et al., "An active electrode for biopotential recording from small localized bio-sources", BioMedical Engineering OnLine, (2004), vol. 3, No. 25, pp. 1-14.
Vallery, H. et al., "Compliant Actuation of Rehabilitation Robots", IEEE Robotics & Automation Magazine, (2008), vol. 15, No. 3, pp. 60-69.
Van Den Brand, R. et al., "Restoring Voluntary Control of Locomotion after Paralyzing Spinal Cord Injury", Science Magazine, (2012), vol. 336, No. 6085, pp. 1182-1185.
Wan, D. et al., "Life-threatening outcomes associated with autonomic dysreflexia: A clinical review", Journal of Spinal Cord Medicine, (2014), vol. 37, No. 1, pp. 2-10.
Wang, J. M. et al., "Gaussian process dynamical models for human motion", IEEE Transactions on Pattern Analysis and Machine Intelligence, (2007), vol. 30, No. 2, pp. 283-298.
Wang, T. et al., "Incidence of C5 nerve root palsy after cervical surgery—A meta-analysis for decade", Medicine, (2017), vol. 96, No. 45, pp. 1-14.
Ward, A. R. et al., "Sensory, motor, and pain thresholds for stimulation with medium frequency alternating current", Archives of Physical Medicine and Rehabilitation, (1998), vol. 79, No. 3, pp. 273-278.
Ward, A. R., "Electrical Stimulation Using Kilohertz-Frequency Alternating Current", Physical Therapy, (2009), vol. 89, No. 2, pp. 181-190.
Wei, P. et al., "Stretchable microelectrode array using room-temperature liquid alloy interconnects", Journal of Micromechanics and Microengineering, (2011), vol. 21, No. 054015, pp. 1-8.
Wenger, N. et al., "Closed-loop neuromodulation of spinal sensorimotor circuits controls refined locomotion after complete spinal cord injury", Science Translational Medicine, (2014), vol. 6, Issue 255, pp. 1-11.
Wenger, N. et al., "Spatiotemporal neuromodulation therapies engaging muscle synergies improve motor control after spinal cord injury—with supplementary material", Natural Medicine, (2016), vol. 22, No. 2, pp. 138-145.
Wenger, N. et al., "Supplementary Materials for Closed-loop neuromodulation of spinal sensorimotor circuits controls refined locomotion after complete spinal cord injury", Science Translational Medicine, (2014), vol. 6, Iss. 255, pp. 1-14.
Wernig, A. et al., "Laufband locomotion with body weight support improved walking in persons with severe spinal cord injuries", International Medical Society of Paraplegia, (1992), vol. 30, No. 4, pp. 229-238.
Wernig, A., "Ineffectiveness• of Automated Locomotor Training", Archives of Physical Medicine and Rehabilitation, (2005), vol. 86, No. 12, pp. 2385-2386.
International Search Report and Written Opinion issued in counterpart PCT Application No. PCT/US2014/057886 mailed Dec. 24, 2014, 6 pages.
International Search Report and Written Opinion issued in counterpart PCT Application No. PCT/US2015/011263 mailed May 19, 2015, 12 pages.
International Search Report and Written Opinion issued in counterpart PCT Application No. PCT/US2015/046378 mailed Dec. 1, 2015, 5 pages.
International Search Report and Written Opinion issued in counterpart PCT Application No. PCT/US2015/047268 mailed Dec. 8, 2015, 17 pages.
International Search Report and Written Opinion issued in counterpart PCT Application No. PCT/US2015/047272 mailed Dec. 3, 2015, 11 pages.
International Search Report and Written Opinion issued in counterpart PCT Application No. PCT/US2016/041802 mailed Sep. 12, 2016, 17 pages.
International Search Report and Written Opinion issued in counterpart PCT Application No. PCT/US2016/045898 mailed Dec. 5, 2016, 13 pages.
International Search Report and Written Opinion issued in counterpart PCT Application No. PCT/US2016/049129 mailed Dec. 5, 2016, 13 pages.
International Search Report and Written Opinion issued in counterpart PCT Application No. PCT/US2017/015435, mailed May 8, 2017, 9 pages.
International Search Report and Written Opinion issued in counterpart PCT Application No. PCT/US2018/015098 mailed Mar. 12, 2018, 9 pages.
International Search Report and Written Opinion issued in counterpart PCT Application No. PCT/US2018/033942 mailed Aug. 31, 2018, 8 pages.

(56) References Cited

OTHER PUBLICATIONS

International Search Report and Written Opinion issued in counterpart PCT Application No. PCT/US2019/047551 mailed Nov. 21, 2019, 9 pages.
International Search Report and Written Opinion issued in counterpart PCT Application No. PCT/US2019/047777 mailed Nov. 14, 2019, 15 pages.
International Search Report and Written Opinion issued in counterpart PCT Application No. PCT/US2020/033830 mailed Oct. 14, 2020, 10 pages.
International Search Report and Written Opinion issued in counterpart PCT Application No. PCT/US2022/024673 mailed Jun. 28, 2022, 8 pages.
International Search Report issued in counterpart PCT Application No. PCT/US2012/020112 mailed Jul. 30, 2012, 4 pages.
International Search Report issued in counterpart PCT Application No. PCT/US2012/022257 mailed Sep. 3, 2012, 4 pages.
International Search Report issued in counterpart PCT Application No. PCT/US2012/030624 mailed Oct. 31, 2012, 3 pages.
International Search Report issued in counterpart PCT Application No. PCT/US2012/064874 mailed Mar. 19, 2013, 4 pages.
Ivanenko, Y. P. et al., "Temporal Components of the Motor Patterns Expressed by the Human Spinal Cord Reflect Foot Kinematics", Journal of Neurophysiology, (2003), vol. 90, No. 5, pp. 3555-3565.
Iyer, P. C. et al., "Characterization of stimulus response curves obtained with transcranial magnetic stimulation from bilateral tibialis anterior muscles post stroke", Neuroscience Letters, (2019), vol. 713, pp. 1-15.
Jaman, R., "A retrospective cross-sectional survey of lumbo-sacral recorded at the D.U.T. Chiropractic Day Clinic (1995-2005)", (2014). Durban University of Technology, Master's Degree in Technology dissertation. Retrieved from the Internet: <URL: https://doi.org/10.51415/10321/221>, 94 pages.
Jarosiewicz, B. et al., "Supplementary Materials for Virtual typing by people with tetraplegia using a self-calibrating intracortical brain-computer interface", Science Translational Medicine, (2015), vol. 7, No. 313, pp. 1-26.
Jarosiewicz, B. et al., "Virtual typing by people with tetraplegia using a self-calibrating intracortical brain-computer interface", Science Translational Medicine, (2015), vol. 7, No. 313, pp. 1-11.
Jenny, A. B. et al., "Principles of Motor Organization of the Monkey Cervical Spinal Cord", The Journal of Neuroscience, (1983), vol. 3, No. 3, pp. 567-575.
Jilge, B. et al., "Initiating extension of the lower limbs in subjects with complete spinal cord injury by epidural lumbar cord stimulation", Experimental Brain Research, (2004), vol. 154, pp. 308-326.
Johnson, W. et al., "Application of a Rat Hindlimb Model: A Prediction of Force Spaces Reachable Through Stimulation of Nerve Fascicles", IEEE Transactions on Bio- Medical Engineering, (2011), vol. 58, No. 12, pp. 3328-3338.
Jones, D. R. et al., "Efficient Global Optimization of Expensive Black-Box Functions", Journal of Global Optimization, (1998), vol. 13, pp. 455-492.
Jones, K. et al., "Computer Simulation of the Responses of Human Motoneurons to Composite 1A EPSPS: Effects of Background Firing Rate", The Journal of Physiology, (1997), vol. 77, No. 1, pp. 405-420.
Jonic, S. et al., "Three machine learning techniques for automatic determination of rules to control locomotion", IEEE Transactions on Biomedical Engineering, (1999), vol. 46, No. 3, pp. 300-310.
Kakulas, A. B., "A Review of the Neuropathology of Human Spinal Cord Injury with Emphasis on Special Features", Proceedings of the Donald Munro Memorial Lecture at the American Paraplegia Society 44th Annual Conference, Las Vegas, NV, Spinal Cord, (1999), vol. 22, No. 2, pp. 119-124.
Kapetanakis, S. et al., "Cauda Equina Syndrome Due to Lumbar Disc Herniation: a Review of Literature", Folia Medica, (2017), vol. 59, No. 4, pp. 377-386.
Kim, W. S. et al., "Ultra-sensitive Flexible Pressure Sensor with Stamped Polyurethane Rubber", 2011 11th IEEE Conference on Nanotechnology, (2011), pp. 1607-1610.
Kim, Y. et al., "Electrical behavior of defibrillation and pacing electrodes", Proceedings of the IEEE, (2002), vol. 84, No. 3, pp. 446-456.
Kirazh, O. et al., "Anatomy of the spinal dorsal root entry zone: its clinical significance", Acta Neurochirurgica, (2014), vol. 156, pp. 2351-2358.
Kirkwood, P., "Neuronal Control of Locomotion: From Mollusc to Man", G.N. Orlovsky, T.G. Deliagina and S. Grillner. Oxford University Press, Oxford, 1999. ISBN 0198524056 (Hbk), 322 pp., Clinical Neurophysiology, vol. 111, (2000): 1524-1525.
Kitano, K. et al., "Spinal reflex in human lower leg muscles evolved by transcutaneous spinal cord stimulation", Journal of Neuroscience Methods, (2009), vol. 180, No. 1, pp. 111-115.
Kleinberg, R. et al., "Multi-armed bandits in metric spaces", In STOC, Computer and Automation Research Institute of the Hungarian Academy of Sciences, Budapest, Hungary, (2008), pp. 1-26.
Kocsis, L. et al., "Bandit Based Monte-Carlo Planning", European Conference on Machine Learning, Springer, Berlin, Heidelberg, (2006), pp. 282-293.
Kondo, T. et al., "Laser monitoring of chest wall displacement", European Respiratory Journal, (1997), vol. 10, No. 8, pp. 1865-1869.
Krassioukov, A. et al., "A Systematic Review of the Management of Autonomic Dysreflexia Following Spinal Cord Injury", Archives of Physical Medicine and Rehabilitation, (2009), vol. 90, No. 4, pp. 682-695.
Krassioukov, A. et al., "A Systematic Review of the Management of Orthostatic Hypotension Following Spinal Cord Injury", Archives of Physical Medicine and Rehabilitation, (2009), vol. 90, No. 5, pp. 876-885.
Krause, A. et al., "Contextual Gaussian Process Bandit Optimization", In Advances in Neural Information Processing Systems (NIPS), (2011), pp. 1-9.
Krause, A. et al., "Near-optimal Nonmyopic Value of Information in Graphical Models", In UAI, (2005), pp. 1-8.
Krause, A. et al., "Near-Optimal Sensor Placements in Gaussian Processes: Theory, Efficient Algorithms and Empirical Studies", Journal of Machine Learning Research, (2008), vol. 9, pp. 235-284.
Krenn, M. et al., "Selectivity of transcutaneous stimulation of lumbar posterior roots at different spinal levels in humans", Biomedical Technology, (2013), vol. 58 (Suppl. 1), pp. 1-2.
Kwakkel, G. et al., "Effects of Robot-assisted therapy on upper limb recovery after stroke: A Systematic Review", Neurorehabilitation and Neural Repair, (2008), vol. 22, No. 2, pp. 111-121.
Lacour, S. et al., "Flexible and stretchable micro-electrodes for in vitro and in vivo neural interfaces", Medical & Biological Engineering & Computing, (2010), vol. 48, pp. 945-954.
Lacour, S. et al., "Stretchable gold conductors on elastomeric substrates", Applied Physics Letters, (2003), vol. 82, No. 15, pp. 2404-2406.
Ladenbauer, J. et al., "Stimulation of the human lumbar spinal cord with implanted and surface electrodes: a computer simulation study", IEEE Transactions on Neural Systems and Rehabilitation Engineering, (2010), vol. 18, No. 6, pp. 637-645.
Communication Pursuant to Rule 114(2) EPC in counterpart European Patent Application No. 12847885.6 mailed Mar. 27, 2015, 28 pages.
Communication Regarding Extended European Search Report in counterpart European Patent Application No. 24153829.7 mailed May 22, 2024, 8 pages.
Cotton, D. P. J. et al., "A Multifunctional Capacitive Sensor for Stretchable Electronic Skins", IEEE Sensors Journal, IEEE Service Center, New York, NY, US, (2009), vol. 9, No. 12, pp. 2008-2009.
Coursera, "What is Machine Learning? Definition, Types, and Examples," Coursera, May 20, 2025. Retrieved from the Internet: <URL:https://www.coursera.org/articles/what-is-machine-learning>, 12 pages.
Courtine, G. et al., "Can experiments in nonhuman primates expedite the translation of treatments for spinal cord injury in humans?", Nature Medicine, (2007), vol. 13, No. 5, pp. 561-566.

(56) References Cited

OTHER PUBLICATIONS

Courtine, G. et al., "Modulation of multisegmental monosynaptic responses in a variety of leg muscles during walking and running in humans", Journal of Physiology, (2007), vol. 582, No. 3, pp. 1125-1139.
Courtine, G. et al., "Recovery of supraspinal control of stepping via indirect propriospinal relay connections after spinal cord injury", Nature Medicine, (2008), vol. 14, No. 1, pp. 69-74.
Courtine, G. et al., "Transformation of nonfunctional spinal circuits into functional states after the loss of brain input", Nature Neuroscience, (2009), vol. 12, No. 10, pp. 1333-1342.
Cowley, K. et al., "Propriospinal neurons are sufficient for bulbospinal transmission of the locomotor command signal in the neonatal rat spinal cord", The Journal of Physiology, (2008), vol. 586, No. 6, pp. 1623-1635.
Cyganowski, A et al., "Stretchable electrodes for neuroprosthetic interfaces", Sensors, 2012 IEEE, Taipei, (2012), pp. 1-4.
Dani, V. et al., "Stochastic Linear Optimization Under Bandit Feedback", In Proceedings of the 21st Annual Conference on Learning Theory (COLT), (2008), No. 101, pp. 1-15.
Danner, S. et al., "Human Spinal locomotor control is based on flexibly organized burst generators", Brain: A Journal of Neurology, (2015), vol. 138, No. 3, pp. 577-588.
Danner, S. M. et al., "Body Position Influences Which neural structures are recruited by lumbar transcutaneous spinal cord stimulation", PLoS One, (2016), vol. 11, No. 1, pp. 1-13.
Danner, S. M. et al., "Can the Human Lumbar Posterior Columns be Stimulated by Transcutaneous Spinal Cord Stimulation? A modeling study", Europe PMC funders author manuscripts, Artificial Organs, (2011), vol. 35, No. 3, pp. 257-262.
Decision to Refuse a European Patent Application in counterpart European Patent Application No. 15834593.4 mailed Oct. 28, 2021, 24 pages.
Definition of "Insert", Dictionary [online], Oxford English Dictionary, 2020 [retrieved on Dec. 15, 2022], 2 pages.
Desantana, J. M. et al., "Effectiveness of Transcutaneous Electrical Nerve Stimulation for Treatment of Hyperalgesia and Pain", Current Rheumatology Reports, (2008), vol. 10, pp. 492-499.
Dimitrijevic, M. M. et al. "Evidence for a Spinal Central Pattern Generator in Humans", Annals New York Academy Sciences, (1998), vol. 860, No. 1, pp. 360-376.
Dimitrijevic, M. M. et al., "Clinical Elements for the Neuromuscular Stimulation and Functional Electrical Stimulation protocols in the Practice of Neurorehabilitation", Artificial Organs, vol. 26, No. 4, (2002), pp. 256-259.
Dimitrijevic, M. R. et al., "Electrophysiological characteristics of H-reflexes elicited by percutaneous stimulation of the cauda equina", Abstract No. 4927, 34th Annual Meeting of the Society for Neuroscience, San Diego, CA (2004), 1 page.
Dominici, N. et al. "Versatile robotic interface to evaluate, enable and train locomotion and balance after neuromotor disorders", Nature Medicine, (2012), vol. 18, No. 7, pp. 1-8.
Drew, T. et al., "Cortical mechanisms involved in visuomotor coordination during precision walking", Brain Research Reviews, (2008), vol. 57, No. 1, pp. 199-211.
Drummond, G. B. et al., "Thoracic impedance used for measuring chest wall movement in postoperative patients", British Journal of Anaesthesia, (1996), vol. 77, No. 3, pp. 327-332.
Dubinsky, R. M. et al., "Assessment: Efficacy of transcutaneous electric nerve stimulation in the treatment of pain in neurologic disorders (an evidenced-based review)", Report of the Therapeutics and Technology Assessment Subcommittee of the American Academy of Neurology, Neurology, (2010), vol. 74, No. 2, pp. 173-176.
Dunne, L. et al., "Initial development and testing of a novel foam-based pressure sensor for wearable sensing", Journal of NeuroEngineering and Rehabilitation, (2005), vol. 2, No. 4, pp. 1-7.
Duschau-Wicke, A. et al., "Patient-cooperative control increases active participation of individuals with SCI during robot-aided gait training", Journal of NeuroEngineering and Rehabilitation, (2010), vol. 7, No. 43, pp. 1-13.
Edgerton, V. et al., "Robotic Training and Spinal Cord Plasticity", Brain Research Bulletin, (2009), vol. 78, No. 1, pp. 4-12.
Edgerton, V. et al., "Training Locomotor Networks", Brain Research Reviews, (2008), vol. 57, No. 1, pp. 241-254.
Edgerton, V. R. et al., "Epidural stimulation of the spinal cord in spinal cord injury: current status and future challenges", Expert Review of Neurotherapeutics, (2011), vol. 11, No. 10, pp. 1351-1353.
EPO Communication and Supplementary European Search Report in counterpart European Patent Application No. 17745012.9 mailed Aug. 13, 2019, 8 pages.
European Opposition filed in counterpart European Patent Application No. 17826212.7 mailed Dec. 2, 2022, 56 pages.
European Reply to Communication in counterpart European Patent Application No. 12847885.6 mailed Oct. 24, 2016, 4 pages.
Extended European Search Report in counterpart European Patent Application No. 14765477.6 mailed Nov. 8, 2016, 10 pages.
Extended European Search Report in counterpart European Patent Application No. 14849355.4 mailed May 10, 2017, 7 pages.
Extended European Search Report in counterpart European Patent Application No. 15834593.4 mailed Apr. 4, 2018, 7 pages.
Extended European Search Report in counterpart European Patent Application No. 15836927.2 mailed Mar. 1, 2018, 9 pages.
Extended European Search Report in counterpart European Patent Application No. 16825005.8 mailed Feb. 19, 2019, 8 pages.
Extended European Search Report in counterpart European Patent Application No. 16833973.7 mailed Dec. 13, 2018, 6 pages.
Extended European Search Report in counterpart European Patent Application No. 18173218.1 mailed Jan. 7, 2019, 6 pages.
Extended European Search Report in counterpart European Patent Application No. 18744685.1 mailed Sep. 7, 2020, 8 pages.
Extended European Search Report in counterpart European Patent Application No. 19201998.2 mailed Apr. 21, 2020, 7 pages.
Extended European Search Report in counterpart European Patent Application No. 19211738.0 mailed May 27, 2020, 8 pages.
Extended European Search Report in counterpart European Patent Application No. 19851613.0 mailed Apr. 19, 2022, 9 pages.
Extended European Search Report in counterpart European Patent Application No. 19852797.0 mailed Apr. 19, 2022, 6 pages.
Extended European Search Report in counterpart European Patent Application No. 20020190.3 mailed Oct. 5, 2020, 7 pages.
Extended European Search Report in counterpart European Patent Application No. 20163794.9 mailed Sep. 18, 2020, 7 pages.
Extended European Search Report in counterpart European Patent Application No. 20164082.8 mailed Jul. 21, 2020, 7 pages.
Extended European Search Report in counterpart European Patent Application No. 20175385.2 mailed Jan. 22, 2021, 8 pages.
Extended European Search Report in counterpart European Patent Application No. 21166801.7 mailed Aug. 17, 2021, 11 pages.
Extended European Search Report in counterpart European Patent Application No. 23189900.6 mailed Jan. 15, 2024, 7 pages.
Extended European Search Report in counterpart European Patent Application No. 12847885.6 mailed May 6, 2015, 7 pages.
Extended European Search Report in counterpart European Patent Application No. 19211698.6 mailed May 28, 2020, 6 pages.
Feng, G. H. et al., "Universal concept for fabricating micron to millimeter sized 3-D parylene structures on rigid and flexible substrates", in Proc. IEEE 15th Internal Conference on Micro Electro Mechanical System, Kyoto, Japan, (2003), pp. 594-597.
Fleshman, J. et al., "Electronic Architecture of Type-Identified a-Motoneurons in in the Cat Spinal Cord", Journal of Neurophysiology, (1988), vol. 60, No. 1, pp. 60-85.
Fong, A J. et al., "Recovery of control of posture and locomotion after a spinal cord injury: solutions staring us in the face", Progress in Brain Research, Elsevier Amsterdam, Netherlands, (2009), vol. 175, Chapter 25, pp. 393-418.
Frey, M. et al., "A Novel Mechatronic Body Weight Support System", IEEE Transactions on Neural Systems and Rehabilitation Engineering, (2006), vol. 14, No. 3, pp. 311-321.
Fuentes, R. et al., "Spinal Cord Stimulation Restores Locomotion in Animal Models of Parkinson's Disease," Science, (2009), vol. 323, No. 5921, pp. 1578-1582.

(56) References Cited

OTHER PUBLICATIONS

Ganley, K. J. et al., "Epidural Spinal Cord Stimulation Improves Locomotor Performance in Low Asia C, Wheelchair-Dependent, Spinal Cord-Injured Individuals: Insights from Metabolic Response", Topics in Spinal Cord Injury Rehabilitation, (2005), vol. 11, No. 2, pp. 50-63.
Gerasimenko, Y. et al., "Initiation and modulation of locomotor circuitry output with multisite transcutaneous electrical stimulation of the spinal cord in noninjured humans", Journal of Neurophysiology, (2015), vol. 113, No. 3, pp. 834-842.
Gerasimenko, Y. et al., "Noninvasive Reactivation of Motor Descending Control after Paralysis", Journal of Neurotrauma, (2015), vol. 32, No. 24, pp. 1968-1980.
Gerasimenko, Y. et al., "Novel and Direct Access to the Human Locomotor Spinal Circuitry", Journal of Neuroscience, (2010), vol. 30, No. 10, pp. 3700-3708.
Gerasimenko, Y. et al., "Spinal cord reflexes induced by epidural spinal cord stimulation in normal awake rats", Journal of Neuroscience Methods, (2006), vol. 157, No. 2, pp. 253-263.
Gerasimenko, Y. et al., "Transcutaneous electrical spinal-cord stimulation in humans", Annals of Physical and Rehabilitation Medicine, (2015), vol. 58, No. 4, pp. 225-231.
Gerasimenko, Y. P. et al., "Control of Locomotor Activity in Humans and Animals in the Absence of Supraspinal Influences", Neuroscience and Behavioral Physiology, (2002), vol. 32, No. 4, pp. 417-423.
Gerasimenko, Y. P. et al., "Epidural Spinal Cord Stimulation Plus Quipazine Administration Enable Stepping Complete Spinal Adult Rats", Journal of Neurophysiology, (2007), vol. 98, No. 5, pp. 2525-2536.
Gilja, V. et al., "A high-performance neural prosthesis enabled by control algorithm design—with supplementary materials", Nature Neuroscience, (2012), vol. 15, No. 12, pp. 1-56.
Ginsbourger, D. et al., "Kriging is well-suited to parallelize optimization", Computational Intelligence in Expensive Optimization Problems, Berlin, Heidelberg: Springer Berlin Heidelberg, (2010), Ch. 6, pp. 131-162.
Gittins, J.C., "Bandit Processes and Dynamic Allocation Indices", Journal of the Royal Statistical Society B, (1979), vol. 41, No. 2, pp. 148-164.
Giuliano, F. et al., "Neural Control of Erection", Physiology & Behavior, (2004), vol. 83, No. 2, pp. 189-201.
Graf, N. et al., "Electrochemically Stimulated Release from Liposomes Embedded in a Polyelectrolyte Multilayer", Advanced Functional Materials, (2011), vol. 21, No. 9, pp. 1666-1672.
Graz, I. et al., "Flexible ferroelectret field-effect transistor for large-area sensor skins and microphones", Applied Physics Letters, American Institute of Physics, (2006), vol. 89, No. 7, pp. 73501-1-73501-3.
Graz, I. et al., "Silicone substrate with in situ strain relief for stretchable thin-film transistors", Applied Physics Letters, AIP, American Institute of Physics, (2011), vol. 98, No. 12, pp. 124101-1-124101-3.
Guyatt, G. et al., "The 6-minute walk: a new measure of exercise capacity in patients with chronic heart failure", Canadian Medical Association Journal, (1985), vol. 132, No. 8, pp. 919-923.
Hagglund, M. et al., "Activation of groups of excitatory neurons in the mammalian spinal cord or hindbrain evokes locomotion", Nature Neuroscience, (2010), vol. 13, No. 2, pp. 246-252.
Harkema, S. et al., "Effect of Epidural stimulation of the lumbosacral spinal cord on voluntary movement, standing, and assisted stepping after motor complete paraplegia: a case study", Lancet, (2011), vol. 377, No. 9781, pp. 1938-1947.
Harkema, S. et al., "Human Lumbosacral Spinal Cord Interprets Loading During Stepping", Journal of Neurophysiology, (1997), vol. 77, No. 2, pp. 797-811.
Harkema, S. et al., "Normalization of Blood Pressure with Spinal Cord Epidural Stimulation After Severe Spinal Cord Injury", Frontiers in Human Neuroscience, (2018), vol. 12, pp. 1-11.
Harrison, P. et al., "Individual Excitatory Post-Synaptic Potentials Due to Muscle Spindle Ia Afferents in Cat Triceps Surae Motoneurones", The Journal Physiology, (1981), vol. 312, No. 1, pp. 455-470.
Hashtrudi-Zaad, K. et al., "On the Use of Local Force Feedback for Transparent Teleoperation", Proceedings of the 1999 IEEE International Conference on Robotics and Automation, (1999), vol. 3, pp. 1863-1869.
Health Journalism Glossary: Bidirectional, Definition [online], Association of Health Care Journalists, 2024. Retrieved from the Internet: <URL:https://healthjournalism.org/glossary-terms/bidirectional/>, 3 pages.
Hennig, P. et al., "Entropy search for information-efficient global optimization", Journal of Machine Learning Research (JMLR), (2012), vol. 13, No. 1, pp. 1809-1837.
Herman, R. et al., "Spinal cord stimulation facilitates functional walking in a chronic, incomplete spinal cord injured", Spinal Cord, (2002), vol. 40, No. 2, pp. 65-68.
Hidler, J. et al., "ZeroG: Overground gait and balance training system", Journal of Rehabilitation Research & Development, (2011), vol. 48, No. 4, pp. 287-298.
Hines, M. et al., "The NEURON Simulation Environment", Neural Computation, (1997), vol. 9, No. 6, pp. 1179-1209.
Hofstoetter, U. S. et al., "Modification of spasticity by transcutaneous spinal cord stimulation in individuals with incomplete spinal cord injury", The Journal of Spinal Cord Medicine, (2014), vol. 37, No. 2, pp. 202-211.
Hofstoetter, U.S. et al., "Effects of transcutaneous spinal cord stimulation on voluntary locomotor activity in an incomplete spinal cord injured individual", Biomedical Technology, (2013), vol. 58 (Suppl. 1), pp. 1-3.
Hofstoetter, U.S. et al., "Modification of Reflex Responses to Lumbar Posterior Root Stimulation by Motor Tasks in Healthy Subjects", Artificial Organs, (2008), vol. 32, No. 8, pp. 644-648.
Hofstotter, U.S. et al., "Model of spinal cord reflex circuits in humans: Stimulation frequency-dependence of segmental activities and their interactions", Second Congress International Society of Intraoperative Neurophysiology (ISIN), Dubrovnik, Croatia, (2009), pp. 1-149.
Hohenschurz-Schmidt, D. J. et al., "Linking Pain Sensation to the Autonomic Nervous System: The Role of the Anterior Cingulate and Periaqueductal Gray Resting-State Networks", Front Neuroscience, (2020), vol. 14, No. 147, pp. 1-15.
Hovey, C. et al., "The New Guide to Magnet Stimulation", The Magstim Company Ltd., (2006), pp. 1-45.
Hung, C. C. et al., "Transparent microprobe array fabricated by MEMS hot embossing technology for photodynamic therapy application", IEICE Electronics Express, (2010), vol. 7, No. 9, pp. 569-576.
Ichiyama, R. M. et al., "Hindlimb stepping movements in complete spinal rats induced by epidural spinal cord stimulation", Neuroscience Letters, (2005), vol. 383, No. 3, pp. 339-344.
International Search Report and Written Opinion issued in counterpart PCT Application No. EP2020/063564, mailed Sep. 11, 2020, 12 pages.
International Search Report and Written Opinion issued in counterpart PCT Application No. PCT/EP2017/083478, mailed May 3, 2018, 10 pages.
International Search Report and Written Opinion issued in counterpart PCT Application No. PCT/EP2018/082939, mailed Feb. 14, 2019, 11 pages.
International Search Report and Written Opinion issued in counterpart PCT Application No. PCT/EP2018/082942, mailed Feb. 14, 2019, 11 pages.
International Search Report and Written Opinion issued in counterpart PCT Application No. PCT/EP2020/053381, mailed May 12, 2020, 8 pages.
International Search Report and Written Opinion issued in counterpart PCT Application No. PCT/EP2020/063563, mailed Jul. 30, 2020, 14 pages.
International Search Report and Written Opinion issued in counterpart PCT Application No. PCT/US2012/064878 mailed Mar. 19, 2013, 11 pages.

(56) References Cited

OTHER PUBLICATIONS

International Search Report and Written Opinion issued in counterpart PCT Application No. PCT/US2014/029340 mailed Aug. 6, 2014, 11 pages.
Wessels, M. et al., "Body Weight-Supported Gait Training for Restoration of Walking in People With an Incomplete Spinal Cord Injury: A Systematic Review", Journal of Rehabilitation Medicine, (2010), vol. 42, No. 6, pp. 513-519.
Widmer, C. et al., "Inferring latent task structure for multitask learning by multiple kernel learning", BMC Bioinformatics, (2010), vol. 11, pp. 1-8.
Wiley, J. D. et al., "Analysis and Control of the Current Distribution under Circular Dispersive Electrodes", Biomedical Engineering, IEEE Transactions on BME, (1982), vol. 29, No. 5, pp. 381-385.
Winter, D. et al., "An integrated EMG/biomechanical model of upper body balance and posture during human gait", Progress in Brain Research, (1993), vol. 97, Ch. 32, pp. 359-367.
Wirz, M. et al., "Effectiveness of automated locomotor training in patients with chronic incomplete spinal cord injury: a multicenter trial", Archives of Physical Medicine and Rehabilitation, (2005), vol. 86, No. 4, pp. 672-680.
Yakovenko, S. et al., "Spatiotemporal Activation of Lumbosacral Motoneurons in the Locomotor Step Cycle", Journal of Neurophysiology, (2002), vol. 87, No. 3, pp. 1542-1553.
YouTube video entitled: "How to Round Corners in Illustrator," uploaded Sep. 6, 2017 by user "Mohamed Achraf" [retrieved on Jul. 7, 2022]. Retrieved from the Internet: <URL:https://www.youtube.com/watch?v=q8Cyd0sqY6A>, 3 pages.
Zhang, T. C. et al., "Mechanisms and models of spinal cord stimulation for the treatment of neuropathic pain", Brain Research, (2014), vol. 1569, pp. 19-31.
Zorner, B. et al., "Profiling locomotor recovery: comprehensive quantification of impairments after CNS damage in rodents", Nature Methods, (2010), vol. 7, No. 9, pp. 701-708.
Abernethy, J. et al., "Competing in the dark: An efficient algorithm for bandit linear optimization", Conference on Learning Theory, (2009), No. 110, pp. 1-13.
Ada, L. et al., "Mechanically assisted walking with body weight support results in more independent walking than assisted overground walking in non-ambulatory patients early after stroke: a systematic review", Journal of Physiotherapy, (2010), vol. 56, No. 3, pp. 153-161.
Alto, L. et al., "Chemotropic guidance facilitates axonal regeneration and synapse formation after spinal cord injury", Nature Neuroscience, (2009), vol. 12, No. 9, pp. 1106-1113.
Anderson, K., "Targeting recovery: priorities of the spinal cord-injured population", Journal of Neurotrauma, (2004), vol. 21, No. 10, pp. 1371-1383.
Andersson, K. E. et al., "CNS Involvement in Overactive Bladder—Pathophysiology and Opportunities for Pharmacological Intervention", Drugs, (2003), vol. 63, No. 23, pp. 2595-2611.
Angeli, C. et al., "Altering spinal cord excitability enables voluntary movements after chronic complete paralysis in humans", Brain: A Journal of Neurology, (2014), vol. 137, No. 5, pp. 1394-1409.
Anonymous, "Re: Round corners (fillet) in Illustrator CS6", in: Stack Exchange [online], Graphic Design, Jan. 22, 2018; 17:52 [retrieved on Feb. 6, 2024]. Retrieved from the Internet: <URL:https://graphicdesign.stackexchange.com/questions/104349/round-corners-fillet-in-illustrator-cs6>, 10 pages.
Anonymous, Lumbar Decompression Surgery: When it's used, Datasheet [online], National Health Service, 2022. Retrieved from the Internet: <URL:https://www.nhs.uk/conditions/lumbar-decompression-surgery/why-its-done/#:-:text=Cauda%equina%20syndrome%20a.is%20severe%20or%20getting%20worse, 2 pages.
Anonymous, Vital Signs, Datasheet [online], Cleveland Clinic [retrieved on Nov. 22, 2021]. Retrieved from the Internet: <URL:https://my.clevelandclinic.org/health/articles/10881-vital-signs, 19 pages.
Ateh, D. D. et al., "Polypyrrole-based conducting polymers and interactions with biological tissues", Journal of the Royal Society Interface, (2006), vol. 3, No. 11, pp. 741-752.
Auer, P. et al., "Finite-time analysis of the multiarmed bandit problem", Machine Learning, (2002), vol. 47, No. 2, pp. 235-256.
Auer, P., "Using confidence bounds for exploitation-exploration trade-offs", Journal of Machine Learning Research, (2002), vol. 3, pp. 397-422.
Axisa, F. et al., "Elastic and Conformable Electronic Circuits and Assemblies using MID in polymer", 6th International Conference on Polymers and Adhesives in Microelectronics and Photonics, IEEE Polytronic 2007 Conference, (2007), pp. 280-286.
Azimi, J. et al., "Batch Active Learning via Coordinated Matching", In Proceedings of the 29th International Conference on Machine Learning, (2012), pp. 1-8.
Azimi, J. et al., "Batch Bayesian Optimization via Simulation Matching", In Advances in Neural Information Processing Systems (NIPS), (2010), pp. 1-9.
Azimi, J. et al., "Hybrid Batch Bayesian Optimization", In Proceedings of the 29th International Conference on Machine Learning, (2012), pp. 1-12.
Barbeau, H. et al., "Recovery of locomotion after chronic spinalization in the adult cat", Brain Research, (1987), vol. 412, No. 1, pp. 84-95.
Bareyre, F. et al., "The injured spinal cord spontaneously forms a new intraspinal circuit in adult rats", Nature Neuroscience, (2004), vol. 7, No. 3, pp. 269-277.
Basso, D. et al., "MASCIS Evaluation of Open Field Locomotor Scores: Effects of Experience and Teamwork on Reliability", Journal of Neurotrauma, (1996), vol. 13, No. 7, pp. 343-359.
Bizzi, E. et al., "Modular organization of motor behavior", Zeitschrift für Naturforschung, (1998), vol. 53, No. 7-8, pp. 510-517.
Brochu, et al., "A Tutorial on Bayesian Optimization of Expensive Cost Functions, with Application to Active User Modeling and Hierarchical Reinforcement Learning", In TR-2009-23, UBC, (2009), pp. 1-49.
Brosamle, C. et al., "Cells of Origin, Course, and Termination Patterns of the Ventral, Uncrossed Component of the Mature Rat Corticospinal Tract", The Journal of Comparative Neurology, (1997), vol. 386, No. 2, pp. 293-303.
Bruckenstein, S. et al., "An experimental study of nonuniform current distribution at rotating disk electrodes", Journal of the Electrochemical Society, (1970), vol. 117, No. 8, pp. 1044-1048.
Bubeck, S. et al., "Online Optimization in X-Armed Bandits", Advances in Neural Information Processing Systems (NIPS), (2008), pp. 1-8.
Bubeck, S. et al., "Pure Exploration in Finitely-Armed and Continuous-Armed Bandits problems", In ALT, (2009), pp. 1-35.
Burke, R., "Group la Synaptic Input to Fast and Slow Twitch Motor Units of Cat Triceps Surae", The Journal of Physiology, (1968), vol. 196, No. 3, pp. 605-630.
Cai, L. et al., "Implications of Assist-As-Needed Robotic Step Training after a Complete Spinal Cord Injury on Intrinsic Strategies of Motor Learning", The Journal of Neuroscience, (2006), vol. 26, No. 41, pp. 10564-10568.
Capogrosso, M. et al., "A Brain-Spinal Interface Alleviating Gait Deficits after Spinal Cord Injury in Primates", Nature, (2016), vol. 539, No. 7628, pp. 284-288.
Capogrosso, M. et al., "A Computational Model for Epidural Electrical Stimulation of Spinal Sensorimotor Circuits", Journal of Neuroscience, (2013), vol. 33, No. 49, pp. 19326-19340.
Carhart, M. et al., "Epidural Spinal-Cord Stimulation Facilitates Recovery of Functional Walking Following Incomplete Spinal-Cord Injury", IEEE Transactions on Neural Systems and Rehabilitation Engineering, (2004), vol. 12, No. 1, pp. 32-42.
Chatagny, P. et al., "Distinction between hand dominance and hand preference in primates: a behavioral investigation of manual dexterity in nonhuman primates (macaques) and human subjects", Brain and Behavior, (2013), vol. 3, No. 5, pp. 575-595.
Colgate, E. et al., "An Analysis of Contact Instability in Terms of Passive Physical Equivalents", Proceedings of the 1989 IEEE International Conference on Robotics and Automation, Scottsdale, Arizona, (1989), pp. 404-409.
Communication Pursuant to Article 94(3) EPC in counterpart European Application No. 19209911.7 mailed Jul. 20, 2023, 5 pages.

(56) References Cited

OTHER PUBLICATIONS

Communication Pursuant to Article 94(3) EPC in counterpart European Application No. 19209911.7 mailed Mar. 1, 2023, 2 pages.
Communication Pursuant to Article 94(3) EPC in counterpart European Patent Application No. 12760696.0 mailed Nov. 9, 2017, 5 pages.
Communication Pursuant to Article 94(3) EPC in counterpart European Patent Application No. 12847885.6 mailed Apr. 15, 2016, 5 pages.
Communication Pursuant to Article 94(3) EPC in counterpart European Patent Application No. 12847885.6 mailed Feb. 16, 2017, 5 pages.
Communication Pursuant to Article 94(3) EPC in counterpart European Patent Application No. 12848368.2 mailed May 9, 2018, 5 pages.
Communication Pursuant to Article 94(3) EPC in counterpart European Patent Application No. 14765477.6 mailed Nov. 14, 2018, 5 pages.
Communication Pursuant to Article 94(3) EPC in counterpart European Patent Application No. 14765477.6 mailed Sep. 27, 2019, 6 pages.
Communication Pursuant to Article 94(3) EPC in counterpart European Patent Application No. 14849355.4 mailed Jul. 20, 2018, 6 pages.
Communication Pursuant to Article 94(3) EPC in counterpart European Patent Application No. 15834593.4 mailed Jul. 17, 2019, 4 pages.
Communication Pursuant to Article 94(3) EPC in counterpart European Patent Application No. 15834593.4 mailed Jul. 30, 2020, 5 pages.
Communication Pursuant to Article 94(3) EPC in counterpart European Patent Application No. 17826212.7 mailed Dec. 21, 2020, 7 pages.
Communication Pursuant to Article 94(3) EPC in counterpart European Patent Application No. 18807366.2 mailed Mar. 22, 2023, 4 pages.
Communication Pursuant to Article 94(3) EPC in counterpart European Patent Application No. 20160841.1 mailed Mar. 6, 2024, 5 pages.
Communication Pursuant to Article 94(3) EPC in counterpart European Patent Application No. 20726108.2 mailed Mar. 20, 2024, 4 pages.
Communication Pursuant to Article 94(3) EPC in counterpart European Patent Application No. 211660801.7 mailed Mar. 7, 2024, 6 pages.
Communication Pursuant to Article 94(3) EPC in counterpart European Patent Application No. 21166801.7 mailed Mar. 7, 2024, 6 pages.
Communication Pursuant to Article 94(3) EPC in counterpart European Patent Application No. 24153829.7 mailed Apr. 4, 2025, 5 pages.
"Aching knee or sore back? New app helps doctors treat pain," medicalxpress.com, (2017), Retrieved from the Internet: <URL: https://medicalxpress.com/news/2017-05-aching-knee-sore-app-doctors. html>, 1 page.
"Back pain and body posture infographic," Alamy.com, (2017), Retrieved from the Internet: <URL:https://www.alamy.com/stock-photo-back-pain-and-body-posture-infographic-with-anatomical-illustrations-141494074.html?imageid=27CC5905-F123-4DSC-847A4C76D50631C1&p=313080&pn=1&searchId=526c9d4db7f91a3e259d7b785fa370c3&searchtype=0>, 2 pages.
European Patent Office Action in counterpart European Patent Application No. 25165562.7 mailed Sep. 2, 2025, 9 pages.
Ichiyama et al., "Step training reinforces specific spinal Iocomotor circuitry in adult spinal rats," Journal of Neuroscience, (2008), vol. 28, No. 29, pp. 7370-7375.
"Male and female muscle and skeletal systems," Shutterstock. com, (2021), Retrieved from the Internet: <URL: https://www.shutterstock.com/image-illustration/male-female-muscle-skeletal-systems-xray-1895443960>, 2 pages.
"Screenshots of the electric patient-reported outcome app final prototype," Researchgate.net, (2020), Retrieved from the Internet: <URL:https://www.researchgate.net/figure/Screenshots-of-the-electronic-patient-reported-outcome-app-final-prototype_fig>, 1 page.

* cited by examiner

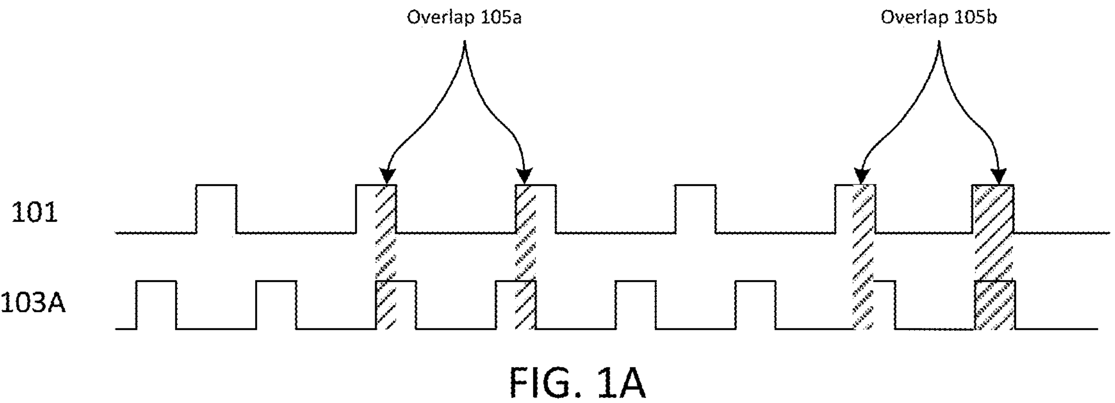
FIG. 1A
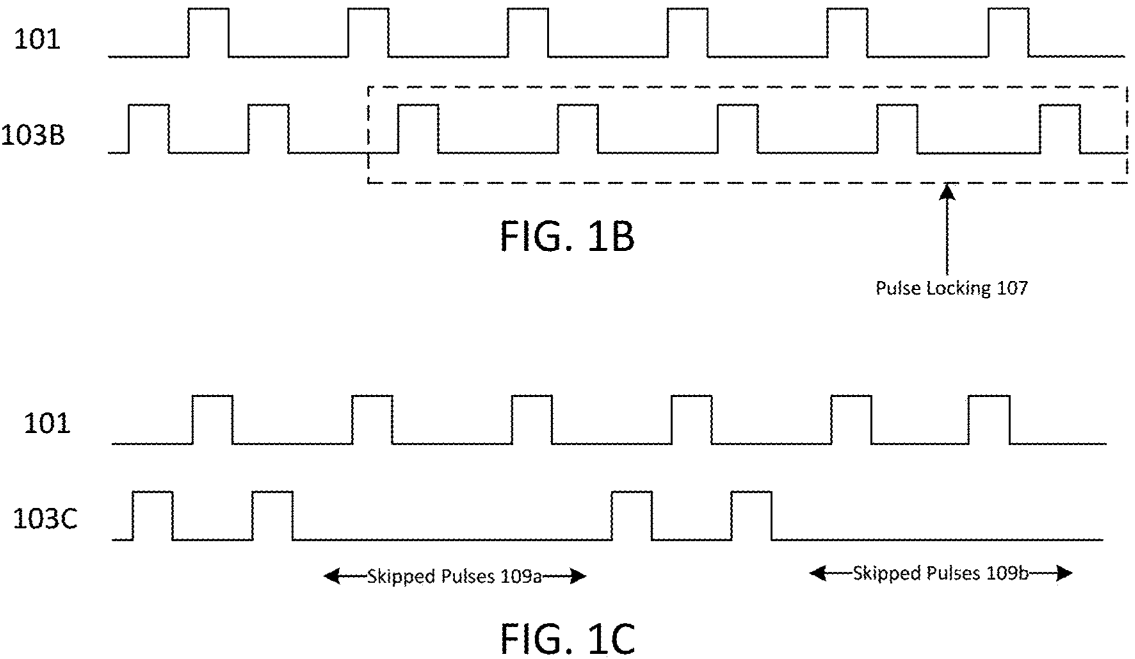
FIG. 1B
FIG. 1C

STOCHASTIC STIMULATION SCHEDULING

TECHNICAL FIELD

The disclosed systems and methods concern creation of stimulation pulse schedules for neuromodulation and/or neurostimulation systems. In particular, the disclosed systems and methods concern stochastic stimulation pulse schedules that avoid phase locking or pulse skipping.

BACKGROUND

Neuromodulation and/or neurostimulation systems can address physical or neurological injuries, diseases, or conditions of a patient by providing stimulation to the patient in complicated patterns that involve multiple stimulation channels (e.g., stimulation partitures). However, the more complicated the stimulation pattern and the more stimulation channels involved, the greater the likelihood that two stimulation channels will provide simultaneous, or nearly simultaneous, stimulation. When this happens, the effects can be synergistic and unpredictable. The patient can experience pain or unpleasant sensations; and muscles, nerves, organs, or other structures of the patient can be unintentionally or excessively activated.

Conventional approaches to preventing simultaneous activation include pre-calculating stimulation schedules, delaying pulses, or skipping pulses. However, these conventional approaches present technical problems. Pre-calculating stimulation schedules can be time consuming and inflexible, and does not guarantee the existence of a suitable stimulation schedule; delaying pulses can result in phase locking; and skipping pulses can result in irregular bursts of stimulation.

SUMMARY

The disclosed systems and methods relate to a scheduling stimulation system. The stimulation scheduling system can include a control signal generator configured to generate pulse schedules for a set of stimulation channels using stimulation parameter distributions and a controller configured to update the stimulation parameter distributions based at least in part on the difficulty in generating consistent pulse schedules. In some embodiments, the stimulation parameter distributions can be updated based at least in part on the fidelity of the generated pulse schedules.

The disclosed embodiments include a stimulation scheduling method. The method can include sampling a stimulation parameter distribution for a first stimulation channel to obtain a stimulation parameter value. The method can further include generating a first pulse schedule for the first stimulation channel using the stimulation parameter value. The method can further include comparing the first pulse schedule to a second pulse schedule for a second stimulation channel. The method can further include, based on the comparison, providing a stimulator control signal to a stimulator. The stimulator control signal can be based on the first pulse schedule. The stimulator can be configured to provide stimulation according to the stimulator control signal on the first stimulation channel.

The disclosed embodiments include a stimulation scheduling system. The system can include a control signal generator. The control signal generator can be configured to generate a set of consistent pulse schedules according to a set of corresponding stimulation parameter distributions. The control signal generator can be further configured to provide a stimulator control signal to a stimulator. The stimulator control signal can be based on the set of consistent pulse schedules. The stimulator can be configured to provide stimulation according to the stimulator control signal on a set of stimulation channels. The control signal generator can be further configured to provide at least one detection parameter based on the generation of the set of consistent pulse schedules to a controller. The controller can be configured to estimate a difficulty state based on the at least one detection parameter. The controller can be further configured to update the stimulation parameter distributions based on the estimated difficulty state.

The disclosed embodiments include a stimulation scheduling system. The system can include an implantable pulse generator. The implantable pulse generator can be configured to target, using a control signal generator and a controller, a degree of difficulty in generating consistent pulse schedules for a set of stimulation channels by updating stimulation parameter distributions for the stimulation channels, the stimulation parameter distributions used to generate the consistent pulse schedules.

It is to be understood that both the foregoing general description and the following detailed description are exemplary and explanatory only and are not restrictive of the disclosed embodiments, as claimed.

BRIEF DESCRIPTION OF THE DRAWINGS

The drawings are not necessarily to scale or exhaustive. Instead, emphasis is generally placed upon illustrating the principles of the embodiments described herein. The accompanying drawings, which are incorporated in and constitute a part of this specification, illustrate several embodiments consistent with the disclosure and, together with the description, serve to explain the principles of the disclosure. In the drawings:

FIG. 1A depicts pulse overlap in an exemplary stimulation partiture, consistent with disclosed embodiments.

FIG. 1B depicts phase locking in an exemplary stimulation partiture, consistent with disclosed embodiments.

FIG. 1C depicts pulse skipping in an exemplary stimulation partiture, consistent with disclosed embodiments.

DETAILED DESCRIPTION

Figure 2:
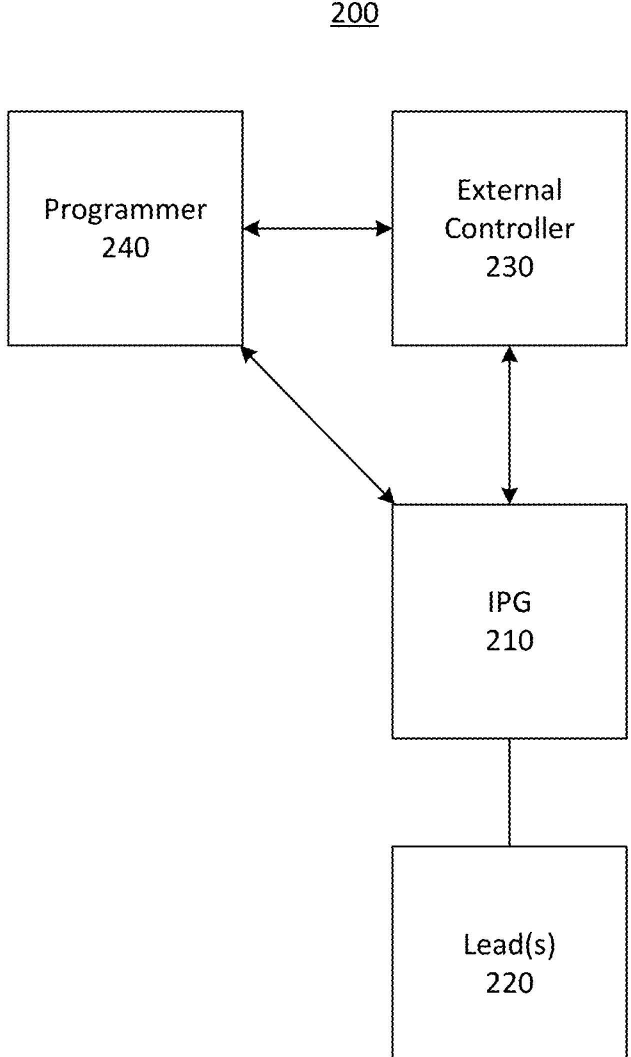
FIG. 2 depicts an exemplary system capable of providing stimulation to a patient, consistent with disclosed embodiments.

Reference will now be made in detail to exemplary embodiments, discussed with regards to the accompanying drawings. In some instances, the same reference numbers will be used throughout the drawings and the following description to refer to the same or like parts. Unless otherwise defined, technical or scientific terms have the meaning commonly understood by one of ordinary skill in the art. The disclosed embodiments are described in sufficient detail to enable those skilled in the art to practice the disclosed embodiments. It is to be understood that other embodiments may be utilized and that changes may be made without departing from the scope of the disclosed embodiments. Thus, the materials, methods, and examples are illustrative only and are not intended to be necessarily limiting.

Stimulation, as described herein, can include electrical stimulation. In some embodiments, stimulation can include optical, mechanical, or other suitable stimulation modalities.

A patient, as described herein, can be the individual to whom stimulation is provided. A user, as described herein, can be the patient, a caregiver of the patient, or a service provider (e.g., a technician; a clinician, such as a doctor, nurse, rehabilitation specialist, physical therapist, or the like; or other service provider).

A stimulation partiture, as described herein, can specify stimulation parameters for multiple stimulation channels. In some embodiments, these stimulation channels can be configured for provision to the patient as a single unit. In some embodiments, the stimulation partiture can be designed and intended to provide a particular physiological effect or effects. For example, a stimulation partiture can specify multiple channels of stimulation that correspond to different muscles of the feet, legs, and trunk. The stimulation partiture can define a sequence of stimulation times and/or stimulation amplitudes for these channels. In this example, the stimulation partiture can be designed such that, when stimulation is provided according to the stimulation partiture by a stimulator through a suitably configured arraignment of leads to a paraplegic patient, the paraplegic patient rises to a standing position from a seated position. As may be appreciated, such a positional change requires a complex combination of muscle activations.

In some embodiments, a stimulation partiture can specify parameters for conditional execution of one or more of the stimulation channels. Such conditional execution can involve sensor signals received from the patient or the body of the patient. For example, a stimulation partiture can specify multiple channels of stimulation configured to inhibit bladder contractions and increase urethral sphincter tone in response to an increase in bladder pressure detected by a sensor implanted in the bladder of a patient. In such an instance, the stimulation partiture can define the triggering conditions, as well as the stimulation response.

Stimulation parameters, as described herein, can include inter-burst interval; number of stimulation pulses in a burst; inter-pulse interval; first phase stimulation amplitude; first phase stimulation duration; first phase pulse shape, or the like. In some embodiments, stimulation parameters can include inter-phase duration and the shapes, amplitudes, durations, or the like of any subsequent phases in a stimulation pulse (e.g., second phase stimulation amplitude, second phase stimulation duration, second phase stimulation pulse shape, or the like). In some embodiments, stimulation parameters can include the choice of stimulation contacts (e.g., which electrode is used on a multi-contact electrode); stimulation polarity (e.g., monopolar, bipolar, or the like); whether the stimulation phases are charge-balanced, whether the stimulation is current or voltage controlled, or the like.

A stimulation partiture can include multiple stimulation channels. Each stimulation channel can provide stimulation pulses to the patient according to specified stimulation parameters for that stimulation channel. In some instances, these stimulation parameters can be selected to cause the stimulation pulses to achieve a desired physiological effect, while minimizing undesired side effects. For example, the stimulation parameters for a stimulation channel can be selected to evoke or enable a target muscle contraction (e.g., as part of a gait cycle), while minimizing painful or unpleasant sensations or the activation of other nearby non-target muscles or organs. The selection of stimulation parameters for one stimulation channel may be performed independently of the selection of stimulation parameters for another stimulation channel.

However, a stimulation partiture can specify that stimulation be provided simultaneously on multiple stimulation channels. Absent some mitigation measure, providing simultaneous stimulation on multiple stimulation channels can result in stimulation pulses of different channels overlapping (or nearly overlapping). FIG. 1A depicts two stimulation channels 101 and 103A that have differing stimulation parameters. The stimulation channels are depicted as having a "low" value that indicates no stimulation is being provided and a "high" value that indicates provision of stimulation. Overlap 105A and overlap 105*b* indicate overlapping stimulation pulses. In general, given two stimulation channels having differing stimulation periods p milliseconds and q milliseconds, stimulation pulses of the two stimulation channels will necessarily overlap within pq milliseconds.

When a stimulation pulses on multiple channels overlap (or nearly overlap), the two stimulation pulses can interact in unintended ways. For example, the two stimulation pulses may interact synergistically. Such synergistic interactions can have undesirable consequences, such painful or unpleasant sensations, excessive activation of target muscles or organs, or unplanned activation of other, non-target target muscles or organs.

In some instances, stimulation timings for a stimulation partiture can be pre-calculated to prevent overlapping stimulation pulses. However, such pre-calculation can be time-consuming. The difficulty of finding stimulation timings that prevent overlapping stimulation pulses can increase with the number of stimulation channels. Furthermore, changes to stimulation parameters may require re-determination of the stimulation timings. As tuning a stimulation partiture to a particular patient may require many such changes, pre-calculating stimulation timings may be clinically infeasible. Furthermore, such pre-calculation may not be able to accommodate variable stimulation patterns, such as those arising from conditional execution of stimulation channels, variable-duration stimulation, feedback control of stimulation parameters, or the on-the-fly addition, removal, enabling, disabling, or modification of stimulation parameters.

Conventional approaches to stimulation scheduling include delaying pulses and skipping pulses to prevent stimulation pulses on different channels from overlapping. But each of these techniques can create problems.

When avoiding overlapping by delaying pulses, one stimulation pulse can be delayed until another stimulation pulse ends. As depicted in FIG. 1B, this approach can result in phase locking. Stimulation channels 101 and 103B are both configured to provide stimulation pulses having a fixed inter-pulse interval. Stimulation channel 103B is configured to delay stimulation pulses that would otherwise overlap with stimulation pulses on stimulation channel 101. However, as depicted in FIG. 1B, beginning a stimulation pulse on stimulation channel 103B upon the end of a stimulation pulse on stimulation channel 101 only ensures that the next stimulation pulse on stimulation channel 103B will overlap with the next stimulation pulse on stimulation channel 101.

As a result, the stimulation pulses on stimulation channel 103B become phase-locked with the stimulation pulses on stimulation channel 101 (e.g., pulse locking 107).

When avoiding overlapping by skipping pulses, one of the overlapping pulses can simply be skipped. As depicted in FIG. 1B, this approach can result in irregular stimulation, particularly when stimulation channels have similar frequencies. Stimulation channels 101 and 103C are both configured to provide stimulation pulses having a fixed inter-pulse interval. Stimulation channel 103B is configured to skip stimulation pulses that would otherwise overlap with stimulation pulses on stimulation channel 101. As a result, as stimulation channels 101 and 103C drift into and out of phase, multiple pulses in a row are skipped for stimulation channel 103C (e.g., skipped pulses 109A and 109B), converting this stimulation channel from a pattern of continuous stimulation to an irregular beat pattern.

The disclosed embodiments address these technical problems using stochastic stimulation pulse schedules. A control signal generator can sample stimulation parameter distributions to generate sampled stimulation parameter values. The control signal generator can then generate pulses schedules using the sampled stimulation parameter values. The control signal generator can test these pulse schedules are tested to determine whether they are consistent. When a set of pulse schedules is consistent, the control signal generator can provide a control signal to the stimulator. The control signal can cause the stimulator to provide stimulation in accordance with the consistent set of pulse schedules. Otherwise, the control signal generator can re-sample one or more of the stimulation parameter distributions and repeat the pulse schedule generation process.

In some embodiments, the control signal generator and a controller can maintain a control loop. The control loop can control parameters of the stimulation parameter distributions to balance the difficulty of generating consistent sets of pulse schedules against the fidelity of the generated pulse schedules. The controller can use a probability distribution to model the difficulty of generating consistent sets of pulse schedules. In some embodiments, the controller can estimate parameter(s) describing this distribution. The controller can provide updates to the stimulation parameter distributions to cause these estimated parameters to converge on specified values.

In this manner, the disclosed embodiments can accommodate stimulation partitures including many stimulation channels having differing stimulation parameters. The disclosed embodiments do not require pre-calculation of stimulation timings. The disclosed embodiments are therefore suitable for clinical use in tuning post-implantation stimulation parameters. Furthermore, the disclosed embodiments can accommodate conditional execution of stimulation channels, variable-duration stimulation, feedback control of stimulation parameters, or the on-the-fly addition, removal, enabling, disabling, or modification of stimulation parameters. Furthermore, the disclosed embodiments prevent phase locking and pulse skipping.

FIG. 2 depicts an exemplary system 200 capable of providing stimulation to a patient, consistent with disclosed embodiments. System 200 can enable flexible, customizable provision of stimulation to the patient. In some embodiments, programmer 240 and external controller 230 can be separate devices. Programmer 240 can be a user-facing device and be configured to enable a user to generate a stimulation partiture for a patient. Programmer 240 can therefore support creation or modification of stimulation partitures. External controller 230 can be a patient-facing device and can enable a patient or user to enable, disable, trigger, halt, or adjust stimulation provided by IPG 210 in accordance with a predetermined stimulation partiture (e.g., a stimulation partiture created by programmer 240). A programmer can be used to configure external controllers or IPGs for multiple patients, while an external controller can be associated with a particular patient.

In various embodiments, programmer 240 and external controller 230 can be implemented using the same device. For example, such a device can have multiple accounts having different privileges, such as a patient account and a user account. In such embodiments, a patient account can provide the functionality of external controller 230, while a user account can provide the functionality of programmer 240.

In various embodiments, an implantable controller can be used in place of external controller 230. The implantable controller can possess functionality of external controller 230, as described herein. In some such embodiments, the implantable controller and IPG 210 can be combined in a single device. Alternatively, the implantable controller and IPG 210 can be in separate devices.

In various embodiments, an external pulse generator can be used in place of implantable pulse generator 210. For example, an external pulse generator connected to percutaneous leads can be used to determine whether a patient is responsive to stimulation. If the patient is responsive, then the patient can be outfitted with an implantable stimulator. In such embodiments, the external pulse generator can possess functionality of implantable pulse generator 210, as described herein. Furthermore, the external pulse generator and one or more of the external controller and programmer can be implemented using a single device. For example, a single device can provide the functionality of the pulse generator and the external controller, or the pulse generator, external controller, and programmer. Alternatively, the external pulse generator, external controller, and programmer can be implemented using separate devices.

Consistent with disclosed embodiments, IPG 210 can be configured to provide stimulation signals on stimulation channels. In some embodiments, the stimulation channels can be independently controllable. IPG 210 can be configured to receive instructions from at least one of external controller 230 or programmer 240. The instructions can include instructions to load a stimulation partiture, or parameters that specify a stimulation partiture, into a memory of IPG 210. The instructions can include instructions to modify a stimulation partiture or delete a stimulation partiture from a memory of IPG 210. The instructions can include instructions to enable or disable an output of IPG 210. The instructions can include instructions to start or cease stimulation according to a stimulation partiture.

For example, IPG 210 can receive (e.g., from external controller 230 or programmer 240) a first stimulation partiture (or parameters specifying the stimulation partiture) corresponding to a component of a gait cycle. IPG 210 can provide stimulation to the patient according to the stimulation partiture. While providing stimulation according to the first stimulation partiture, IPG 210 can receive another stimulation partiture corresponding to the next component of the gait cycle. Upon completion of stimulation according to the first stimulation partiture, IPG 210 can provide stimulation according to the second stimulation partiture. As a result of the sequential execution of such stimulation partitures, the patient can be moved through a gait cycle.

In some embodiments, IPG 210 can be configured for implantation into a patient. IPG 210 can include control circuitry, communication circuitry, and a connection component. The control circuitry can include at least one processor (e.g., a microprocessor, a microcontroller, an Application Specific Integrated Circuit, or another suitable processor) and at least one memory containing instructions that control the operation of IPG 210. In some embodiments, the communication circuitry can be configured to support wireless communication with external controller 230 or programmer 240. In such embodiments, the communication circuitry can include an antenna (e.g., a radio-frequency antenna, such as an antenna coil, or the like), an optical link (e.g., an optical detector, or the like), or any other suitable communication components. In some embodiments, the communication circuitry can support wired communication with external controller 230 or programmer 240. In such embodiments, communication circuitry can include suitable connectors and/or connectors for created wired percutaneous connections with other components of system 200. The connection component can enable IPG 210 to connect with leads (e.g., leads 220) to provide stimulation through the leads without unacceptable signal distortion or power loss. The disclosed embodiments are not limited to any particular interconnection architecture.

In some embodiments, IPG 210 can include a power source. In some embodiments, the power source can be configured to store power for operating IPG 210 within the device (e.g., a battery, a fuel cell, or another suitable power source). In some embodiments, the power source can be configured to obtain power from an external source (which can then be stored internally, in some embodiments). For example, IPG 210 can include a radiofrequency coil for receiving externally transmitted power.

In some embodiments, IPG 210 can include a stimulator. In some embodiments, the stimulator can be configured to convert control signals into stimulation signals that can be provided to the patient. In some embodiments, the control signals can be logic signals, an array or time series of digital data, or any other suitable control signal. For example, when the stimulation is electrical stimulation, the stimulator can be or include one or more amplifier(s). The input to the amplifier(s) can be nanowatt or microwatt control signals and the output of the amplifier can be milliwatt voltage-controlled or current controlled-stimulation signals. The stimulator can include outputs corresponding to the multiple stimulation channels of IPG 210.

In some embodiments, the components of IPG 210 can be contained inside a container. The container can be sealed (e.g., hermetically sealed) to prevent or reduce communication between the environment (e.g., the implantation site within the patient) and the interior of IPG 210. In some embodiments, the container can include an electrically conductive portion. The electrically conductive portion can serve, in some instances, as a return path for current, or as a ground reference for electrical stimulation.

Consistent with disclosed embodiments, leads 220 can be configured to provide stimulation signals to the patient. In some embodiments, leads 220 can include connectors, wiring or cabling, and stimulation contacts. Connectors can be configured to interconnect with corresponding connectors on IPG 210. Wiring or cabling can convey stimulation signals from IPG 210 to the stimulation contacts. The particular implementation of the connectors, wiring or cabling, and stimulation contacts can depend on the stimulation modality. For example, when the stimulation is electrical stimulation, the stimulation contacts can be or include electrodes (which can have contact(s)). The wiring or cabling can provide electrical connectivity from IPG 210 to the electrodes.

The disclosed embodiments are not limited to any particular electrode design. Suitable electrode designs can include array or microarray electrodes, paddle electrodes; lead electrodes including circumferential contact(s), side contact(s), or tip contact(s); cuff electrodes; wire or microwire electrodes; or any other suitable electrode design.

The disclosed embodiments are not limited to any electrodes designed for any particular purpose. Suitable electrodes include brain-computer interface electrodes, deep brain stimulation electrodes, cochlear stimulation electrodes, retinal stimulation electrodes, vagal stimulation electrodes, spinal cord stimulation electrodes, foramen stimulation electrodes, bladder or bowel control stimulation electrodes, intramuscular stimulation electrodes, efferent stimulation electrodes, afferent stimulation electrodes, autonomic stimulation electrodes, enteric stimulation electrodes, or electrodes designed for some other suitable purpose.

Consistent with disclosed embodiments, external controller 230 can be configured to enable a patient or user to enable, disable, trigger, halt, or adjust stimulation provided by IPG 210. In some embodiments, external controller 230 can extend the capabilities of IPG 210 by storing sets of stimulation partitures. In some embodiments, external controller 230 can additionally extend the capabilities of IPG 210 by storing execution conditions or relationships for stimulation partitures. External controller 230 can provide stimulation partitures to IPG 210 in response to, or in accordance with, these execution conditions or relationships. In this manner, external controller 230 can circumvent memory or computational limitations of IPG 210.

Consistent with disclosed embodiments, external controller 230 can receive instructions from programmer 240. The instructions can include instructions to load a stimulation partiture into a memory of external controller 230. The instructions can include instructions to modify or delete a stimulation partiture from a memory of external controller 230. In some embodiments, the instructions received from programmer 240 can define sets of stimulation partitures and execution conditions or relationships among these stimulation partitures.

Consistent with disclosed embodiments, external controller 230 can be configured to provide instructions to IPG 210. These instructions can include instructions to IPG 210 to load a stimulation partiture, modify or delete a stimulation partiture, enable or disable a stimulation channel of IPG 210, start or cease execution of a loaded stimulation partiture, or the like. For example, external controller 230 can receive instructions from programmer 240 that define a set of stimulation partitures corresponding to a gait cycle. The instructions can also specify an execution relationship: that these stimulation partitures be provided to IPG 210 in an appropriate sequence. Then, in response to some trigger (e.g., a patient interaction with an interface of external controller 230), external controller 230 can provide the stimulation partitures to IPG 210 in the sequence. External controller 230 can provide the stimulation partitures such that the next stimulation partiture in the gait cycle is being loaded into IPG 210, while IPG 210 is providing stimulation according to the current stimulation partiture in the gait cycle.

As an additional example, external controller 230 can receive instructions from programmer 240 that specify a stimulation partiture for mitigation of autonomic dysreflexia. The instructions can also specify an execution relationship: that this stimulation partiture be provided to IPG 210 if the blood pressure of the patient exceeds a certain threshold level.

Consistent with disclosed embodiments, external controller 230 can include a user interface. A patient can interact with the user interface to cause external controller 230 to perform certain actions. In some embodiments, these actions can depend on the instructions received by external controller 230 from programmer 240. For example, the patient can cause external controller 230 to provide stimulation partitures received from programmer 240 to IPG 210. In some embodiments, these actions can depend on the state of IPG 210. For example, the patient can cause external controller 230 to instruct IPG 210 to execute (or cease execution of) a stimulation partiture loaded onto IPG 210.

The disclosed embodiments are not limited to any particular user interface implementation. In some embodiments, the user interface can be or include a graphical user interface (e.g., a screen, touchscreen, or the like), an audio user interface, a mechanical user interface (e.g., pushbutton(s), switch(es) or the like), or other suitable user interfaces.

Consistent with disclosed embodiments, programmer 240 can be configured to enable a user to create or arrange stimulation partitures for a patient. In some embodiments, creation of a stimulation partiture can include the selection or adjustment of spatial and temporal parameters for stimulation. Such selection or adjustment can include the selection or adjustment of stimulation channels used, the mapping stimulation channels to particular electrodes in the patient, or the timing of stimulation on different stimulation channels. Such selection or adjustment can further include the selection or adjustment of stimulation parameters. In some embodiments, creation of a stimulation partiture can involve using another stimulation partiture as a template or basis. The other stimulation partiture can be a default stimulation partiture, a stimulation partiture used by another patient, or a stimulation partiture previously used by the current patient. Creation of the stimulation partiture for the current patient can include obtaining and adjusting the other stimulation partiture. The other stimulation partiture can be obtained from another device (e.g., external controller 230, IPG 210, a database, another programmer, or the like).

In some embodiments, arrangement of stimulation partitures can include the creation of execution relationships among stimulation partitures. In some instances, a user can interact with programmer 240 to create a sequence of stimulation partitures that are executed sequentially by IPG 210. In some instances, a user can interact with programmer 240 to associate conditions with the execution of the stimulation partiture. In various embodiments, programmer 240 can associate stimulation partitures with user interface elements of external controller 230 (e.g., pushbuttons or toggles), such that a patient interaction with the user interface elements can cause execution of the stimulation partiture.

As may be appreciated, programmer 240 can provide instructions configuring external controller 230. Such instructions can include stimulation partitures and execution relationships. Furthermore, in some embodiments, programmer 240 can provide instructions directly to IPG 210. These instructions can include instructions to IPG 210 to load a stimulation partiture, modify or delete a stimulation partiture, enable or disable a stimulation channel of IPG 210, start or cease execution of a loaded stimulation partiture, or the like. In this manner, a user can interact with programmer 240 to determine appropriate stimulation partitures for a patient. Once the stimulation partitures are determined, the user can transmit the determined stimulation partitures (and any execution relationships) to external controller 230. The patient (or a user) can then interact with external controller 230 to cause IPG 210 to provide the intended stimulation.

Figure 3:
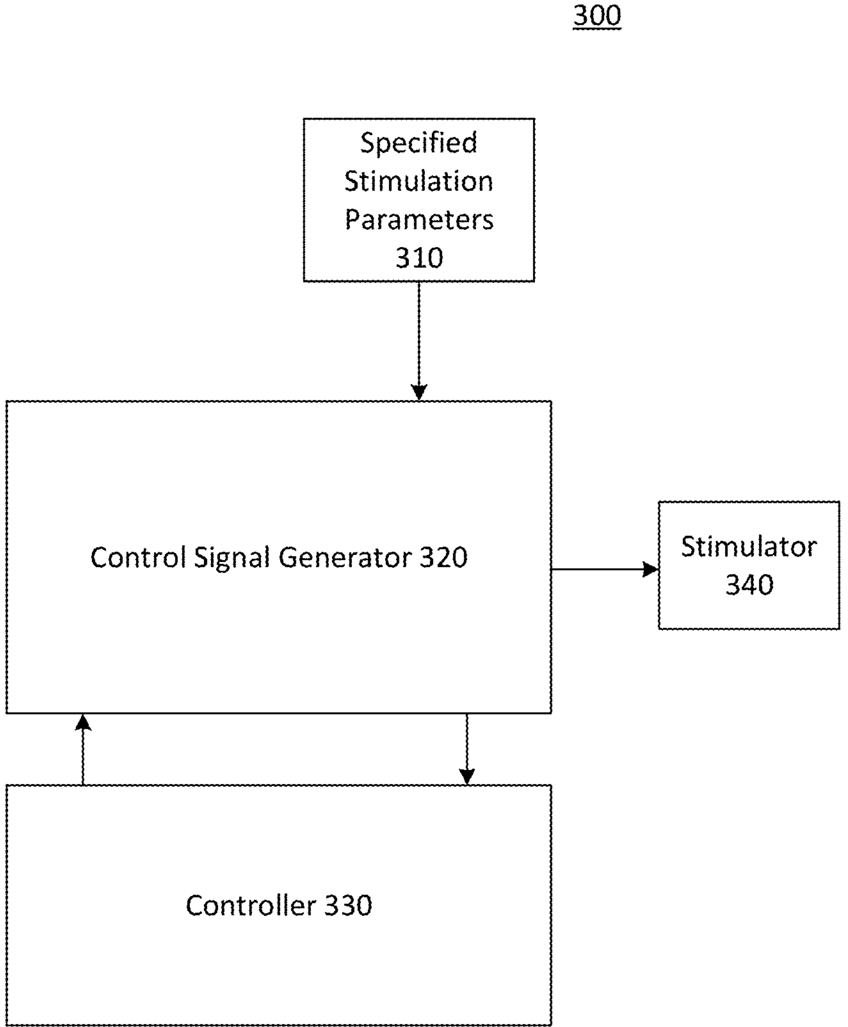
FIG. 3 depicts exemplary components of a pulse generation system configured to generate sets of consistent pulse schedules, consistent with disclosed embodiments.

FIG. 3 depicts exemplary components of a pulse generation system 300 configured to generate sets of consistent pulse schedules, consistent with disclosed embodiments. In some embodiments, pulse generation system 300 can include a control signal generator 320, a controller 330, and a stimulator 340. Control signal generator 320 and controller 330 can form a control loop used to generate control signals for a stimulation partiture. The control signals are generated using one or more stimulation parameter distributions based on specified stimulation parameters 310. The control loop shapes the stimulation parameter distributions to reduce conflicts between control signals. The control signals can be provided to stimulator 340, which can convert the control signals into stimulation signals for provision to the patient. For convenience of description, the disclosed embodiments are described with respect to inter-pulse interval distributions. However, other stimulation parameters can be controlled according to the disclosed systems and methods to reduce conflicts between control signals. For example, pulse duration (and optionally pulse amplitude) can also be controlled to reduce conflicts between control signals. As an additional example, inter-burst interval (or the number of repeats in a burst) can also be controlled to reduce conflicts between control signals.

Consistent with disclosed embodiments, IPG 210 can be or include pulse generation system 300 (or components thereof). For example, stimulator 340 can be or include the stimulator of IPG 210 described above with regards to FIG. 2. Likewise, control signal generator 320 and controller 330 can be implemented by the control circuity of IPG 210 described above with regards to FIG. 2.

Consistent with disclosed embodiments, specified stimulation parameters 310 can concern stimulation characteristics of control signals (or equivalently stimulation channels corresponding to control signals) for a stimulation partiture. In some embodiments, the specified stimulation parameters 310 can be or include parameters defining, at least in part, stimulation parameter distributions. For convenience of description, stimulation parameter distributions are described as being normal distributions. Such distributions can be defined by a mean and a standard deviation. In some embodiments, the specified pulse parameters can be or include mean values for the stimulation parameter distributions. In some embodiments, the specified pulse parameters can include standard deviations for the stimulation parameter distributions.

However, the disclosed embodiments are not so limited. The stimulation parameter distribution need not be a normal distribution. For example, alternative distributions can include log-normal distributions, binomial distributions, f-distributions, Poisson distributions, gamma distributions, or other suitable distributions. In some embodiments, the specified pulse parameters for a distribution can be or include the expected value of the distribution (or one or more parameters that define the expected value of the distribution). In some embodiments, the specified pulse parameters for a distribution can be or include a spread describing the shape of the distribution around the expected value (e.g., a variance, standard deviation, second and/or higher order moment of the distribution, or the like).

As described herein, the specified pulse parameters can describe target values for the control signals. The stimulation characteristics of an individual pulse on a stimulation channel may not match the specified pulse parameters. However, consistent with disclosed embodiments, the average stimulation characteristics over multiple pulses on the stimulation channel can converge on the specified pulse parameters for that stimulation channel.

Consistent with disclosed embodiments, generator 320 can be configured to generate control signals for a stimulation partiture. The control signal for a stimulation partiture can be, include, or specify a pulse schedule that describes the stimulation amplitude of a stimulation channel as a function of time. A pulse schedule for a stimulation channel in a stimulation partiture can be generated by sampling a stimulation parameter distribution associated with that stimulation channel. The sampling can generate one or more stimulation parameter values. For example, when the stimulation parameter distribution describes inter-pulse intervals, the sampling can generate an inter-pulse interval value. As an additional example, when the stimulation parameter distribution describes pulse durations, the sampling can generate a pulse duration value. Generator 320 can then create a pulse schedule using the sampled values. As may be appreciated, the pulse schedule can be defined by many values, of which only a subset may be sampled. For example, a pulse schedule for a biphasic stimulation pulse may be described by an inter-pulse interval, a first phase duration, a first phase amplitude, an interphase interval, a second phase duration, and a second phase amplitude. Of these values, in this example, only the inter-pulse interval may be a sampled value. Alternatively, the inter-phase interval and a phase duration value can be sampled. In some embodiments, the remaining values can be specified as part of the stimulation partiture, received from another device (e.g., external controller 230 or programmer 240), or be default values.

Consistent with disclosed embodiments, generator 320 can construct the pulse schedule according to the sample values (and using any other relevant values). For example, when the inter-phase interval and a phase duration value are sampled, generator 320 can use these values to determine other related values of the pulse sequence. For example, the first phase duration and the second phase duration can be generated from the sampled phase duration value according to predetermined rules or formula (e.g., the phase durations may be equal, the second phase duration can be some multiple of the first phase duration, the first and second phase durations can exhibit some suitable relationship, or the like). The first phase amplitude can then be determined from the first phase duration (e.g., using a strength-duration curve, or the like). The second phase amplitude can then be determined using the first phase amplitude and the first and second phase durations (e.g., according to charge balancing principles, or the like).

Consistent with disclosed embodiments, generator 320 can determine whether the generated pulse schedule is consistent with other pulse schedules for the stimulation partiture. In some embodiments, generator 320 can compare the generated pulse schedule to other pulse schedules. The comparison can depend on one or more rules. The rules can specify temporal and/or spatial conflicts. In some embodiments, two pulse schedules can be temporally inconsistent when the two pulse schedules have temporally overlapping, or nearly overlapping pulses. A first pulse of a first pulse schedule can be overlapping with a second pulse of a second pulse schedule when the first pulse ends after the second pulse begins. In some embodiments, the first pulse can be nearly overlapping with the second pulse when the time difference between the ending time of the first pulse and the beginning time of the second pulse is less than a tolerance value (e.g., 1000 microsecond, 100 microseconds, 10 microseconds, or some other value, which may depend on the characteristics of the stimulator). In some embodiments, two pulse schedules can be spatially inconsistent when the two pulse schedules have spatially overlapping, or nearly overlapping pulses. In some embodiments, the other pulse schedules may have been created prior to this pulse schedule. In various embodiments, the other schedules may be created at the same time or created after the generated pulse schedule.

Consistent with disclosed embodiments, when the pulse schedules for the stimulation partiture are consistent, generator 320 can provide corresponding control signals to stimulator 340. In some embodiments, when a pulse schedule is inconsistent with another pulse schedule, generator 320 can recreate all of the pulse schedules. In various embodiments, only one (or both) of the inconsistent pulse schedules are recreated. After recreating one or more of the pulse schedules, generator 320 can repeat the consistency check. This cycle of consistency checking and pulse schedule recreation can be repeated until a consistent set of pulse schedules is generated.

As may be appreciated, in some instances a tradeoff may exist between the difficulty of generating consistent pulse schedules and the fidelity of the generated pulse schedules to the specified pulse parameters. As a simple example, two stimulation channels having similar inter-pulse intervals (e.g., 100 Hz and 101 Hz) may exhibit inconsistent pulse schedules for prolonged intervals (e.g., when they are in phase). Similarly, the two stimulation channels may exhibit consistent pulse schedules for prolonged intervals (e.g., when they are out of phase).

Consistent with disclosed embodiments, pulse generation system 300 can use feedback control to adapt the stimulation parameter distributions. In some embodiments, such feedback control can automatically configure generator 320 to manage the tradeoff between generating consistent pulse schedules and fidelity of the generated pulse schedules to the specified pulse parameters. To continue the prior, two-stimulation channel example, generator 320 can be configured to provide a broader spread (or even different expected value) of sampled stimulation parameter values around the specified pulse parameter values during intervals in which the two stimulation channels are inconsistent. Similarly, generator 320 can be configured to provide a narrower spread of sampled stimulation parameter values around the specified stimulation parameter values during intervals in which the two stimulation channels are consistent.

In some embodiments, generator 320 can provide detection parameter(s) to controller 330. In some embodiments, the detection parameter(s) can indicate the difficulty in generating consistent pulse schedules. In some such embodiments, the detection parameter(s) can indicate the number of attempts required to generate a consistent set of pulse schedules. In some embodiments, the detection parameter(s) can indicate the fidelity of the generated pulse schedules to the specified pulse parameters. In some such embodiments, the detection parameter(s) can indicate the differences between the sampled stimulation parameter values and the specified stimulation parameter values. For example, when the specified stimulation parameter is the inter-pulse interval, the detection parameter(s) can include a vector of differences between the sampled and specified inter-pulse intervals for the generated consistent set of pulse schedules. As may be appreciated, such a vector could likewise be generated for other stimulation characteristics. Likewise, a multi-column matrix could capture differences between sampled and specified parameter values for multiple parameters. Such a vector or matrix is referred to herein as a "jitter matrix."

Consistent with disclosed embodiments, controller 330 can be configured to generate an update signal for the stimulation parameter distributions maintained by generator 320. The update signal can depend on the detection parameter(s) received from generator 320. In some embodiments, controller 330 can be configured to balance the ability of generator 320 to generate consistent pulse schedules and the fidelity of the generated pulse schedules. In some embodiments, controller 330 can combine a controller and an estimator or observer. The estimator or observer can be configured to determine a state of generator 320. The controller can then generate the update signal based on the determined state of generator 320.

Consistent with disclosed embodiments, the state of generator 320 can describe the present ability of generator 320 to generate consistent pulse schedules. As may be appreciated, the detection parameter(s) received from generator 320 following successful generation of a set of consistent pulse schedules may only indicate the difficulty of generating that particular set of consistent pulse schedules. The estimator or observer can use this particular sample (and optionally previously received detection parameter(s) for previously generated sets of consistent pulse schedules) to generate a general estimate of the present difficulty of generating sets of consistent pulse schedules.

In some embodiments, the difficulty of generating sets of consistent pulse schedules can be characterized by a distribution of the number of attempts required to generate a set of consistent pulse schedules. The particular number of attempts required to create the most recent consistent set of pulse schedules can be treated as a sample drawn from that distribution. The estimator or observer can estimate one or more parameters characterizing that distribution. These estimated parameters can then describe (at least in part) the state of the system.

Consistent with disclosed embodiments, the state of generator 320 can describe the fidelity of pulse schedules generated by generator 320. As may be appreciated, the detection parameter(s) received from generator 320 following successful generation of a set of consistent pulse schedules may only indicate the fidelity of that pulse schedule. The estimator or observer can use this particular sample (and optionally previously received detection parameter(s) for previously generated sets of consistent pulse schedules) to generate a general estimate of the present fidelity of pulse schedules generated by generator 320.

In some embodiments, the fidelity of pulse schedules generated by generator 320 can be characterized by at least one of error term(s) (e.g., a function or weighted function of differences between sampled and specified stimulation parameter values) or sampled stimulation parameter distribution(s). In various embodiments, the error terms or sampled stimulation parameter distributions can be per stimulation channel. In various embodiments, the error terms or sampled stimulation parameter distributions can be combined across stimulation channels. In some embodiments, the sampled stimulation parameter distributions can be probability distributions. The state of generator 320 can then include parameters describing these probability distributions. In some embodiments, the state of generator 320 can include the error term(s).

The disclosed embodiments are not limited to any particular observer or estimator architecture. In some embodiments, the observer or estimator can be a Kalman Filter (or another suitable linear or nonlinear state estimator). In some embodiments, the observer or estimator can be chosen based on an assumed type of the difficulty distribution (or sampled stimulation parameter distributions). For example, the difficulty distribution can be assumed to be an exponential distribution. An exponential distribution is characterized by a single rate parameter, which is the inverse of the expected value of the exponential function. The received detection parameter(s) can be used to generate an estimate of the single rate parameter (e.g., using an average or weighted average, such as recency-weighted average, or the like). The rate parameter can then be taken as the state of generator 320 (at least with regards to the difficulty of generating sets of consistent pulse schedules).

Consistent with disclosed embodiments, controller 330 can include a controller configured to generate an update signal based on the determined state of generator 320. The disclosed embodiments are not limited to any particular controller or control law. In some embodiments, the controller can be a proportional controller, a proportional integral controller, a proportional integral derivative controller, or the like. In some embodiments, the controller can be implemented by using a fixed mapping of states to update levels (e.g., using thresholds and if-then logic, hash coding, or another suitable implementation). In some embodiments, the controller can be implemented using a machine learning model, such as a random forest or neural network.

Consistent with disclosed embodiments, stimulator 340 can be configured to transform control signals received from generator 320 into stimulation suitable for provision to a patient. In some embodiments, stimulator 340 can be configured to receive pulse schedules and provide corresponding voltage-controlled or current-controlled electrical stimulation outputs.

Figure 4:
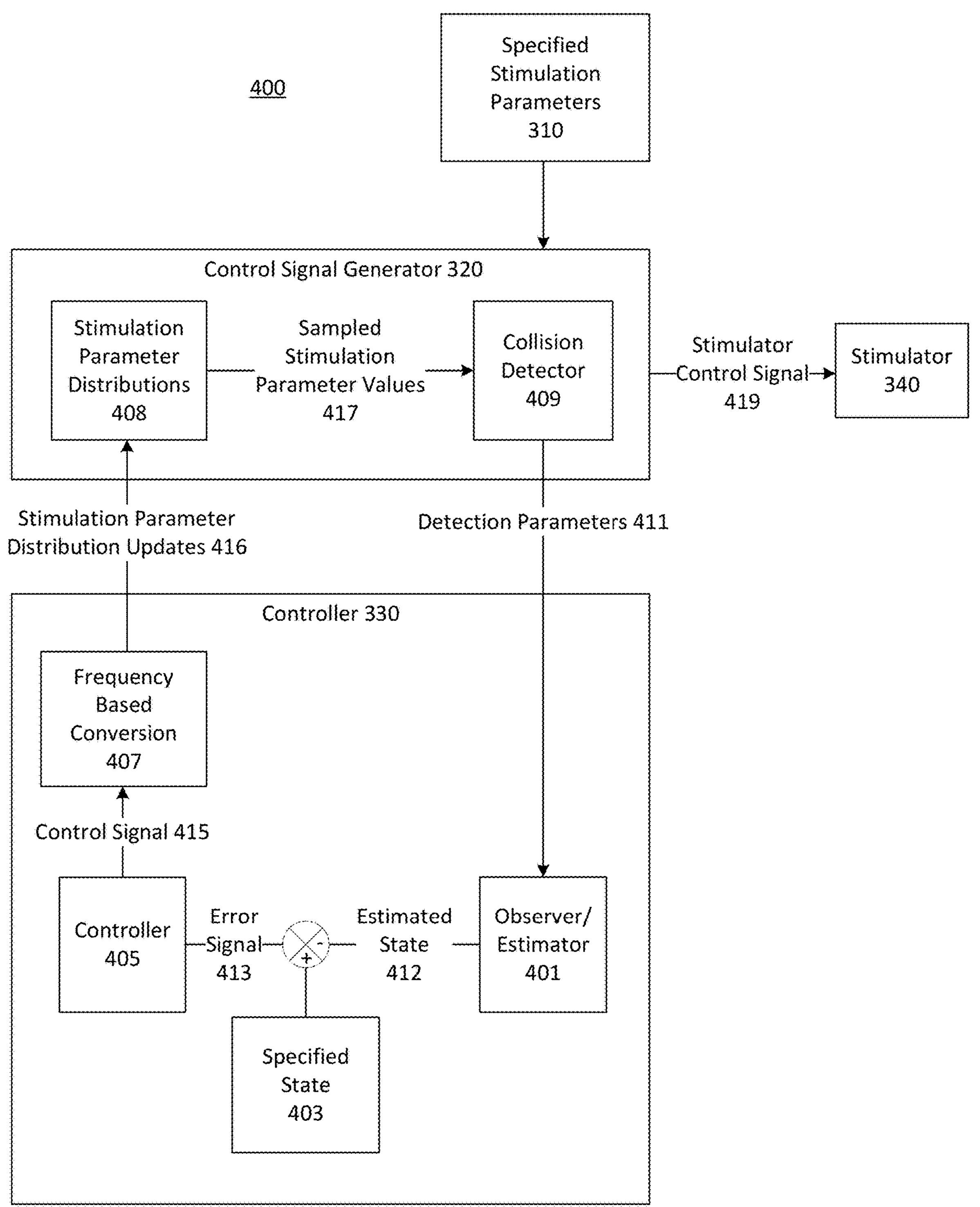
FIG. 4 depicts an exemplary pulse generation system, consistent with disclosed embodiments.

FIG. 4 depicts an exemplary pulse generation system 400, consistent with disclosed embodiments. Pulse generation system 400 can be an implementation of pulse generation system 300, described above with regards to FIG. 3. As described above with regard to FIG. 3, control signal generator 320 can be configured to produce a control signal (e.g., stimulator control signal 419). Control signal generator 320 and controller 330 can form a feedback loop in which controller 330 generates updates (e.g., stimulation parameter distribution updates 416) in response to detection parameters provided by control signal generator 320.

Consistent with disclosed embodiments, pulse generation system 400 can be configured to control inter-pulse intervals to prevent different stimulation channels from having overlapping stimulus pulses. However, as described herein, pulse generation system 400 can be configured to control other stimulation parameters. Pulse generation system 400 can be configured to model inter-pulse intervals using normal distributions. However, as described herein, pulse generation system 400 can be configured to model stimulation parameters using other probability distributions.

Consistent with disclosed embodiments, pulse generation system 400 can be configured to control the difficulty of generating sets of consistent pulse schedules. The difficulty of generating sets of consistent pulse schedules can be characterized in terms of the number of attempts required to generate a consistent pulse schedule. As may be appreciated, other measures of the difficulty of generating consistent pulse schedule may also be used.

Consistent with disclosed embodiments, pulse generation system 400 may not expressly control fidelity of the generated sets of pulse signals. Instead, pulse generation system 400 can be configured to target a particular level of difficulty in generating sets of consistent pulse schedules. In such embodiments, control of fidelity can be achieved indirectly, through the selection of the difficulty target (e.g., as fidelity and control signal generation difficulty can have inverse relationship). However, as may be appreciated, fidelity can also be controlled directly (e.g., making the control law used to generate the update dependent on a measure of fidelity).

Consistent with disclosed embodiments, observer/estimator 401 can be configured to estimate a state of control signal generator 320. Observer/estimator 401 can estimate this state using detection parameters 411. In some embodiments, detection parameters 411 can include a number of attempts required to generate the most recent set of consistent pulse schedules. In some embodiments, pulse generation system 400 can assume that the number of attempts follows a particular distribution type and estimate values for parameter(s) of that distribution. The estimated values can be, or be used to, generate the state.

In some embodiments, observer/estimator 401 can assume that the difficulty distribution is an exponential distribution. As may be appreciated, in some instances the empirical distribution may be closer to a geometric progression. However, the probability distribution for a geometric progression may be difficult to model.

Observer/estimator 401 can update an estimated expected value for the number of attempts required to generate a set of consistent pulse schedules. For example:

$$\lambda_i^{-1} = (1-\alpha)\lambda_{i-1}^{-1} + \alpha n_i$$

where $\lambda_i$ is the estimated rate parameter for the exponential distribution, $\lambda_{i-1}$ is the prior estimate of the rate parameter for the exponential distribution, $n_i$ is the number of attempts required to generate the current set of consistent pulse schedules, and $\alpha$ is a weighting parameter between 0 and 1. The larger $\lambda$, the more weight the system will place on recent numbers of attempts.

In some embodiments, estimated state 412 can be $\lambda_i$. In such embodiments, specified state 403 can be a target rate parameter $\lambda_{target}$. Error signal 413 can then be the difference between $\lambda_{target}$ and $\lambda_i$.

In some embodiments, estimated state 412 can depend on the cumulative density function of the estimated distribution, evaluated for the most recent number of attempts. For example, assuming an exponential distribution:

$$S_i = P(N \le n_i; \lambda_i) = 1 - e^{-\lambda_i n_i}$$

Where $S_i$ is the estimated state.

The state formula may be adjusted to account for the empirical attempt distribution being zero for values of n less than 1 (e.g., unlike a conventional exponential distribution). In some embodiments, for example, $n_i$ can be replaced with:

$$x = n_i - y$$

where y is an offset.

When estimated state 412 is expressed in terms of a cumulative density function, specified state 403 can be similarly expressed. For example, assuming an exponential distribution:

$$S_{target} = P(N \le n_i; \lambda_{target}) = 1 - e^{-\lambda_{target} n_i}$$

where the specified state 403 is defined in terms of a specified rate parameter $\lambda_{target}$. $S_{target}$ can be adjusted using an offset, as described above with regards to $S_i$. In some embodiments, error signal 413 can depend on the difference between $S_i$ and $S_{target}$. In various embodiments, error signal 413 can further depend on a difference between the number of attempts and an offset:

$$e_i = (n_i - y)(S_{target} - S_i)$$

where $e_i$ is the error signal and y is a specified offset, as described above.

Consistent with disclosed embodiments, pulse generation system 400 can be configured to use controller 405 and frequency-based conversion 407 to generate stimulation parameter updates 416 from error signal 413.

In some embodiments, when using a control architecture in which the present output depends, at least in part, on prior error values, controller 405 can include anti-windup control. Such anti-windup control can prevent or reduce overshoot arising from sudden changes in the error signal. In some embodiments, the anti-windup control can limit or cap the contribution from prior error signal values. For example, when using integral control, the integral error term can accumulate the error signal:

$$k_i = k_{i-1} + e_i$$

where $k_i$ is the present integral error term, $k_{i-1}$ is the prior integral error term, and $e_i$ is the present error signal. The anti-windup control can cap the value of $k_i$ to some predetermined value $k_{max}$.

Consistent with disclosed embodiments, controller 405 can be configured to implement a proportional, proportional integral, or proportional integral derivative control law. For example, controller 405 can implement the following control law:

$$u_i = pe_i + d_i + k_i$$

where $u_i$ is the output of controller 405 (e.g., control signal 415, or the like), p is a proportional control coefficient, $d_i$ is a term based on the derivative of the error signal $e_i$ with respect to time, and $k_i$ is the integral error term described above.

Consistent with disclosed embodiments, controller 405 can be configured to further filter the output. Such filtering can smooth the output and provide an additional degree of configurability of system 400. For example, $$u_i = \alpha u_{i-1} + (1-\alpha)u_i$$

where $u_{i-1}$ is the prior output of controller 405 and $\alpha$ is a weighting coefficient between zero and one. In some embodiments, bounds can be imposed on $u_i$, depending on the physical significance of this parameter. For example, when $u_i$ corresponds to a spread in a stimulation parameter distribution, a lower bound can be imposed on $u_i$ (e.g., $u_i=\max(u_{min}, u_i)$, where $u_{min}\geq 0$), as a negative variance can lack physical meaning.

As may be appreciated, controller 405 is not limited to the above controller architecture. In various embodiments, controller 405 can use another, suitable controller architecture.

Consistent with disclosed embodiments, frequency-based conversion 407 can be configured to convert the control signal 415 into stimulation parameter distribution updates 416. In some embodiments, this conversion can depend on specified simulation parameters 310. For example, the stimulation parameter distribution update for a stimulation channel can be the product of a scaling factor and the control signal. The scaling factor can depend on at least one specified stimulation parameter(s) for the stimulation channel (e.g., one or more of specified simulation parameters 310).

Consistent with disclosed embodiments, the specified simulation parameters 310 can include specified inter-pulse intervals for the stimulation channels (or specified stimulation frequencies). The scaling factor for a channel can depend on the specified inter-pulse interval for the stimulation channel. In some embodiments, the specified inter-pulse interval for the stimulation channel can be normalized. The normalization factor can be the sum of the specified inter-pulse intervals for some or all of the stimulation channels:

$$p_{ij} = u_i\mu_j \Big/ \sum_j \mu_j$$

where $p_{ij}$ is the $i^{th}$ update of the $j^{th}$ stimulation channel and $\mu_j$ is the specified mean inter-pulse interval for the $j^{th}$ stimulation channel.

Consistent with disclosed embodiments, controller 330 can provide the stimulation parameter distribution updates 416 to control signal generator 320. As described herein, control signal generator 320 can be configured to maintain stimulation parameter distributions 408. Stimulation parameter distributions 408 can specify stimulation distribution parameters for stimulation channels.

Consistent with disclosed embodiments, a stimulation channel can be associated with a number of stimulation distribution parameters. The number of stimulation parameters associated with the stimulation channel can depend on the number of stimulation parameters sampled for that stimulation channel. The number of stimulation parameters associated with the stimulation channel can also depend on the type of distribution from which the stimulation parameters are drawn. For example, when the stimulation amplitude and inter-pulse interval are sampled for a stimulation channel, two stimulation parameter distributions can be associated with that stimulation parameter. When these two stimulation parameter distributions are modeled as normal distributions, each can have a mean and a variance. Four stimulation distribution parameters can therefore be associated with the stimulation channel (two means and two variances). Other stimulation parameter distribution model type may require fewer (e.g., exponential models) or more (e.g., Weibull models) stimulation parameters.

Consistent with disclosed embodiments, a stimulation distribution parameter can be associated with multiple stimulation channels. For example, multiple stimulation channels may draw stimulation amplitude parameters specified by the same parameters (e.g., for normal distributions, the same mean and variance, or potentially differentially scaled versions of the same mean and variance).

In some embodiments, stimulation parameter distribution updates 416 can affect a subset of the stimulation distribution parameters associated with a stimulation channel. For example, when a stimulation parameter distribution for a stimulation channel is modeled as a normal distribution, the stimulation parameter distribution updates may affect only the variance parameter of normal distribution.

In some embodiments, stimulation parameter distribution updates 416 can affect a subset of the stimulation channels. For example, stimulation parameters for one or more protected channels may not be updated by controller 330. In some embodiments, a protected channel can have predetermined stimulation parameter distribution(s). In some embodiments, all the stimulation parameters for a protected channel can be deterministic (e.g. not drawn from a distribution).

Consistent with disclosed embodiments, stimulation parameter distributions 408 can include stimulation parameters specifying an inter-pulse interval distribution for each stimulation channel. In some embodiments, these inter-pulse interval distributions can be modeled as normal distributions. The means of these normal distributions can be specified (e.g., by specified stimulation parameters 310). The variances these normal distributions can be updated using stimulation parameter distribution updates 416:

$$\sigma_{ij} = \sigma_{i-1,j} + p_{ij}$$

where $\sigma_{ij}$ is the $i^{th}$ update of the variance for the $j^{th}$ stimulation channel, $\sigma_{i-1,j}$ is the prior update of the variance for the $j^{th}$ stimulation channel, and $p_{ij}$ is the $i^{th}$ update of the $j^{th}$ stimulation channel. The updated stimulation parameter distributions for the $j^{th}$ stimulation channel can then be $\mathcal{N}(\mu_j, \sigma_{ij})$.

Consistent with disclosed embodiments, sampled pulse parameters 418 can be drawn from the updated stimulation parameter distributions 408. Control signal generator 320 can be configured to generate pulse schedules using stimulation parameters including the sampled pulse parameters.

Consistent with disclosed embodiments, collision detector 409 can be configured to determine when pulse schedules for different stimulation channels have overlapping stimulus pulses. Such inconsistent pulse schedules can be rejected and control signal generator 320 can generate another pulse schedule using sampled pulse parameters 418.

Consistent with disclosed embodiments, control signal generator 320 can be configured to track the number of attempts required to generate a consistent set of pulse schedules. This number can be provided to controller 330 in detection parameters 411. In this manner, the control loop can be closed.

Consistent with disclosed embodiments, control signal generator 320 can provide stimulator control signal 419 to stimulator 340. Stimulator control signal 419 can specify the consistent set of pulse schedules generated by control signal generator 320 using the sampled pulse parameters 418. Stimulator 340 can generate stimulation for the patient in accordance with the stimulator control signal 419.

In some embodiments, stimulator control signal 419 can indicate only the current control signal value for a stimulation channel, even when the set of pulse schedules includes a future pulse for that stimulation channel. For example, a pulse schedule may indicate that a stimulation channel is currently not outputting a stimulation pulse, but will output a stimulation pulse in 10 ms. In this example, stimulator control signal 419 may only indicate that the stimulation channel is currently not outputting a stimulation pulse. In 10 ms, the value of stimulator control signal 419 may change, to indicate that the stimulation channel should output a stimulation pulse. Consistent with disclosed embodiments, stimulator control signal 419 may indicate only the current control signal value for a stimulation channel because the future stimulation pulse timings may change, as inconsistent pulse schedules are discarded or revised. In such embodiments, stimulator 340 can be configured to provide stimulation for the simulation channels according to the current control signal values.

In some embodiments, stimulator control signal 419 can provide information about current and future stimulation channel values. For example, a pulse schedule may indicate that a particular stimulation channel is currently not outputting a stimulation pulse, but will output a stimulation pulse in 10 ms. In this example, stimulator control signal 419 may indicate both that (i) the particular stimulation channel is currently not outputting a stimulation pulse, and (ii) the particular stimulation channel will output a stimulation pulse in 10 ms. In such embodiments, should control signal generator 320 subsequently generate a new set of pulse schedules (e.g., having a different pulse timing for the particular stimulation channel), control signal generate 320 will provide that new pulse schedule to stimulator 340. In such embodiments, stimulator 340 can be configured to determine which set of pulse schedules is applicable (e.g., the most recently received). Stimulator 340 can then provide stimulation according to that set of pulse schedules.

FIG. 5A to 5F depicts stages in the generation of an exemplary stimulation partiture, consistent with disclosed embodiments. The exemplary stimulation partiture can include three stimulation channels 501 to 505. Each of the three pulse schedules depicted in FIGS. 5A to 5F can correspond to one of these stimulation channels (e.g., a first pulse schedule can correspond to stimulation channel 501, a second pulse schedule can correspond to stimulation channel 503, and a third pulse schedule can correspond to stimulation channel 505). The pulse schedules may have been generated by control signal generator (e.g., control signal generator 320) using sampled stimulation parameter values (e.g., sampled stimulation parameter values 417). In this simple example, a control signal is depicted as a time series having either the value "low" or the value "high." The value "low" can correspond to the absence of a stimulation pulse, and the value "high" can correspond to the presence of a stimulation pulse. Solid lines indicate control signals values in the past, while broken lines depict the future pulse schedules. As may be appreciated, other control signal implementations (e.g., using absolute or relative pulse start and stop times, pulse countdown timer values, or the like) can also be used.

In the example depicted in FIG. 5A to 5F, each stimulation parameter is associated with a single stimulation parameter distribution. The stimulation parameter distribution for a stimulation channel is sampled to provide the inter-pulse interval for that stimulation channel. The other stimulation parameters for each channel are specified (e.g., in specified stimulation parameters 310, or the like) and are deterministic. The control signal generator generates pulse schedules for each stimulation channel using the combination of a sampled inter-pulse interval value and the deterministic values of the other stimulation parameters.

Figure 5A:
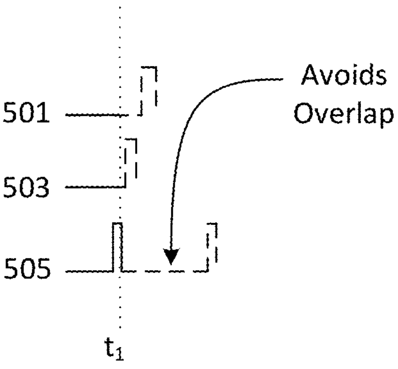
FIG. 5A to 5F depicts stages in the generation of an exemplary stimulation partiture, consistent with disclosed embodiments.

FIG. 5A depicts the stimulation channels and associated pulse schedules at a first time $t_1$. In this example, a scheduled pulse completed at time $t_1$ on stimulation channel 505. In response to completion of this pulse, the control signal generator can generate a new pulse schedule for stimulation channel 505 (shown as a broken line depicting the inter-pulse interval and the next pulse). The control signal generator can generate this new pulse schedule using sampled stimulation parameters for stimulation channel 505. In some embodiments, the sampled stimulation parameters can be reused from the generation of the last set of pulse schedules. In some embodiments, the control signal generator can generate new sampled stimulation parameters by sampling stimulation parameter distributions for stimulation channel 505.

In this example, control signal generator can determine that the scheduled pulse for stimulation channel 505 is consistent with the scheduled pulses for stimulation channels 501 and 503. The control signal generator can therefore output detection parameter values to the controller that indicate that a single attempt was necessary to generate a consistent set of pulse schedules.

Figure 5B:
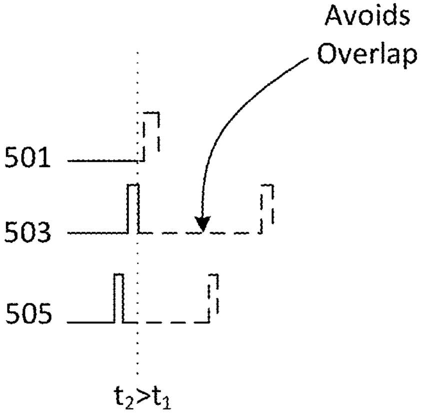

FIG. 5B depicts the stimulation channels and associated pulse schedules at a second time $t_2>t_1$. In this example, a scheduled pulse completed at time $t_2$ on stimulation channel 503. In response to completion of this pulse, the control signal generator can generate a new pulse schedule for stimulation channel 503 (shown as a broken line depicting the inter-pulse interval and the next pulse). The control signal generator can generate this new pulse schedule using sampled stimulation parameters (e.g., reused or newly generated) for stimulation channel 503.

In this example, control signal generator can determine that the scheduled pulse for stimulation channel 503 is consistent with the scheduled pulses for stimulation channels 501 and 505. The control signal generator can therefore output detection parameter values to the controller that indicate that a single attempt was necessary to generate a consistent set of pulse schedules.

Figure 5C:
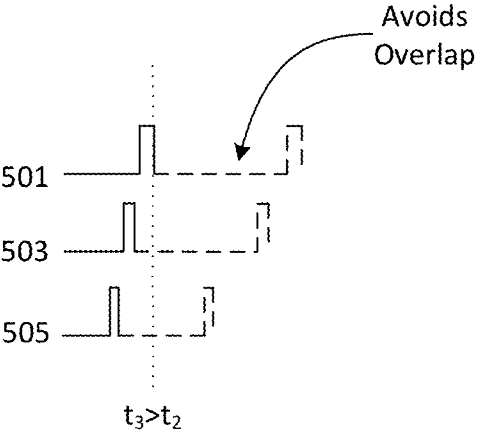

FIG. 5C depicts the stimulation channels and associated pulse schedules at a third time $t_3>t_2$. In this example, a scheduled pulse completed at time $t_3$ on stimulation channel 501. In response to completion of this pulse, the control signal generator can generate a new pulse schedule for stimulation channel 501 (shown as a broken line depicting the inter-pulse interval and the next pulse). The control signal generator can generate this new pulse schedule using sampled stimulation parameters (e.g., reused or newly generated) for stimulation channel 501.

In this example, control signal generator can determine that the scheduled pulse for stimulation channel 501 is consistent with the scheduled pulses for stimulation channels 503 and 505. The control signal generator can therefore output detection parameter values to the controller that indicate that a single attempt was necessary to generate a consistent set of pulse schedules.

Figure 5D:
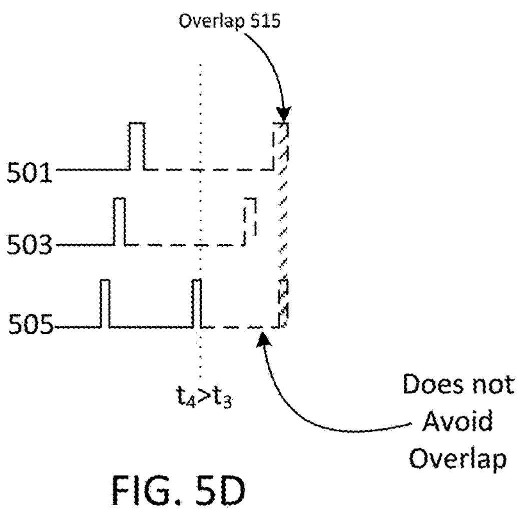

FIG. 5D depicts the stimulation channels and associated pulse schedules at a third time $t_4>t_3$. In this example, a scheduled pulse completed at time $t_4$ on stimulation channel 505. In response to completion of this pulse, the control signal generator can generate a new pulse schedule for stimulation channel 505 (shown as a broken line depicting the inter-pulse interval and the next pulse). The control signal generator can generate this new pulse schedule using sampled stimulation parameters (e.g., reused or newly generated) for stimulation channel 505.

In this example, control signal generator can determine that the scheduled pulse for stimulation channel 505 is inconsistent with the scheduled stimulation pulse for stimulation channel 501. The scheduled stimulation pulse on stimulation channel 501 overlaps with the scheduled stimulation pulse for stimulation channel 505, resulting in overlap 515. The control signal generator can therefore re-attempt generation of a pulse schedule for stimulation channel 505.

Figure 5E:
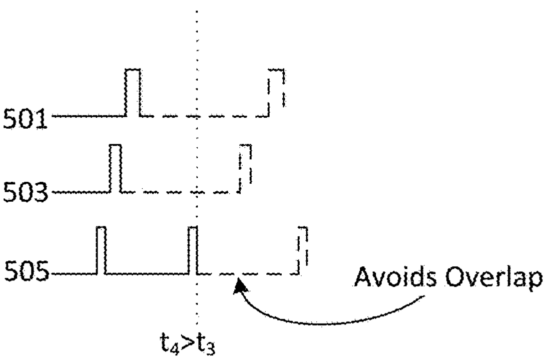

FIG. 5E depicts the stimulation channels and associated pulse schedules at a third time $t_4>t_3$, following a second attempt at generating a pulse schedule for stimulation channel 505. In this example, the control signal generator obtained a new inter-pulse interval by resampling the stimulation parameter distribution for stimulation channel 505. The new inter-pulse interval is longer than the prior inter-pulse interval. As a result, the pulse schedules for stimulation channels 501 and 505 are consistent (e.g., the stimulation pulses no longer overlap). A control signal generator can therefore output detection parameter values to the controller that indicate that two attempts were necessary to generate a consistent set of pulse schedules.

Figure 5F:
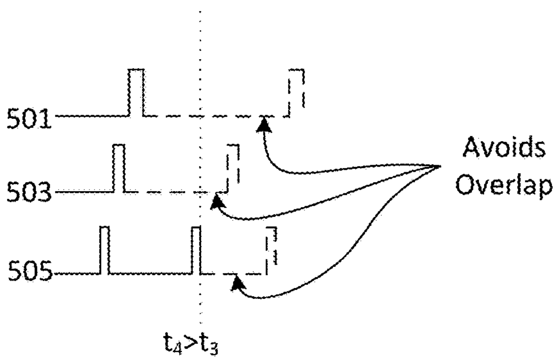

FIG. 5F depicts the stimulation channels and associated pulse schedules at a third time $t_4>t_3$, following a second attempt at generating a pulse schedule for stimulation channel 505. In this example, the control signal generator obtained a new inter-pulse interval by resampling the stimulation parameter distribution for all stimulation channels (e.g., as opposed to only stimulation channel 505). The new inter-pulse intervals for the stimulations differ from those of the prior stimulation channels. As a result, the pulse schedules for stimulation channels 501 and 505 are consistent (e.g., the stimulation pulses no longer overlap). A control signal generator can therefore output detection parameter values to the controller that indicate that two attempts were necessary to generate a consistent set of pulse schedules.

As may be appreciated, when all stimulation channels are updated upon detection of a conflict, an inter-pulse interval of a stimulation channel may be shortened such that the resulting pulse schedule would place the pulse in the past. The control signal generator can be configured to treat sets of pulse schedules that include pulses occurring in the past as inconsistent. In some embodiments, such an inconsistent set of pulse schedules may not contribute to the tracked number of attempts. In some embodiments, the sampled inter-pulse interval for the stimulation channel having the pulse in the past may be resampled. In some embodiments, the sampled inter-pulse intervals for all the stimulation channels may be resampled. In some embodiments, such an In some embodiments, the control signal generator can be configured to generate a new pulse schedule upon completion of a scheduled pulse. In such embodiments, pulse schedules may be generated "as-needed" while stimulation is being provided to the patient. In some embodiments, the control signal generator can be configured to generate pulse schedules for multiple pulses. For example, the pulse generation process depicted in FIG. 5A to 5F can be performed in advance. In such embodiments, the control signal generator can be configured to simulate stimulation over a duration, generating a pulse schedule including many pulses for some or all of the stimulation channels in the stimulation partiture. This multi-pulse, multi-channel pulse schedule can then be replayed to provide the control signal for the stimulator. As may be appreciated, each time this multi-pulse, multi-channel pulse schedule is generated, the pulse timings may differ, due to the stochastic nature of the pulse-to-pulse stimulation parameters. However, the expected values for each stimulation channel will remain close to the specified stimulation parameter values for that stimulation channel.

In some embodiments, a programmer (e.g., programmer 240) or external controller (e.g., external controller 230) can be configured to generate pulse schedules for multiple pulses, according to the embodiments described herein. For example, the control signal generator and controller can be implemented by the programmer or the external controller. The multi-pulse, multi-channel pulse schedule can then be provided to an IPG (e.g., IPG 210), which can use the pulse schedule in providing stimulation to a patient.

Figure 6A:
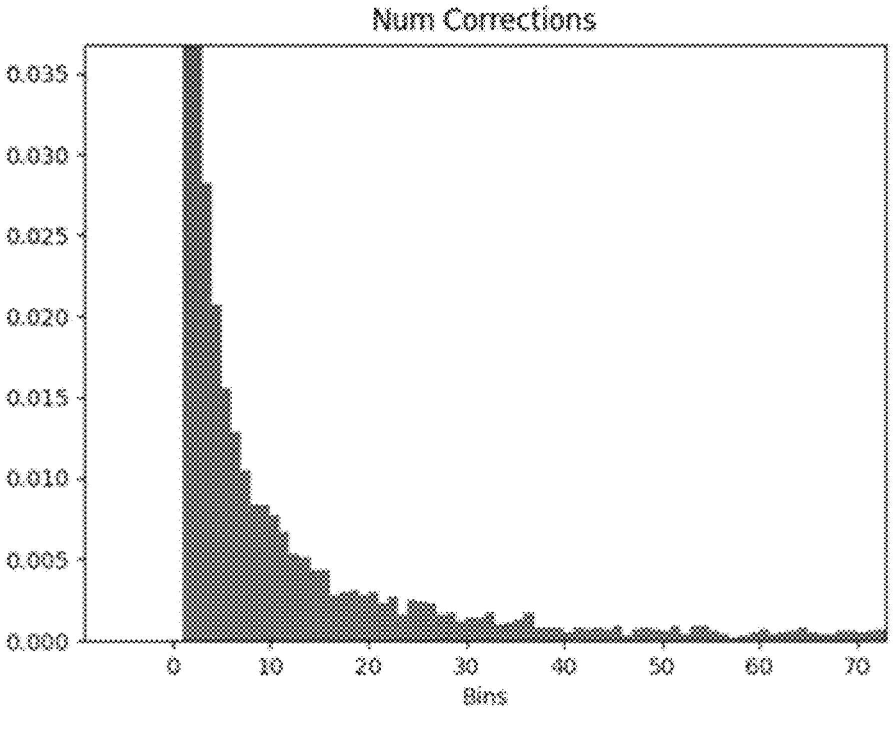
FIG. 6A depicts an exemplary empirical difficulty distribution, consistent with disclosed embodiments.

FIG. 6A depicts an exemplary empirical difficulty distribution, consistent with disclosed embodiments. In this example, the only sampled stimulation parameter was the inter-pulse interval. The stimulation parameter distribution was a normal distribution having a mean and variance. The variance was controlled using the control signal generator and the controller as described in FIGS. 3 and 4. The detection parameter was the number of attempts required to generate a set of consistent pulse schedules. The independent variable in the empirical difficulty distribution is the number of attempts, and the dependent variable is the number of times that number of attempts was required. As shown in FIG. 6A, the empirical difficulty distribution resembles an exponential distribution. As an exponential distribution can be modeled using a single rate parameter, assuming that the empirical difficulty distribution is an exponential distribution can enable state control, with the rate parameter being the controlled state.

Figure 6B:
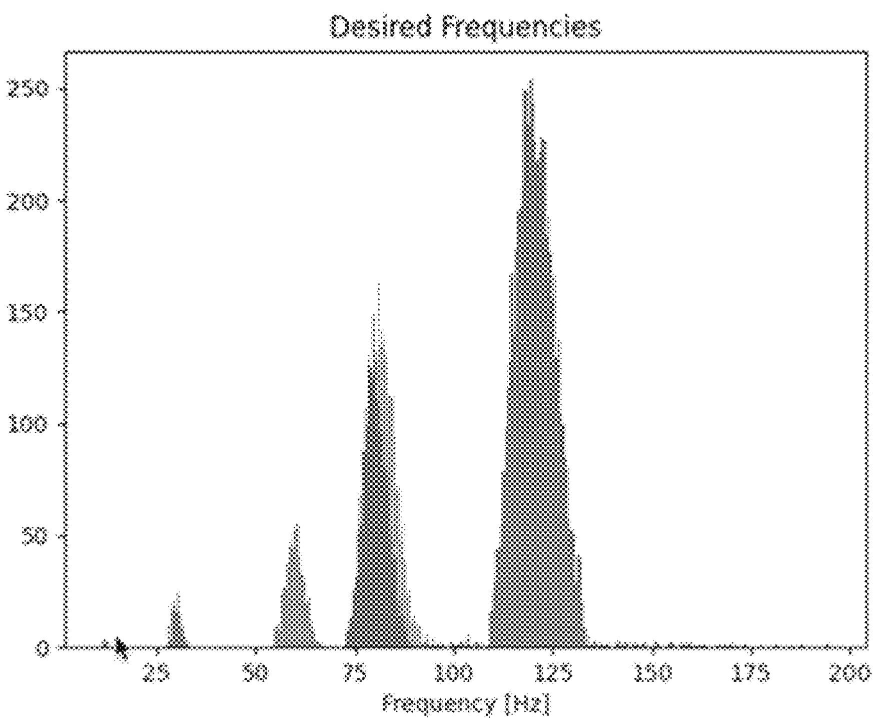
FIG. 6B depicts exemplary empirical stimulation parameter distributions, consistent with disclosed embodiments.

FIG. 6B depicts exemplary empirical stimulation parameter distributions, consistent with disclosed embodiments. In this example, the only sampled stimulation parameter was the inter-pulse interval. The stimulation parameter distribution was a normal distribution having a mean and variance. The variance was controlled using the control signal generator and the controller as described in FIGS. 3 and 4. The independent variable is the reciprocal of the inter-pulse interval for each stimulation pulse output, while the dependent variable is the number of times that an inter-pulse interval falling in a binned range of inter-pulse intervals was output. In the example depicted in FIG. 6B, the stimulation partiture included six stimulation channels. As shown in FIG. 6B, the inter-pulse interval distributions for the six stimulation channels are centered on the specified central frequencies for these channels.

Figure 7:
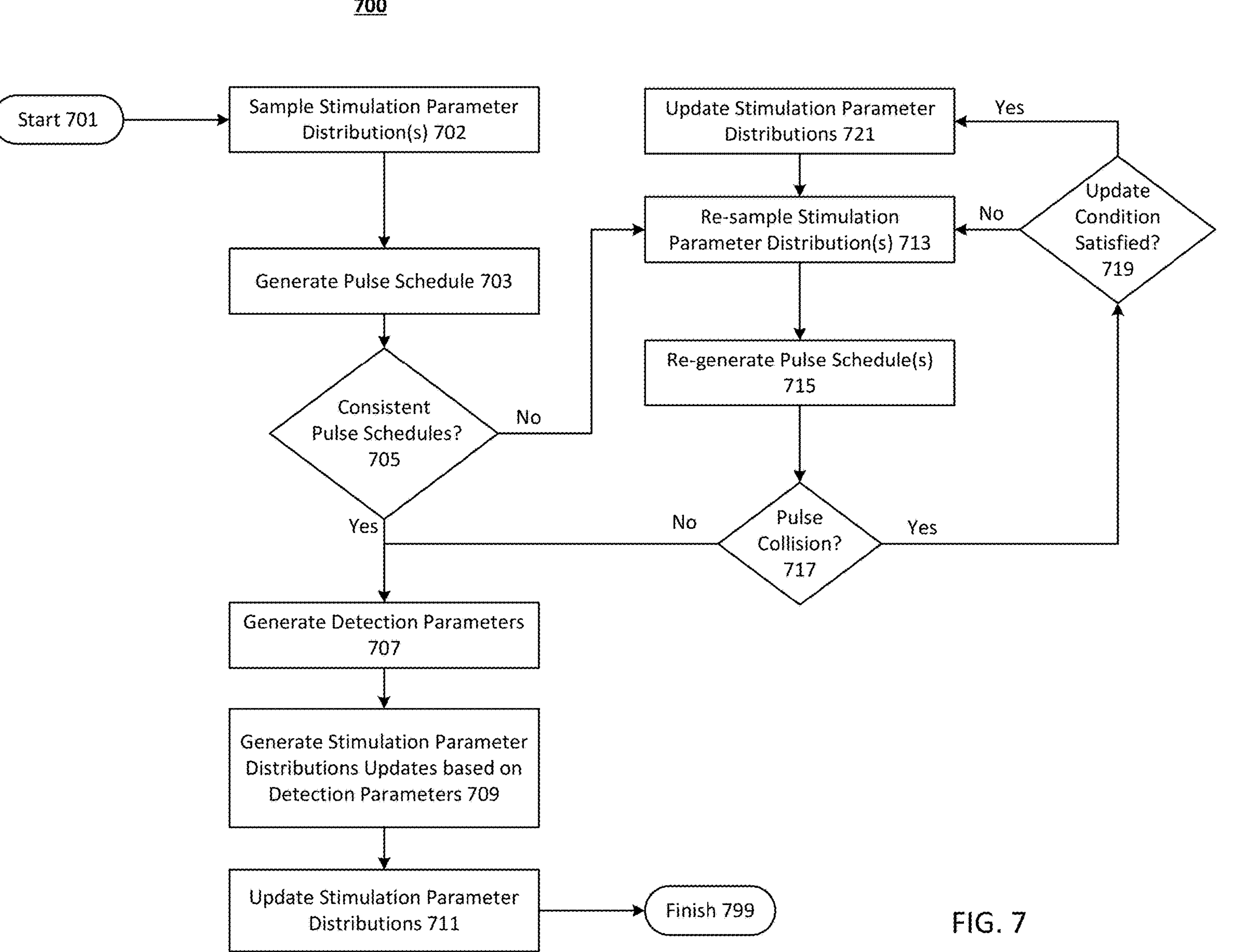
FIG. 7 depicts an exemplary process of stochastic stimulation scheduling, consistent with disclosed embodiments.

FIG. 7 depicts an exemplary process 700 of stochastic stimulation scheduling, consistent with disclosed embodiments. Process 700 can prevent pulse skipping or phase locking, while enabling the generation of consistent sets of stimulation pulses across multiple stimulation channels. In some embodiments, pulse schedule generation can be performed on a pulse-to-pulse basis, enabling on-the-fly addition or removal of stimulation channels without having to stop stimulation or determine whether stimulation channel parameters are consistent.

For convenience, the performance of process 700 is described with reference to an IPG (e.g., IPG 210) that implements the control signal generator and the controller described in FIG. 3. As may be appreciated, this description is not intended to be limiting. Process 700 can be performed using other control loop architectures. Furthermore, process 700 can be performed by an external controller (e.g., external controller 230) or a programmer (e.g., programmer 240).

In step 701, process 700 can start. In some embodiments, process 700 can start in response to the completion of a stimulation pulse. In various embodiments, process 700 can start in response to an elapsed time, according to a schedule, or in response to the modification of a stimulation partiture (e.g., the addition, removal, activation, deactivation, or modification of a stimulation channel).

In step 702 of process 700, the control signal generator can sample one or more stimulation parameter distributions associated with a stimulation channel to obtain corresponding sampled stimulation parameters.

In step 703 of process 700, the control signal generator can generate a pulse schedule using the sample stimulation parameters. In some instances, the control signal generator can also use additional stimulation parameters to generate the pulse schedule. These additional stimulation parameters can be specified parameters (e.g., through a programming process by a user), default parameters, or derived parameters. Derived parameters can be determined from combinations of other parameters (e.g., a stimulation amplitude can be derived from a sampled pulse duration using a strength duration curve, or vice versa).

In step 705 of process 700, the control signal generator can determine whether the generated pulse schedule is consistent with one or more other pulse schedules. As described herein, the control signal generator can determine whether pulse schedules are consistent according to rules, which can be specified rules (e.g., through a programming process by a user) or default rules. In some embodiments, pulse schedules can be inconsistent when they contain overlapping pulses (or, additionally, when a pulse in one pulse schedule ends within a predetermined time of the beginning of a pulse in another pulse schedule). If the pulse schedules are consistent, process 700 can proceed to step 707. Otherwise, process 700 can proceed to step 713.

In step 707 of process 700, the control signal generator can generate detection parameters, consistent with disclosed embodiments. In some embodiments, the detection parameters can include any suitable information usable to estimate the difficulty of generating sets of consistent pulse schedules. For example, the detection parameters can include an indication of the number of attempts required to generate the set of consistent stimulation parameters. In some embodiments, the detection parameters can include any suitable information usable to determine the fidelity of the generated pulse schedules. For example, the detection parameters can include an indication of the difference between the sampled parameters and any corresponding specified parameters (e.g., a jitter matrix).

In step 709 of process 700, the controller can generate stimulation parameter distribution updates based on the detection parameters received from the control signal generator. In some embodiments, the controller can estimate the difficulty of generating sets of consistent pulse schedules. For example, the controller can estimate parameter(s) of a difficulty distribution that describes the number of attempts required to generate a set of consistent pulse schedules. In some embodiments, the controller can determine error term(s) or sampled stimulation parameter distribution(s) that characterize the fidelity of the generated pulse schedules to specified pulse schedules.

Based on the estimated difficulty parameter(s) (or the estimated difficulty parameter(s) and estimated fidelity), the controller can determine updates to the stimulation parameter distributions. In some embodiments, the updates can depend on a difference between the estimated difficulty parameter(s) and target difficulty parameter(s). In some embodiments, the updates can be configured to reduce the error term(s) or shape the sampled stimulation parameter distribution(s) (e.g., by reducing the spread of the sampled stimulation parameter distribution(s)). In some embodiments, an update to a stimulation parameter distribution for a stimulation channel can depend on a specified value of the stimulation parameter for that stimulation channel. For example, an update to the variance of a stimulation parameter distribution (e.g., stimulation frequency or inter-pulse interval) for a stimulation channel can be weighted by the specified value of the mean for that stimulation parameter distribution.

In step 711 of process 700, the control signal generator can update the stimulation parameter distributions using the stimulation parameter distribution updates received from the controller. As may be appreciated, the disclosed embodiments encompass embodiments in which the controller, or another module or device, maintains the stimulation parameter distributions. In such embodiments, the controller (or the other module or device) can update the stimulation parameter distributions. The control signal generator can then obtain sampled stimulation parameter values from the controller, or other module or device.

In step 713 of process 700, in response to a determination that the pulse schedules are inconsistent, the control signal generator can re-sample the stimulation parameter distribution(s). In some embodiments, the control signal generator can re-sample the stimulation parameter distribution(s) associated with the stimulation channel of step 702. In various embodiments, the control signal generator can re-sample the stimulation parameter distribution(s) associated with all stimulation channels (or all non-protected stimulation channels).

In step 715 of process 700, the control signal generator can generate pulse schedule(s) using the sample stimulation parameter(s). In some instances, the control signal generator can also use additional stimulation parameters to generate the pulse schedule, as described with regards to step 703.

In step 717 of process 700, the control signal generator can determine whether the generated pulse schedule(s) are consistent, as described with regards to step 705. If the pulse schedules are consistent, process 700 can proceed to step 707. Otherwise, process 700 can proceed to step 719.

In step 719 of process 700, the control signal generator can determine whether an update condition is satisfied. In some embodiments, the update condition can be satisfied when the number of attempts exceeds a threshold value (e.g., 100 attempts, 1000 attempts, or a higher threshold). The threshold value can be selected to ensure that the control signal generator produced a timely new pulse schedule. It can be selected based on the speed at which the control signal generator can sample stimulation parameter distributions, generate new pulse schedules, and check pulse schedules for consistency. The faster the control signal generator can perform these functions, the higher the threshold value. When the update condition is satisfied, process 700 can proceed to step 721. Otherwise, process 700 can return to step 713 and the control signal generator can generate another set of pulse schedules.

In step 721 of process 700, in response to satisfaction of the update condition, the control signal generator can update the stimulation parameter distributions, consistent with disclosed embodiments. In some embodiments, the predetermined update can be or include an increase in the spreads of one or more stimulation parameter distributions. For example, when the stimulation parameter distributions are specified by means and variances, the predetermined update can be or include increasing the variance of at least one stimulation parameter distribution by between 10% and 1000%, or more. As an additional example, the predetermined update can be or include increasing the mean(s) of at least one stimulation parameter distribution by between 5% and 50%, or more.

In some embodiments, the control signal generator and controller can continue to manage the stimulation parameter distributions, following the update of the at least one stimulation parameter distribution. To continue the prior example, subsequent stimulation parameter distribution updates may be determined by the controller and applied to the variance increased in step 721, or the control signal generator can maintain stimulation parameter distributions having the updated means.

In some embodiments, the updates to pulse parameter distributions updated in step 721 can persist until a persistence condition is satisfied. For example, such updates can persist until a set of consistent pulse schedules is generated (or a number of sets of consistent pulse schedules are generated). As an additional example, such updates can persist for a certain time. Once the persistence condition is satisfied, the updates can be rolled back to the prior stimulation parameter distribution values (e.g., the prior means or variances).

In step 799, process 700 can finish. In some embodiments, performance of process 700 can result in the creation of a set of consistent pulse schedules (which may be used by a stimulator to provide stimulation to a patient) and in the updating of the stimulation parameter distributions.

As may be appreciated, process 700 includes a control loop. The beginning and ending of this control loop have been selected for ease of description and are not intended to be limiting. Other starting and ending points could alternatively be selected without departing from the envisioned embodiments. For example, the generation of the stimulation parameter distribution updates could be taken as the first step, and generation of the detection parameters taken as the last step.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware, but systems and methods consistent with the present disclosure can be implemented with hardware and software. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

As used herein, unless specifically stated otherwise, the term "or" encompasses all possible combinations, except where infeasible. For example, if it is stated that a component may include A or B, then, unless specifically stated otherwise or infeasible, the component may include A, or B, or A and B. As a second example, if it is stated that a component may include A, B, or C, then, unless specifically stated otherwise or infeasible, the component may include A, or B, or C, or A and B, or A and C, or B and C, or A and B and C.

The disclosed embodiments may further be described using the following clauses:

1. A stimulation scheduling method, comprising: sampling a stimulation parameter distribution for a first stimulation channel to obtain a stimulation parameter value; generating a first pulse schedule for the first stimulation channel using the stimulation parameter value; comparing the first pulse schedule to a second pulse schedule for a second stimulation channel; and based on the comparison, providing a stimulator control signal to a stimulator, the stimulator control signal based on the first pulse schedule and the stimulator configured to provide stimulation according to the stimulator control signal on the first stimulation channel.
2. The stimulation scheduling method of clause 1, the method further comprising: updating the stimulation parameter distribution based on a number of attempts required to generate the first pulse schedule.
3. The stimulation scheduling method of clause 2, wherein: updating the stimulation parameter distribution based on the number of attempts required to generate the first pulse schedule comprises: estimating a difficulty distribution parameter using the number of attempts required to generate the first pulse schedule; and updating the stimulation parameter distribution using the estimated difficulty distribution parameter.
4. The stimulation scheduling method of clause 2, wherein: updating the stimulation parameter distribution based on the number of attempts required to generate the first pulse schedule comprises: determining the number of attempts exceeds a threshold value; and in response to the determination, increasing a mean or spread of the stimulation parameter distribution.
5. The stimulation scheduling method of clause 2, wherein: updating the stimulation parameter distribution based on the number of attempts required to generate the first pulse schedule comprises: estimating a difficulty distribution parameter; and generating a control signal based on the difficulty distribution parameter.
6. The stimulation scheduling method of clause 5, wherein: updating the stimulation parameter distribution based on the number of attempts required to generate the first pulse schedule further comprises: weighting the control signal based on at least one specified stimulation parameter of the stimulation channel.

7. The stimulation scheduling method of any one of clauses 2 to 6, wherein: the stimulation parameter distribution comprises a stimulation parameter spread and updating the stimulation parameter distribution comprises updating the stimulation parameter spread.

8. The stimulation scheduling method of any one of clauses 1 to 7, the method further comprising: updating the stimulation parameter distribution using the first and second pulse schedules and specified inter-pulse intervals for the first and second stimulation channels.

9. The stimulation scheduling method of clause 8, wherein: updating the stimulation parameter distribution using the first and second pulse schedules and the specified inter-pulse intervals comprises: determining a jitter matrix based on respective differences between the first and second pulse schedules and the specified inter-pulse intervals for the first and second stimulation channels; and determining a pulse schedule fidelity using the jitter matrix.

10. The stimulation scheduling method of any one of clauses 1 to 9, wherein: the stimulation parameter value comprises an inter-pulse interval or a pulse phase duration.

11. The stimulation scheduling method of any one of clauses 1 to 9, wherein: the stimulation parameter value comprises a pulse phase duration; and generating the first pulse schedule using the stimulation parameter value comprises generating a pulse amplitude corresponding to the pulse phase duration.

12. A stimulation scheduling system, comprising: a control signal generator configured to: generate a set of consistent pulse schedules according to a set of corresponding stimulation parameter distributions; provide a stimulator control signal to a stimulator, the stimulator control signal based on the set of consistent pulse schedules and the stimulator configured to provide stimulation according to the stimulator control signal on a set of stimulation channels; and provide at least one detection parameter based on the generation of the set of consistent pulse schedules to a controller; and wherein the controller is configured to: estimate a difficulty state based on the at least one detection parameter; and update the stimulation parameter distributions based on the estimated difficulty state.

13. The stimulation scheduling system of clause 12, wherein: the stimulation parameter distributions comprise stimulation parameter spreads; and updating the stimulation parameter distributions comprises updating the stimulation parameter spreads.

14. The stimulation scheduling system of clause 13, wherein: the stimulation parameter distributions further comprise stimulation parameter means; and the updates to the stimulation parameter spreads depend upon: the estimated difficulty state; and the stimulation parameter means.

15. The stimulation scheduling system of clause 12, wherein: the stimulation parameter distributions comprise stimulation parameter means; and the controller is further configured to: determine an update condition is satisfied; and in response to the determination, update the stimulation characteristic means.

16. The stimulation scheduling system of any one of clauses 12 to 15, wherein: the at least one detection parameter comprises a number of attempts required to generate the consistent pulse schedules.

17. The stimulation scheduling system of any one of clauses 12 to 16, wherein: the estimated difficulty state comprises a parameter specifying an exponential or geometric distribution.

18. The stimulation scheduling system of any one of clauses 12 to 17, wherein: the control signal generator and the controller form a control loop configured to maintain a specified degree of difficulty in generating sets of consistent pulse schedules.

19. The stimulation scheduling system of any one of clauses 12 to 18, wherein: the stimulation parameter distributions comprise inter-pulse interval distributions or pulse phase duration distributions.

20. The stimulation scheduling system of any one of clauses 12 to 18, wherein: the stimulation parameter distributions comprise pulse phase duration distributions; and generating the set of pulse schedules comprises: sampling the pulse phase duration distributions to obtain pulse phase duration values; and generating pulse phase amplitudes corresponding to the pulse phase duration values.

21. A stimulation scheduling system, comprising: an implantable pulse generator configured to target, using a control signal generator and a controller, a degree of difficulty in generating consistent pulse schedules for a set of stimulation channels by updating stimulation parameter distributions for the stimulation channels, the stimulation parameter distributions used to generate the consistent pulse schedules.

21. The stimulation scheduling system of clause 20, wherein: the implantable pulse generator configured to is further configured to target a fidelity of the generated pulse schedules to specified stimulation parameters.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed:

1. A stimulation scheduling system, comprising:

a stimulator configured to provide stimulation according to a stimulator control signal on a set of stimulation channels;

a control signal generator configured to:

generate a set of consistent pulse schedules according to a set of corresponding stimulation parameter distributions, the stimulation parameter distributions having stimulation parameter expected values and stimulation parameter spreads;

provide a stimulator control signal to a stimulator, the stimulator control signal based on the set of consistent pulse schedules; and provide at least one detection parameter based on the generation of the set of consistent pulse schedules to a controller; and wherein the controller is configured to:

estimate a difficulty state based on the at least one detection parameter; and update the stimulation parameter distributions based on the estimated difficulty state.

2. The stimulation scheduling system of claim 1, wherein: updating the stimulation parameter distributions comprises updating the stimulation parameter spreads.

3. The stimulation scheduling system of claim 2, wherein: the updates to the stimulation parameter spreads depend upon:

the estimated difficulty state; and the stimulation parameter expected values.

4. The stimulation scheduling system of claim 1, wherein:

the controller is further configured to:

determine an update condition is satisfied; and in response to the determination, update the stimulation parameter expected values.

5. The stimulation scheduling system of claim 1, wherein:

the at least one detection parameter comprises a number of attempts required to generate the consistent pulse schedules.

6. The stimulation scheduling system of claim 1, wherein:

the estimated difficulty state comprises a parameter specifying an exponential or geometric distribution.

7. The stimulation scheduling system of claim 1, wherein:

the control signal generator and the controller form a control loop configured to maintain a specified degree of difficulty in generating sets of consistent pulse schedules.

8. The stimulation scheduling system of claim 1, wherein:

the stimulation parameter distributions comprise inter-pulse interval distributions or pulse phase duration distributions.

9. The stimulation scheduling system of claim 1, wherein:

the stimulation parameter distributions comprise pulse phase duration distributions; and generating the set of consistent pulse schedules comprises:

sampling the pulse phase duration distributions to obtain pulse phase duration values; and generating pulse phase amplitudes corresponding to the pulse phase duration values.

10. A stimulation scheduling system, comprising:

an implantable pulse generator configured to target, using a control signal generator and a controller, a degree of difficulty in generating consistent pulse schedules for a set of stimulation channels by updating stimulation parameter distributions for the stimulation channels, wherein the stimulation parameter distributions have stimulation parameter expected values and stimulation parameter spreads and are used to generate the consistent pulse schedules and to provide stimulation on the set of stimulation channels according to the consistent pulse schedules.

11. The stimulation scheduling system of claim 10, wherein:

the implantable pulse generator is further configured to target a fidelity of the generated pulse schedules to specified stimulation parameters.

12. A stimulation scheduling method, comprising:

sampling a stimulation parameter distribution, the stimulation parameter distribution having a stimulation parameter expected value and a stimulation parameter spread, for a first stimulation channel to obtain a stimulation parameter value;

generating a first pulse schedule for the first stimulation channel using the stimulation parameter value;

comparing the first pulse schedule to a second pulse schedule for a second stimulation channel; and based on a consistency result of the comparison, providing a stimulator control signal to a stimulator, the stimulator control signal based on the first pulse schedule and the stimulator configured to provide stimulation according to the stimulator control signal on the first stimulation channel.

13. The stimulation scheduling method of claim 12, the method further comprising:

updating the stimulation parameter distribution based on a number of attempts required to generate the first pulse schedule.

14. The stimulation scheduling method of claim 13, wherein:

updating the stimulation parameter distribution comprises updating the stimulation parameter spread.

15. The stimulation scheduling method of claim 13, wherein:

updating the stimulation parameter distribution based on the number of attempts required to generate the first pulse schedule comprises:

estimating a difficulty distribution parameter using the number of attempts required to generate the first pulse schedule; and updating the stimulation parameter distribution using the estimated difficulty distribution parameter.

16. The stimulation scheduling method of claim 13, wherein:

updating the stimulation parameter distribution based on the number of attempts required to generate the first pulse schedule comprises:

determining the number of attempts exceeds a threshold value; and in response to the determination, increasing the stimulation parameter expected value or the stimulation parameter spread of the stimulation parameter distribution.

17. The stimulation scheduling method of claim 13, wherein:

updating the stimulation parameter distribution based on the number of attempts required to generate the first pulse schedule comprises:

estimating a difficulty distribution parameter; and generating a control signal based on the difficulty distribution parameter.

18. The stimulation scheduling method of claim 17, wherein:

updating the stimulation parameter distribution based on the number of attempts required to generate the first pulse schedule further comprises:

weighting the control signal based on at least one specified stimulation parameter of the stimulation channel.

19. The stimulation scheduling method of claim 12, the method further comprising:

updating the stimulation parameter distribution using the first and second pulse schedules and specified inter-pulse intervals for the first and second stimulation channels.

20. The stimulation scheduling method of claim 19, wherein:

updating the stimulation parameter distribution using the first and second pulse schedules and the specified inter-pulse intervals comprises:

determining a jitter matrix based on respective differences between the first and second pulse schedules and the specified inter-pulse intervals for the first and second stimulation channels; and determining a pulse schedule fidelity using the jitter matrix.

21. The stimulation scheduling method of claim 12, wherein:

the stimulation parameter value comprises an inter-pulse interval or a pulse phase duration.

22. The stimulation scheduling method of claim 12, wherein:

the stimulation parameter value comprises a pulse phase duration; and generating the first pulse schedule using the stimulation parameter value comprises generating a pulse amplitude corresponding to the pulse phase duration.

* * * * *